United States Patent
Levy et al.

(10) Patent No.: US 9,795,428 B2
(45) Date of Patent: Oct. 24, 2017

(54) BONE IMPLANTATION AND STABILIZATION ASSEMBLY INCLUDING DEPLOYMENT DEVICE

(75) Inventors: Mark M. Levy, Raanana (IL); Raphael F. Meloul, Caesarea (IL); Elad Sapir, Kfar Yona (IL); Yair Spanier, Padres-Hanna (IL); Hagay Drori, Petah Tikva (IL); Michal Ruchelsman, Haifa (IL); Eyal Zylberberg, Kfar Yona (IL)

(73) Assignee: Expanding Orthopedics Inc., Memphis, TN (US)

( * ) Notice: Subject to any disclaimer, the term of this patent is extended or adjusted under 35 U.S.C. 154(b) by 416 days.

(21) Appl. No.: 13/255,992

(22) PCT Filed: Mar. 12, 2010

(86) PCT No.: PCT/US2010/027163
§ 371 (c)(1),
(2), (4) Date: Sep. 12, 2011

(87) PCT Pub. No.: WO2010/105174
PCT Pub. Date: Sep. 16, 2010

(65) Prior Publication Data
US 2011/0319946 A1  Dec. 29, 2011

Related U.S. Application Data

(60) Provisional application No. 61/159,505, filed on Mar. 12, 2009.

(51) Int. Cl.
A61B 17/70 (2006.01)
A61B 17/86 (2006.01)
A61B 17/84 (2006.01)

(52) U.S. Cl.
CPC ...... *A61B 17/8625* (2013.01); *A61B 17/7032* (2013.01); *A61B 17/7035* (2013.01);
(Continued)

(58) Field of Classification Search
CPC .............. A61B 17/7082; A61B 17/844; A61B 17/8625; A61B 17/864; A61B 17/8685; A61B 17/8858; A61B 2017/8655
(Continued)

(56) References Cited

U.S. PATENT DOCUMENTS 5,209,753 A * 5/1993 Biedermann et al. ........ 606/304
5,702,216 A * 12/1997 Wu ................................ 411/32
(Continued)

OTHER PUBLICATIONS

Yuehuei, An. "Internal Fixation in Osteoporotic Bone": Thieme. Jul. 2002, p. 79-80.*
PCT/US2010/027163 PCT Search Report.

*Primary Examiner* — Jan Christopher Merene
*Assistant Examiner* — Atiya Mahmud
(74) *Attorney, Agent, or Firm* — Dekel Patent Ltd.; David Klein

(57) ABSTRACT

The present disclosure provides for improved bone implantation and stabilization assemblies, and improved systems/methods for deploying and/or undeploying such bone implantation and stabilization assemblies. More particularly, the present disclosure provides for improved devices, systems and methods for stabilizing bones and/or bone segments. In exemplary embodiments, the present disclosure provides for improved devices, systems and methods for deploying bone implantation and stabilization assemblies into bone tissue (e g., spinal structure, vertebrae, cancellous bone, cortical bone, etc.) in order to stabilize bones and/or bone segments.

18 Claims, 45 Drawing Sheets

(52) U.S. Cl.
CPC ...... *A61B 17/7037* (2013.01); *A61B 17/7049* (2013.01); *A61B 17/7082* (2013.01); *A61B 17/844* (2013.01); *A61B 17/864* (2013.01); *A61B 17/8685* (2013.01); *A61B 2017/8655* (2013.01)

(58) Field of Classification Search
USPC ....... 606/264–272, 309, 310, 313, 314, 318, 606/323, 325–328, 303, 304, 319
See application file for complete search history.

(56) References Cited

U.S. PATENT DOCUMENTS

| | | | |
|---|---|---|---|
| 6,540,749 B2 | 4/2003 | Schaeffer et al. | |
| 6,668,688 B2* | 12/2003 | Zhao et al. | 81/439 |
| 6,991,461 B2* | 1/2006 | Gittleman | 433/173 |
| 2002/0165544 A1 | 11/2002 | Perren et al. | |
| 2003/0100896 A1* | 5/2003 | Biedermann et al. | 606/61 |
| 2006/0052788 A1* | 3/2006 | Thelen et al. | 606/72 |
| 2008/0288003 A1* | 11/2008 | McKinley | 606/313 |
| 2009/0005821 A1 | 1/2009 | Chirico et al. | |
| 2009/0204216 A1* | 8/2009 | Biedermann et al. | 623/17.12 |
| 2010/0228301 A1* | 9/2010 | Greenhalgh et al. | 606/313 |

* cited by examiner

Deployed – locked:
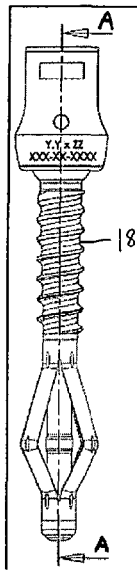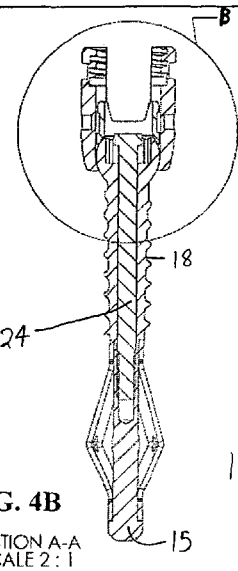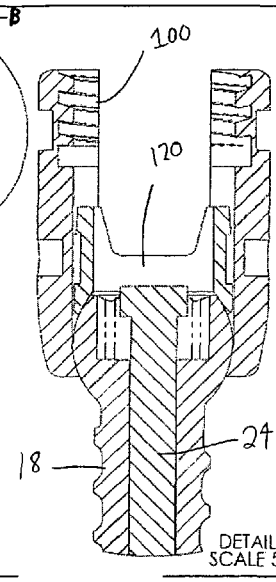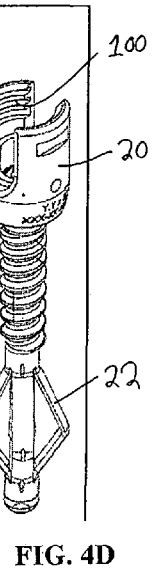
FIG. 4A   FIG. 4B   FIG. 4C   FIG. 4D
Deployed – locked with assembled rod and set screw:
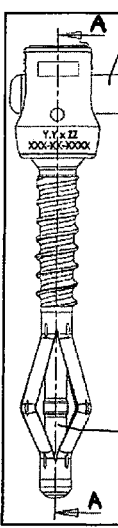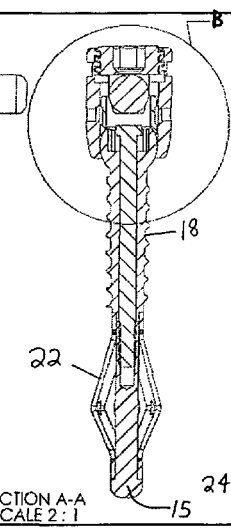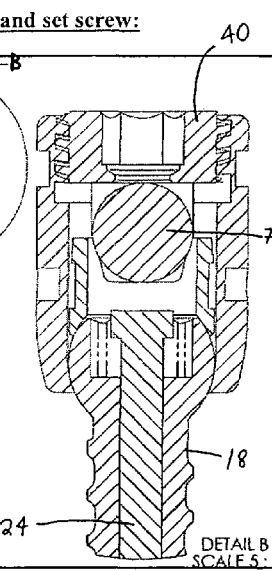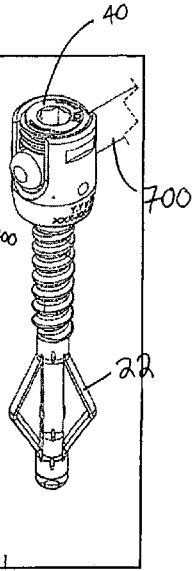
FIG. 5A   FIG. 5B   FIG. 5C   FIG. 5D

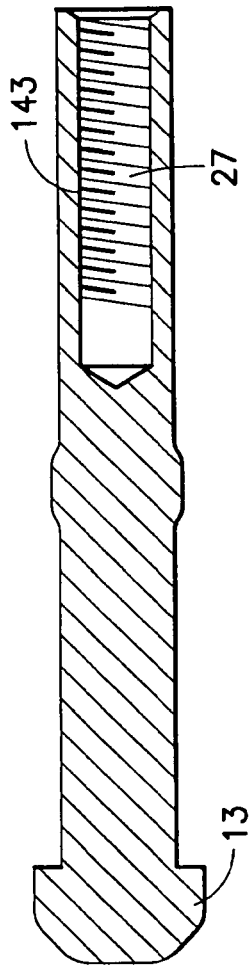
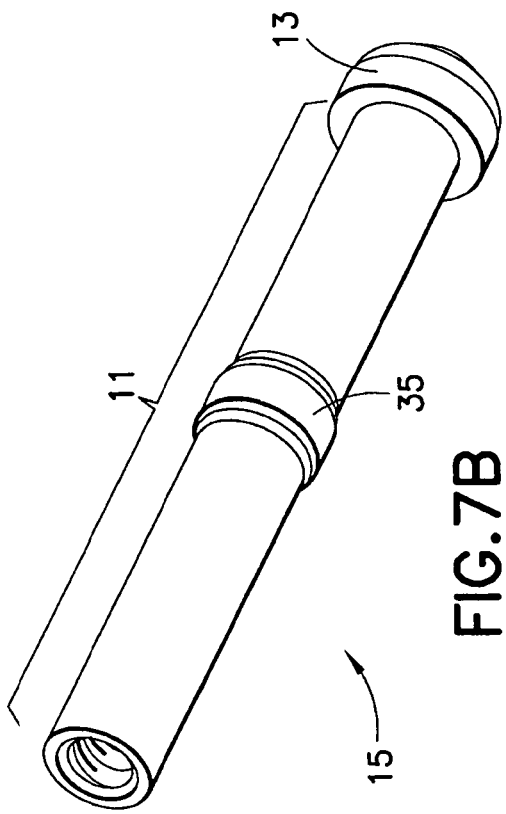
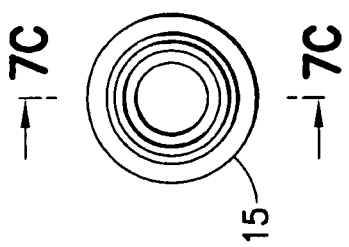
FIG.7C
FIG.7B
FIG.7A

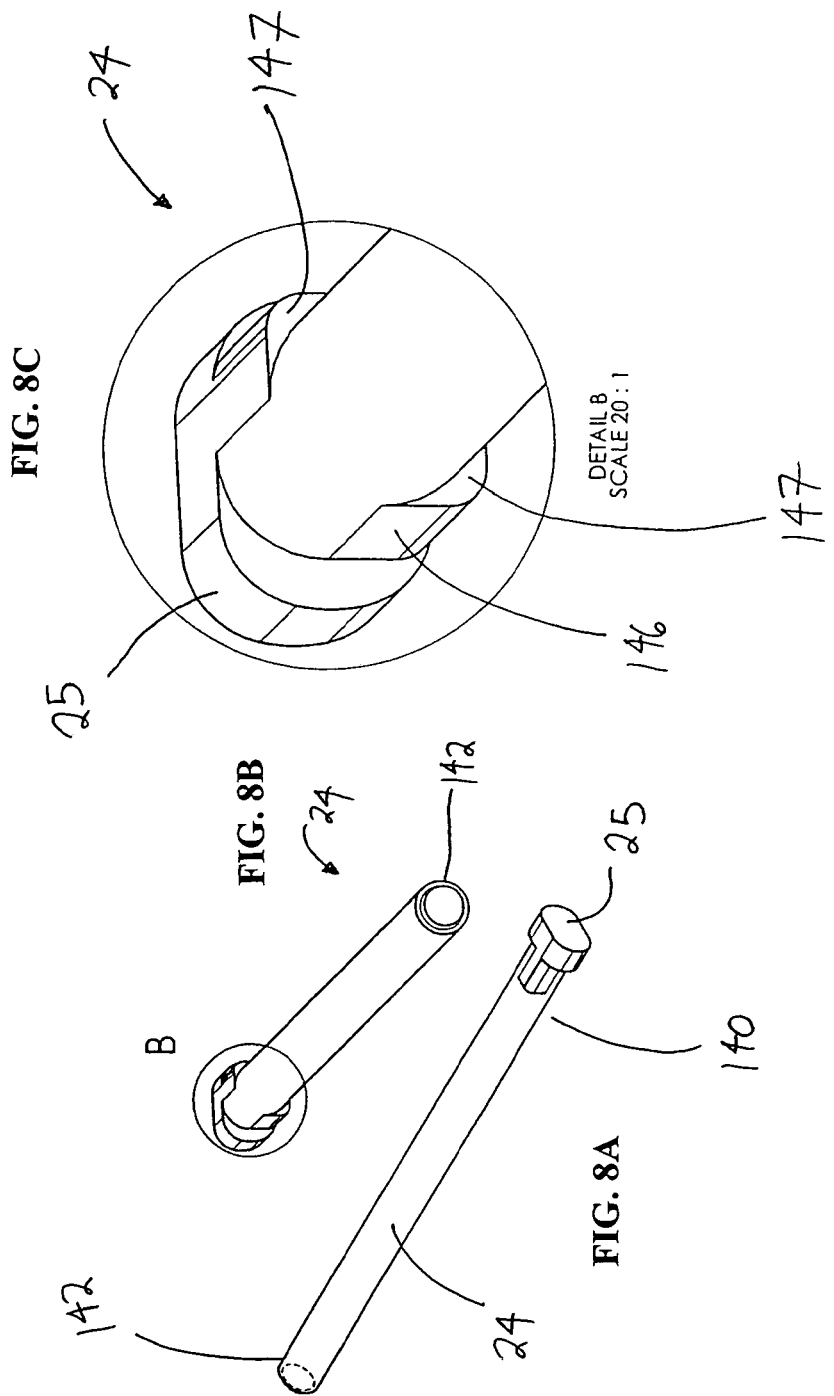

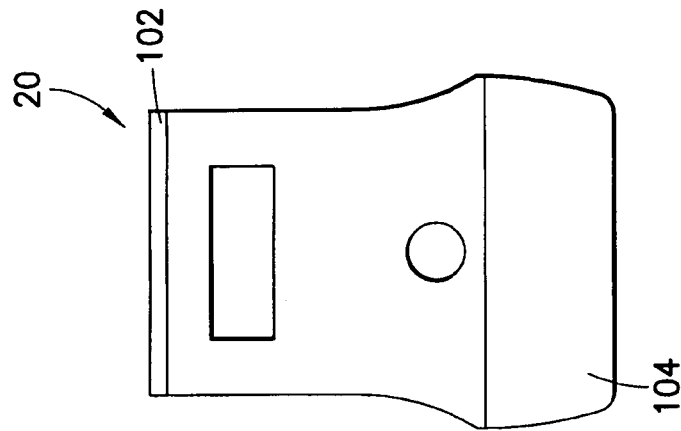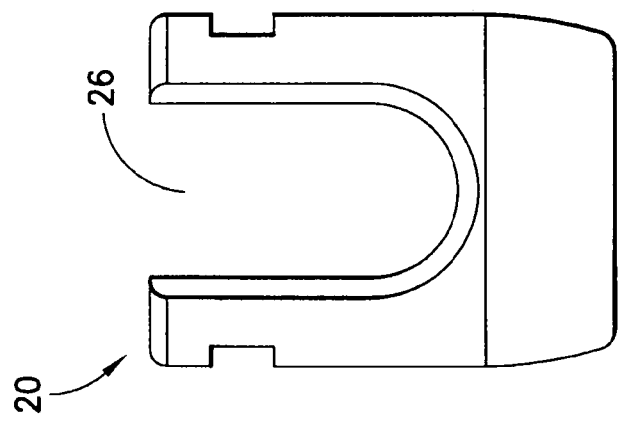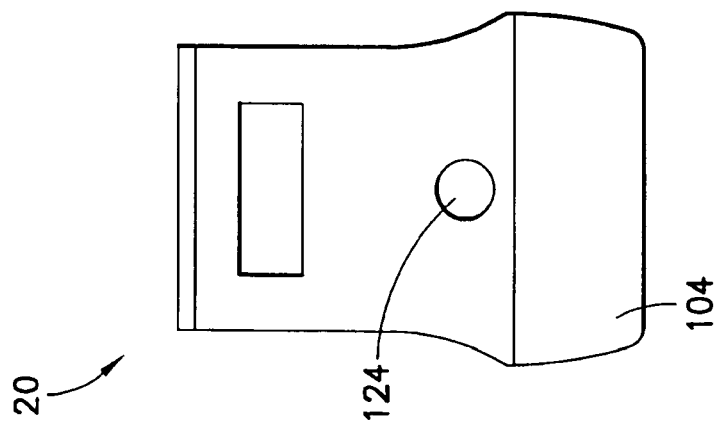

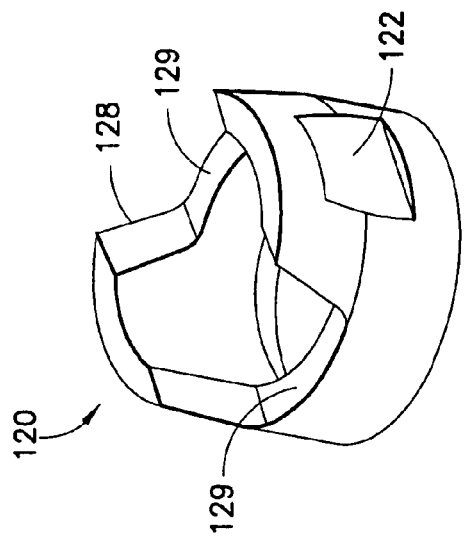
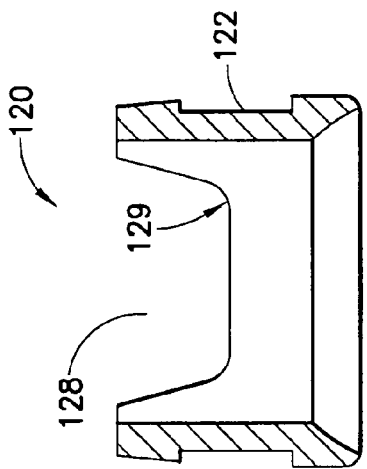
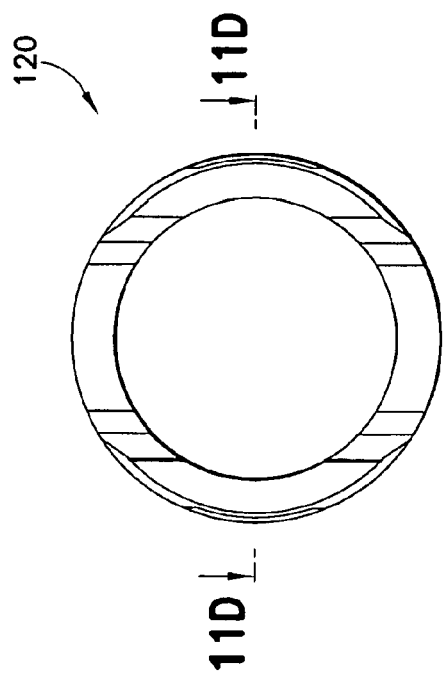
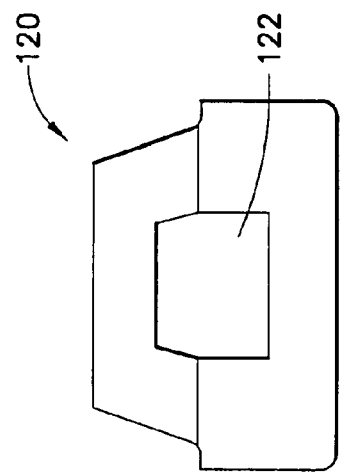
FIG.11C
FIG.11D
FIG.11A
FIG.11B

SECTION A-A

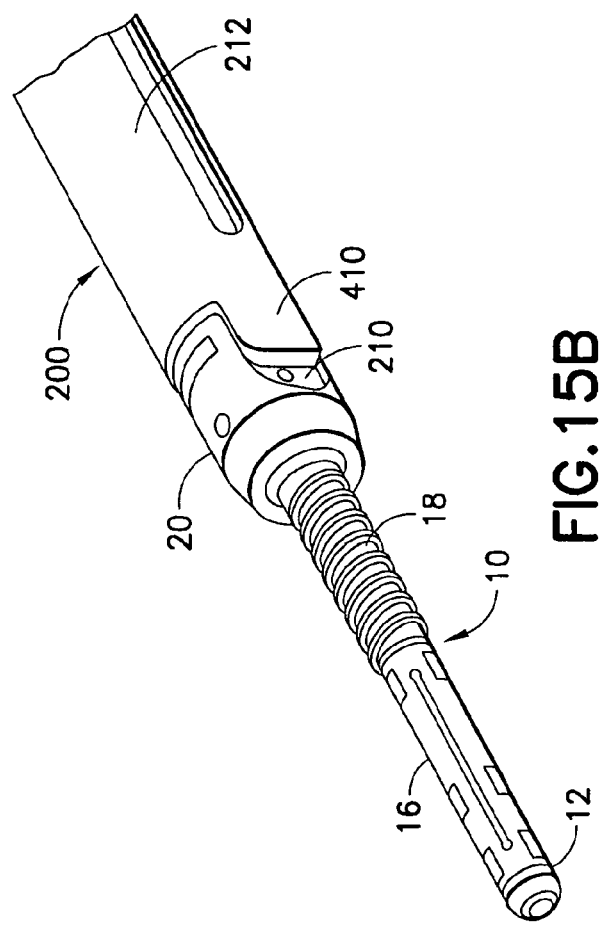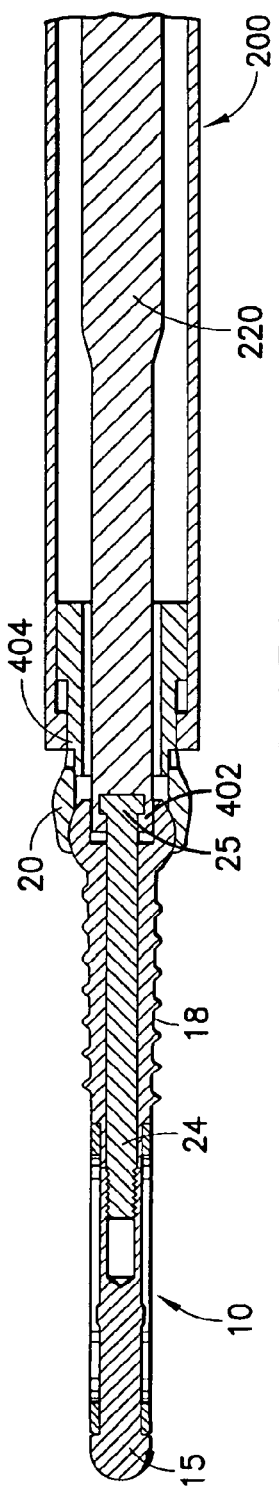
FIG.15B
FIG.15A

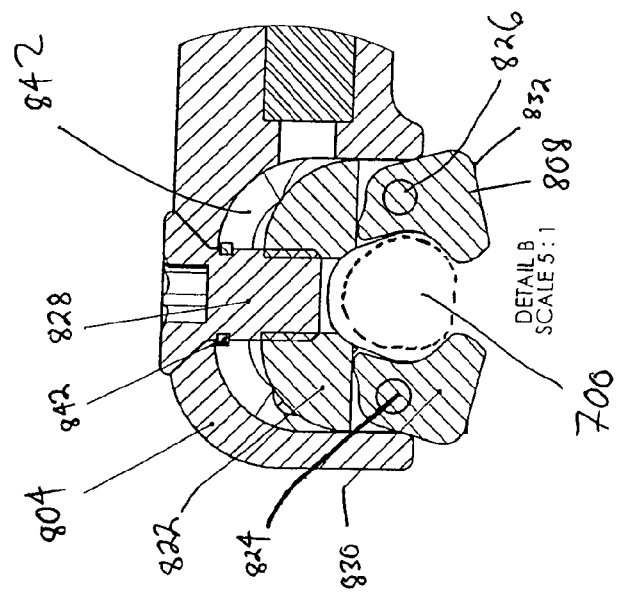
FIG. 18D
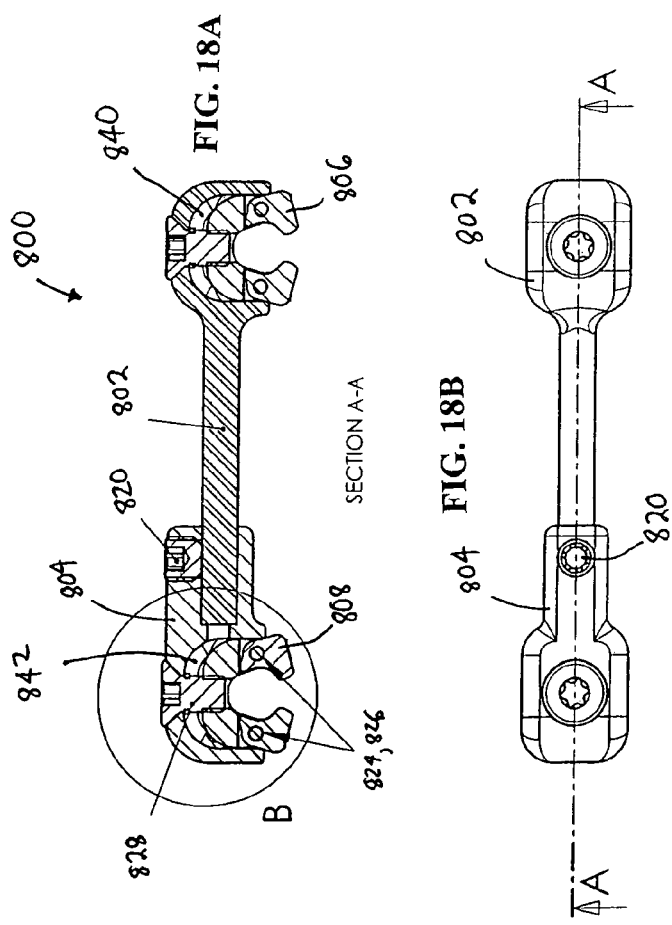
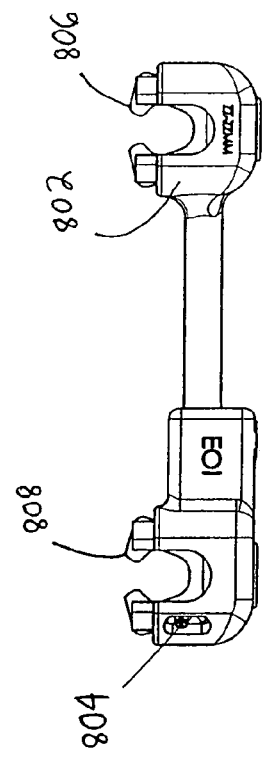
FIG. 18A
FIG. 18B
FIG. 18C

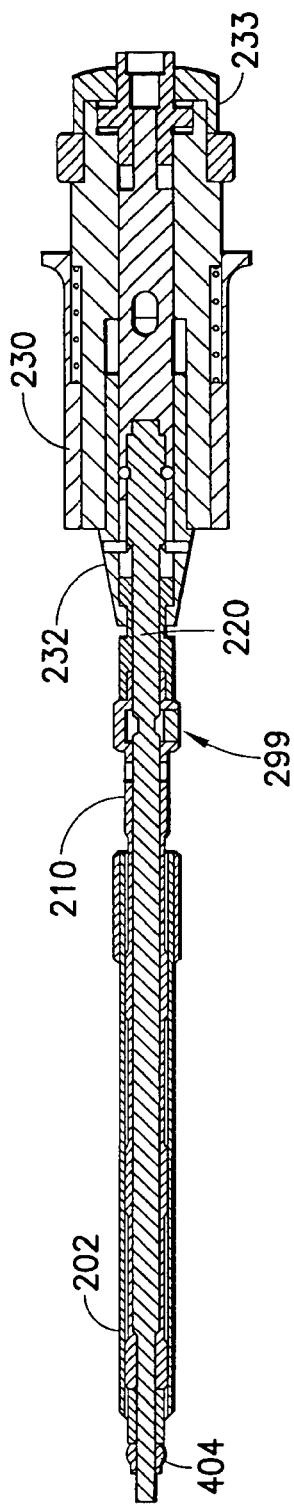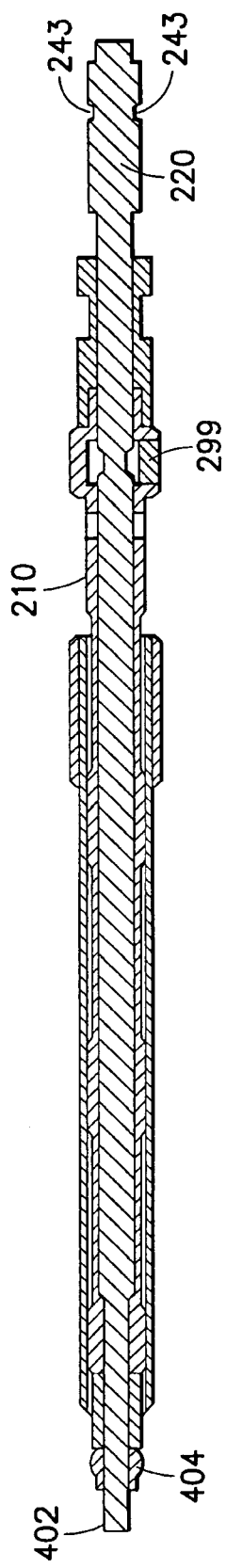
FIG.28A
FIG.28B

BONE IMPLANTATION AND STABILIZATION ASSEMBLY INCLUDING DEPLOYMENT DEVICE

CROSS REFERENCE TO RELATED APPLICATIONS

This application claims the benefit of U.S. Provisional App. Ser. No. 61/159,505, filed Mar. 12, 2009, the entire contents of which is herein incorporated by reference in its entirety.

BACKGROUND

1. Technical Field

The present disclosure relates to orthopedic devices and, more particularly, to bone implantation and stabilization assemblies, and devices for deploying and/or undeploying such bone implantation and stabilization assemblies.

2. Background Art

In general, bone implantation and stabilization assemblies (e.g., pedicle or bone screw or anchor assemblies) and the like are known in the art and may be used for connecting vertebrae or other spinal or bone structure to rods or the like during surgery (e.g., spinal surgery). For example, U.S. Pat. No. 5,443,467 to Biedermann incorporates a ball joint at the connection to the rod to allow the surgeon some flexibility in placing the screws. Tightening a nut on the screw compresses the ball joint components to lock the angular position of the ball joint.

Some typical bone implantation and stabilization assemblies (e.g., bone screw or anchor assemblies) generally include a screw member or anchoring element (e.g., pedicle screw) having a threaded portion and a head, the head generally having a spherically shaped portion, the assembly also typically having a cylindrical-like receiver member for receiving the head of the screw member and a rod (e.g., stabilization rod). However, no bone implantation and stabilization assembly design is free of problems and there is still a need for an assembly that is user-friendly suiting all kinds of bone conditions and which permits improved implantation and/or stabilization of the assembly (e.g., improved implantation and/or stabilization of the bone screw or bone anchoring element), and/or which permits improved deployment and/or undeployment of the assembly.

As another example, fractures of limb bones have been treated with internal fixation or stabilization devices, such as nails running inside the medullary canal of a fractured bone, plates lying on the surface of a bone, and/or screws affixing both ends of a fractured bone together. In general, an intramedullary fixation method is a traditional procedure for treating long bone fractures. Such methods typically involve affixing the bone fracture using intramedullary nails, without disturbing the periosteum of the bone. Some disadvantages associated with conventional intramedullary fixation methods include lack of rotation stability (e.g., fractured bone segments connected by a nail can rotate relative to each other), lack of longitudinal stability (e.g., fractured bone segments connected by a nail can move relative to each other along an axis of the nail), collapse of the fracture site in some fracture types, and/or undesired backup of nails. Additionally, some intramedullary fixation methods may introduce interlocking screws across the nail, creating some disadvantages.

For example, conventional intramedullary fixation nails for long bones may include a rigid structure that may be locked at their end portions by the addition of screws transversally applied through the bone walls and the nail itself. In general, this additional step typically increases the duration and/or complexity of the operation, and may require additional skin incisions and/or longer use of an image intensifier (e.g., X-ray). Moreover, undesired gaps between the bone ends may originate from the screws, which are permanent unless removed in a new operation. In addition, metallic intramedullary nails may propagate contamination through the entire canal, despite attempts at cleaning the fracture site, which may lead to bone infection. While increased stability in an intramedullary fixation device may be desirable, it may also be desired in some situations to remove or change the stabilization or fixation device (e.g., in the event of infection or non-union). However, in such scenarios, the stabilization or fixation device may be difficult to remove without significantly damaging bone tissue.

Thus, despite efforts to date, a need remains for advantageous and efficient systems/methods that provide for improved bone implantation and stabilization assemblies, and improved systems/methods for deploying and/or undeploying such advantageous bone implantation and stabilization assemblies. These and other inefficiencies and opportunities for improvement are addressed and/or overcome by the systems/methods of the present disclosure.

SUMMARY

The present disclosure provides for improved bone implantation and stabilization assemblies, and improved systems/methods for deploying and/or undeploying such advantageous bone implantation and stabilization assemblies. In general, the present disclosure provides for improved devices, systems and methods for stabilizing bones and/or bone segments. In exemplary embodiments, the present disclosure provides for improved devices, systems and methods for deploying bone implantation and stabilization assemblies into bone tissue (e.g., spinal structure, vertebrae, cancellous bone, cortical bone, etc.) in order to stabilize bones and/or bone segments. For example, the bone implantation and stabilization assemblies may be deployed in bone and/or bone segments to fasten different elements to spinal structure, to fasten fusion rods between adjoining vertebrae, to fasten the left and right side pedicles of the same vertebra together, or to connect bones or sections of the same bone in other parts of the body (e.g., to stabilize bones and/or bone segments that have become displaced and/or unstable due to fractures or the like).

The present disclosure also provides for an orthopedic device including: (a) a body that defines a longitudinal axis, said body including: (i) a first body region defining a first lumen, (ii) a second body region defining a channel extending within the interior of the second body region, and (iii) an anchor region positioned at least in part between the first body region and the second body region; and (b) an actuator, at least a first portion of the actuator configured and dimensioned to be at least partially disposed within the first lumen, and at least a second portion of the actuator configured and dimensioned to be: (i) at least partially disposed within the channel of the second body region, and (ii) releasably coupled with respect to the second body region; wherein the anchor region defines a plurality of anchoring elements moveable between a non-deployed state and a plurality of deployed states; and wherein linear movement of the actuator within the body relative to the first body region causes the second body region to be displaced linearly towards the first body region, thereby causing each anchoring element to deploy outwardly relative to the axis of the body to define one of the plurality of deployed states.

The present disclosure also provides for an orthopedic device wherein each of the plurality of anchoring elements is bounded by a first anchor element end region and a second anchor element end region, and wherein the first anchor element end region is adjacent to the first body region, and the second anchor element end region is adjacent to the second body region. The present disclosure also provides for an orthopedic device wherein the anchor region defines a second lumen when the anchor region is in the non-deployed state.

The present disclosure also provides for an orthopedic device wherein at least a portion of the second body region is disposed within the second lumen of the anchor region when the anchor region is in the non-deployed state. The present disclosure also provides for an orthopedic device wherein at least a portion of the first body region is disposed within the second lumen of the anchor region when the anchor region is in the non-deployed state. The present disclosure also provides for an orthopedic device wherein the first body region, the second body region, and the anchor region in the non-deployed state are hollow regions. The present disclosure also provides for an orthopedic device wherein the first body region or the second body region includes external threads. The present disclosure also provides for an orthopedic device wherein the anchor region includes external threads.

The present disclosure also provides for an orthopedic device wherein the second body region includes: (i) an inner region, the inner region at least partially disposed within the anchor region when the anchor region is in the non-deployed state, and (ii) a second body end region. The present disclosure also provides for an orthopedic device wherein the second body end region is not substantially disposed within the anchor region when the anchor region is in the non-deployed state. The present disclosure also provides for an orthopedic device wherein the inner region is substantially disposed within the anchor region when the anchor region is in the non-deployed state. The present disclosure also provides for an orthopedic device wherein the inner region is removable. The present disclosure also provides for an orthopedic device wherein the inner region includes a protrusion, the protrusion configured and dimensioned to allow at least a portion of the anchoring elements to be substantially adjacent to the protrusion when the anchor region is in the non-deployed state.

The present disclosure also provides for an orthopedic device wherein the anchor region is substantially linear when the anchor region is in the non-deployed state. The present disclosure also provides for an orthopedic device wherein the anchor region is substantially aligned with the longitudinal axis of the body when the anchor region is in the non-deployed state. The present disclosure also provides for an orthopedic device wherein the anchor region in the non-deployed state has a substantially uniform outer diameter. The present disclosure also provides for an orthopedic device wherein the first anchor element end region is coupled or secured to the first body region, and the second anchor element end region is coupled or secured to the second body region.

The present disclosure also provides for an orthopedic device wherein the first anchor element end region is integrally formed from the first body region, and the second anchor element end region is integrally formed from the second body region. The present disclosure also provides for an orthopedic device wherein the body is a hollow body, and wherein the first body region, the anchor region, and the second body region are integrally formed from the hollow body. The present disclosure also provides for an orthopedic device wherein each of the anchoring elements buckle outwardly relative to the longitudinal axis of the body to define each deployed state of the plurality of deployed states. The present disclosure also provides for an orthopedic device wherein each of the anchoring elements is a substantially flat arm or band when in the non-deployed state.

The present disclosure also provides for an orthopedic device wherein the second body end region has a substantially uniform outer diameter that is substantially the same as the outer diameter of the anchor region when the anchor region is in the non-deployed state. The present disclosure also provides for an orthopedic device wherein each anchoring element of the plurality of anchoring elements is formed by cutting longitudinal slits or cuts in the anchor region. The present disclosure also provides for an orthopedic device wherein the actuator is removable. The present disclosure also provides for an orthopedic device wherein the anchor region is a substantially porous interconnection structure. The present disclosure also provides for an orthopedic device wherein each anchoring element of the plurality of anchoring elements further includes at least one hinge region, each hinge region being configured and dimensioned to provide a hinge when each anchoring element moves outwardly to define each deployed state of the plurality of deployed states. The present disclosure also provides for an orthopedic device wherein each hinge region buckles or bends in a predetermined manner when each anchoring element moves outwardly to define each deployed state of the plurality of deployed states. The present disclosure also provides for an orthopedic device wherein each hinge region is a scored or thinned region.

The present disclosure also provides for an orthopedic device wherein the actuator is an elongate member. The present disclosure also provides for an orthopedic device wherein the actuator is pulled or pushed by a user to displace the second body region. The present disclosure also provides for an orthopedic device wherein a user inserts a deployment device into the body to engage the actuator and to move the actuator linearly. The present disclosure also provides for an orthopedic device wherein the actuator includes an engagement head, the engagement head positioned at or near the proximal end of the actuator. The present disclosure also provides for an orthopedic device wherein a user inserts a deployment device into engagement with the engagement head of the actuator to move the actuator linearly. The present disclosure also provides for an orthopedic device wherein the first body region includes a substantially spherical head, the substantially spherical head positioned at or near the proximal end of the first body region. The present disclosure also provides for an orthopedic device wherein the actuator includes at least one protrusion, the at least one protrusion being configured and dimensioned to prevent the actuator from advancing past a predetermined distal distance within the first lumen or within the channel of the second body region. The present disclosure also provides for an orthopedic device wherein the actuator further includes an engagement head positioned at or near the proximal end of the actuator, and wherein the at least one protrusion allows the engagement head to be spaced a predetermined distance proximally from the first lumen to allow a user to insert a deployment device into engagement with the engagement head of the actuator to move the actuator linearly.

The present disclosure also provides for an orthopedic device wherein the channel of the second body region extends substantially through the interior of the second body region. The present disclosure also provides for an orthopedic device wherein at least a portion of the anchor region is configured and dimensioned to have disposed within at least a portion of the actuator. The present disclosure also provides for an orthopedic device wherein the actuator is releasably coupled to the channel of the second body region. The present disclosure also provides for an orthopedic device wherein the actuator includes a distal end having a threaded region, and wherein at least a portion of the channel of the second body region includes a threaded region that is configured and dimensioned to threadably engage with the threaded region of the actuator. The present disclosure also provides for an orthopedic device wherein after each of the anchoring elements has moved outwardly relative to the longitudinal axis to define one of the deployed states, the actuator is configured to allow a user to threadably advance the actuator distally relative to the second body region to lock each anchoring arm in the defined deployed state.

The present disclosure also provides for an orthopedic device wherein after each of the anchoring elements has moved outwardly relative to the longitudinal axis to define one of the deployed states, the actuator is configured to allow a user to move the actuator linearly relative to the second body region to lock each of the anchoring elements in the defined deployed state. The present disclosure also provides for an orthopedic device wherein after each of the anchoring elements has moved outwardly relative to the longitudinal axis to define one of the deployed states, the actuator is configured to allow a user to move the actuator linearly to lock each of the anchoring elements in the defined deployed state. The present disclosure also provides for an orthopedic device wherein after each of the anchoring elements has moved outwardly relative to the longitudinal axis to define one of the deployed states, the actuator is configured to allow a user to position the actuator so that each of the anchoring elements is locked in the defined deployed state. The present disclosure also provides for an orthopedic device wherein after each of the anchoring elements has moved outwardly relative to the longitudinal axis to define one of the deployed states, the actuator is configured to allow a user to move the actuator linearly within the body relative to the first body region to force the second body region to displace linearly away from the first body region, thereby causing each of the anchoring elements to move inwardly relative to the longitudinal axis of the body to define the non-deployed state.

The present disclosure also provides for an orthopedic device further including a receiver member defining a third lumen and having a threaded region near the proximal end of the receiver member, the receiver member being configured and dimensioned to house the proximal end of the first body region; a securing member, the securing member configured and dimensioned to be disposed within the third lumen of the receiver member and to be positioned above proximal end of the first body region; a rod positioned above the securing member; and a screw, the screw configured to threadably engage with the threaded region of the receiver member to press the rod towards the securing member, thereby: (i) securing the rod between the securing member and the screw, and (ii) stabilizing the rod relative to the receiver member.

The present disclosure also provides for an orthopedic device wherein the second body region includes a first inner region and a second inner region, the first inner region configured and dimensioned to be engaged with the second inner region to substantially prevent the first and second inner regions from rotating axially which thereby substantially prevents the anchoring elements from twisting or bending during insertion or removal of the orthopedic device; and wherein linear movement of the actuator within the body relative to the first body region causes the second inner region to be displaced linearly towards the first body region and the first inner region, thereby causing each of the anchoring elements to deploy outwardly relative to the longitudinal axis of the body to define one of the plurality of deployed states.

The present disclosure also provides for an orthopedic device further including a locking member, and wherein after each of the anchoring elements has moved outwardly relative to the longitudinal axis to define one of the deployed states, the actuator is removed and the locking member is configured and dimensioned to be at least partially disposed within at least the first lumen to lock each of the anchoring elements in the defined deployed state.

The present disclosure also provides for an orthopedic device including: (a) a body that defines a longitudinal axis, said body including: (i) a first body region defining a first lumen, (ii) a second body region defining a second lumen, and (iii) a third body region defining a channel extending within the interior of the third body region; (b) a first anchor region positioned at least in part between the first body region and the second body region; (c) a second anchor region positioned at least in part between the second body region and the third body region; and (d) an actuator, at least a first portion of the actuator configured and dimensioned to be at least partially disposed within the first lumen, at least a second portion of the actuator configured and dimensioned to be at least partially disposed within the second lumen, and at least a third portion of the actuator configured and dimensioned to be: (i) at least partially disposed within the channel of the third body region, and (ii) releasably coupled with respect to the third body region; wherein the first and second anchor regions each define a plurality of anchoring elements movable between a non-deployed state and a plurality of deployed states; and wherein linear movement of the actuator within the body relative to the first body region causes the second and third body regions to be displaced linearly towards the first body region, thereby causing each of the plurality of anchoring elements to deploy outwardly relative to the longitudinal axis of the body to define one of the plurality of deployed states.

The present disclosure also provides for an orthopedic device including: (a) a body that defines a longitudinal axis, the body including: (i) a first body region defining a lumen, (ii) a second body region defining a channel extending within the interior of the second body region, and (iii) an anchor region positioned at least in part between the first body region and the second body region; and (b) an actuator, at least a first portion of the actuator configured and dimensioned to be at least partially disposed within the lumen, and at least a second portion of the actuator configured and dimensioned to be: (i) at least partially disposed within the channel of the second body region, and (ii) releasably coupled with respect to the second body region; wherein the anchor region defines a plurality of anchoring elements movable between a non-deployed state and a plurality of deployed states; and wherein linear movement of the actuator within the body relative to the first body region causes the second body region to be displaced linearly away from the first body region, thereby causing each of the plurality of anchoring elements to deploy outwardly relative to the longitudinal axis of the body to define one of the plurality of deployed states.

The present disclosure also provides for an orthopedic device wherein each anchoring element of the plurality of anchoring elements includes a lever element, each lever element being coupled to the anchoring element and to the second body region. The present disclosure also provides for an orthopedic device wherein each anchoring element and each lever is integrally formed from a hollow structure. The present disclosure also provides for an orthopedic device wherein after each of the anchoring elements has moved outwardly to define one of the deployed states, the actuator is configured to allow a user to move the actuator linearly within the body relative to the first body region to force the second body region to displace linearly towards the first body region, thereby causing each of the anchoring elements to move inwardly relative to the longitudinal axis of the body to define the non-deployed state.

The present disclosure also provides for a deployment device including: a sleeve; a shaft at least partially disposed within the sleeve, a distal end of the shaft configured and dimensioned to releasably couple to an expandable orthopedic device; a deployment member at least partially disposed within the shaft; a connector member releasably coupled to the shaft and to the deployment member; and a first handle releasably coupled to the connector member; wherein a distal end of the deployment member is configured and dimensioned to releasably engage an actuator of the expandable orthopedic device; and wherein rotation of the first handle causes the deployment member and the actuator to move linearly, thereby deploying or un-deploying the expandable orthopedic device.

The present disclosure also provides for a deployment device wherein the sleeve is a counter-rotation or a counter-torque sleeve. The present disclosure also provides for a deployment device wherein the device further comprises a second handle releasably coupled to the connector member. The present disclosure also provides for a deployment device wherein the deployment member is a pull or push rod. The present disclosure also provides for a deployment device wherein the shaft includes a threaded region positioned at or near the distal end of the shaft, the threaded region configured and dimensioned to threadably engage with a threaded region of a receiver member coupled to the expandable orthopedic device to thereby releasably couple the shaft to the receiver member of the expandable orthopedic device.

The present disclosure also provides for a deployment device wherein the distal end of the shaft is configured and dimensioned to releasably couple to a receiver member coupled to the expandable orthopedic device. The present disclosure also provides for a deployment device wherein the distal end of the deployment member includes an engaging mechanism that is configured and dimensioned to releasably engage with an engagement head of the actuator of the expandable orthopedic device. The present disclosure also provides for a deployment device wherein the sleeve includes at least one engaging portion, and wherein the sleeve is slidable or rotatable relative to the shaft in the distal direction to allow the at least one engaging portion to releasably engage with the expandable orthopedic device.

The present disclosure also provides for a deployment device wherein the at least one engaging portion releasably engages with a receiver member coupled to the expandable orthopedic device. The present disclosure also provides for a deployment device wherein the first handle is configured and dimensioned to allow a user to deploy or un-deploy the expandable orthopedic device while using the force of one hand of the user.

The present disclosure also provides for a deployment device wherein the connector member further includes an outer sleeve and at least two clamps, the outer sleeve being configured and dimensioned to: (i) move proximally to thereby open the at least two clamps so that at least a portion of the deployment member may be inserted into a cavity of the connector member and at least a portion of the shaft may be positioned between the opened at least two clamps, and (ii) move distally after positioning of the at least a portion of the deployment member into the cavity and after positioning of at least a portion of the shaft between the opened at least two clamps to thereby releasably couple the connector member to the shaft and to the deployment member. The present disclosure also provides for a deployment device wherein the cavity further includes an internal hollow member and a plurality of securing members; and wherein the deployment member is releasably coupled to the connector member inside the cavity via the internal hollow member forcing the securing members into engagement with the deployment member. The present disclosure also provides for a deployment device wherein the internal hollow member includes a threaded proximal portion that is threadably engaged with a threaded portion of a handle member of the first handle.

The present disclosure also provides for a deployment device wherein the first handle is configured to translate a torque motion applied to the first handle into a translation motion of the deployment member. The present disclosure also provides for a deployment device wherein the connector member allows for the transmission of rotational movement of the first handle to linear movement of the deployment member. The present disclosure also provides for a deployment device wherein rotation of the first handle in a first direction causes the deployment member to translate proximally, and wherein rotation of the first handle in a second direction causes the deployment member to translate distally. The present disclosure also provides for a deployment device wherein the first handle is configured and dimensioned to allow a user to deploy the expandable orthopedic device to a plurality of deployed positions or to an un-deployed position. The present disclosure also provides for a deployment device wherein the full deployment limit of the expandable orthopedic device is controlled by the deployment member or by the first handle.

The present disclosure also provides for a deployment device wherein the shaft further includes a linear movement limiter, the linear movement limiter being configured and dimensioned to limit the linear movement of the deployment member. The present disclosure also provides for a deployment device wherein the linear movement limiter is adjustable. The present disclosure also provides for a deployment device wherein the linear movement limiter is a button having a step, with the step providing the linear movement limit of the deployment member. The present disclosure also provides for a deployment device wherein the first handle is a torque limit handle which includes a mechanical force limiting mechanism, the mechanical force limiting mechanism being configured and dimensioned to limit the linear pulling or pushing force of the deployment member. The present disclosure also provides for a deployment device wherein the mechanical force limiting mechanism is configured to maintain the linear pulling or pushing force of the deployment member within a predetermined range. The present disclosure also provides for a deployment device wherein the mechanical force limiting mechanism is a torque limiting mechanism or a slip mechanism. The present disclosure also provides for a device wherein the mechanical force limiting mechanism is adjustable. Additional advantageous features, functions and applications of the disclosed systems and methods of the present disclosure will be apparent from the description which follows, particularly when read in conjunction with the appended figures.

BRIEF DESCRIPTION OF THE DRAWINGS

To assist those of ordinary skill in the art in making and using the disclosed systems and methods, reference is made to the appended figures, wherein:

FIGS. 4A-4D illustrate an embodiment of a bone stabilization device or assembly according to the present disclosure, after deployment and locking;

FIGS. 5A-5D illustrate an embodiment of a bone stabilization device according to the present disclosure, after deployment and locking, with assembled rod and set screw;

FIGS. 7A-7C illustrate an embodiment of a second body region of a bone stabilization device or assembly according to the present disclosure;

FIGS. 8A-8C illustrate an embodiment of an actuator or inner rod of a bone stabilization device or assembly according to the present disclosure;

FIGS. 10A-10C illustrate front and side views of an embodiment of a receiver member of a bone stabilization device or assembly according to the present disclosure;

FIGS. 11A-11D illustrate an embodiment of a secure ring of a bone stabilization device or assembly according to the present disclosure;

FIGS. 15A and 15B illustrate a partial view of an embodiment of the distal end of a deployment and/or undeployment device holding an exemplary embodiment of a bone stabilization device or assembly according to the present disclosure;

FIGS. 18A-18D illustrate an embodiment of a cross-connector device or assembly that may be used with an embodiment of a bone stabilization device or assembly according to the present disclosure;

FIGS. 28A-28B illustrate partial cross-sectional views of the deployment and/or undeployment device depicted in FIG. 21;

DETAILED DESCRIPTION

Figure 1A:
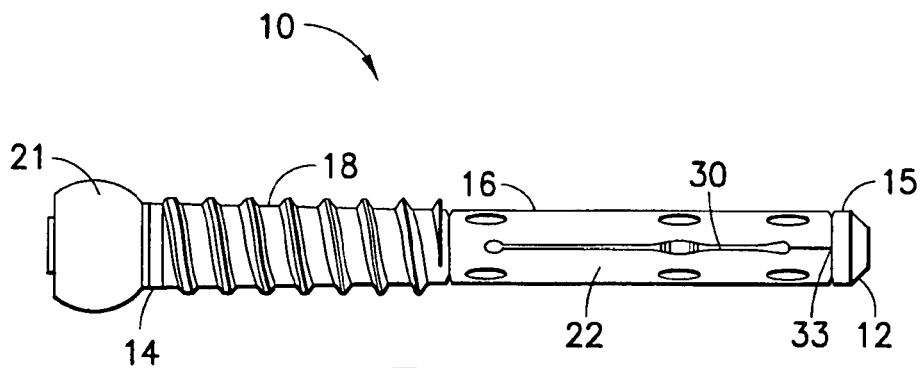
FIGS. 1A-1E illustrate an embodiment of a bone stabilization device or assembly according to the present disclosure in a collapsed or non-deployed state.
Figure 1B:
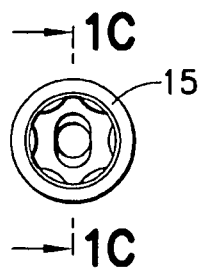
Figure 1C:
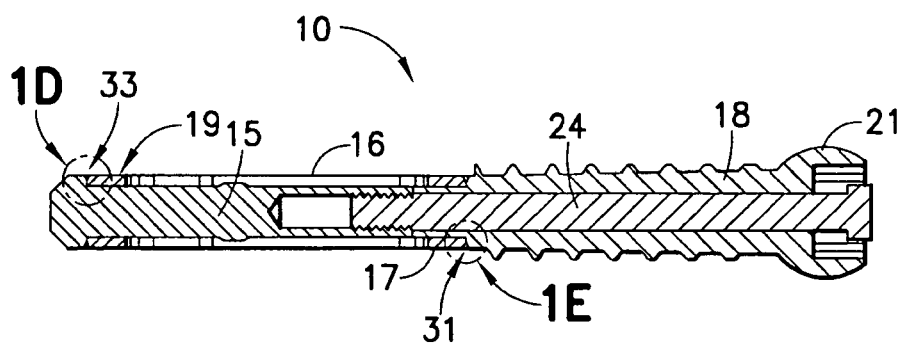
Figure 1D:
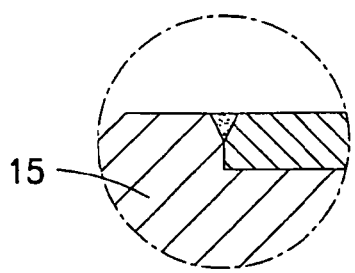
Figure 1E:
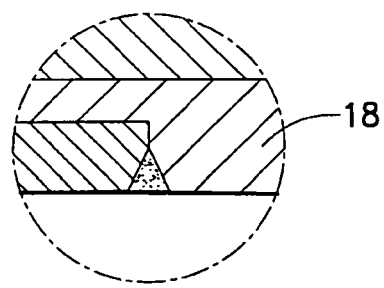

The present disclosure provides for advantageous bone implantation and stabilization assemblies, and advantageous systems/methods for deploying and/or undeploying such bone implantation and stabilization assemblies. In general, the present disclosure provides for improved devices, systems and methods for stabilizing bones and/or bone segments. In exemplary embodiments, the present disclosure provides for improved devices, systems and methods for deploying bone implantation and stabilization assemblies into bone tissue (e.g., spinal structure, vertebrae, cancellous bone, cortical bone, etc.) in order to stabilize bones and/or bone segments. For example, the bone implantation and stabilization assemblies may be deployed or implanted in bone and/or bone segments to fasten different elements to spinal structure, to fasten fusion rods between adjoining vertebrae, to fasten the left and right side pedicles of the same vertebra together, or to connect bones or sections of the same bone in other parts of the body (e.g., to stabilize bones and/or bone segments that have become displaced and/or unstable due to fractures or the like), although the present disclosure is not limited thereto. Various embodiments of the present disclosure are described hereinafter with reference to the figures. It should be noted that the figures are not necessarily drawn to scale and that elements of similar structures or functions are represented by like reference numerals throughout the figures. It should also be noted that the figures are only intended to facilitate the description of the embodiments. They are not intended as an exhaustive description of the disclosure or as a limitation on the scope of the disclosure. In addition, an illustrated embodiment need not have all the aspects or advantages shown. An aspect or an advantage described in conjunction with a particular embodiment is not necessarily limited to that embodiment and can be practiced in any other embodiments even if not so illustrated or specifically described.

Referring now to the drawings, and in particular to FIGS. 1-5, there is illustrated a bone stabilization device or assembly 10 depicting exemplary embodiments of the present disclosure. In an exemplary embodiment, the bone stabilization device or assembly 10 may be used for deployment, insertion and/or implantation into a vertebral body of a vertebra, although the present disclosure is not limited thereto. For example, the bone stabilization device or assembly 10 may be a spinal implant assembly or device, including, but not limited to, a spinal implant assembly or device 10 which may be utilized to fasten different elements to spinal structure, and/or to fasten fusion or stabilization rods between vertebrae, and/or to fasten the left and right side pedicles of the same vertebrae together. In one embodiment, when a plurality of such bone stabilization devices or implant assemblies 10 are inserted/implanted into different vertebrae, the assemblies 10 may be coupled together to thereby prevent relative movement between the vertebrae to stabilize them relative to each other.

As used in this specification, the terms "implant," "implant assembly" or "implantation" are not limited to devices or assemblies that are permanently placed inside a patient's body, and may refer to any device or assembly that is placed inside a patient's body for any duration of time, and which may be removable from the patient's body.

It is to be noted, however, that spinal implant assemblies or devices are not the only bone stabilization devices or assemblies 10 that may be used in accordance with the principles of the present disclosure, as will be readily apparent to persons skilled in the art from the description provided herein. For example, the bone stabilization devices or assemblies 10 of the present disclosure may be utilized to connect bones or sections of the same bone in other parts of the body (e.g., to stabilize long bones and/or bone segments that have become displaced and/or unstable due to fractures or the like). As such, the bone stabilization device or assembly 10 may be employed to mend a variety of fractured bones, such as, for example, the femur, tibia or humerus. The bone stabilization device or assembly 10 may be deployed using methods similar to those used for conventional intramedullary nails for bones. In one embodiment, the bone stabilization device or assembly 10 may be inserted (e.g., in the undeployed state) through a previously formed entry portal into the medullary canal of a bone, and then deployed along and/or inside the medullary canal of the bone (e.g., a fractured femur), or in the head of the femur (e.g., fractured femoral neck area). For example, a long bone stabilization device or assembly 10 may be used in knee fusion cases including the femur and tibia, and a short bone stabilization device or assembly 10 may be used with metatarsal and metacarpal bone fractures. In other embodiments, the device or assembly 10 may be inserted across the shaft of a long bone transversally, holding a plate or the like, or fixing two segments of the bone.

In exemplary embodiments of the present disclosure and as depicted in FIGS. 1-5, the bone stabilization device 10 includes a proximal end 14 having a first body region 18, a distal end 12 having a second body region 15, and an anchor region 16 extending between the first body region 18 and the second body region 15. In general and as shown in FIGS. 2-5, the first body region 18, the second body region 15 and the anchor region 16 define a longitudinal axis 28 therebetween. The first body region 18, the second body region 15 and/or the anchor region 16 may be tubular or hollow regions or the like having a circular or other cross-section, although the present disclosure is not limited thereto.

Figures 25A, 25B:
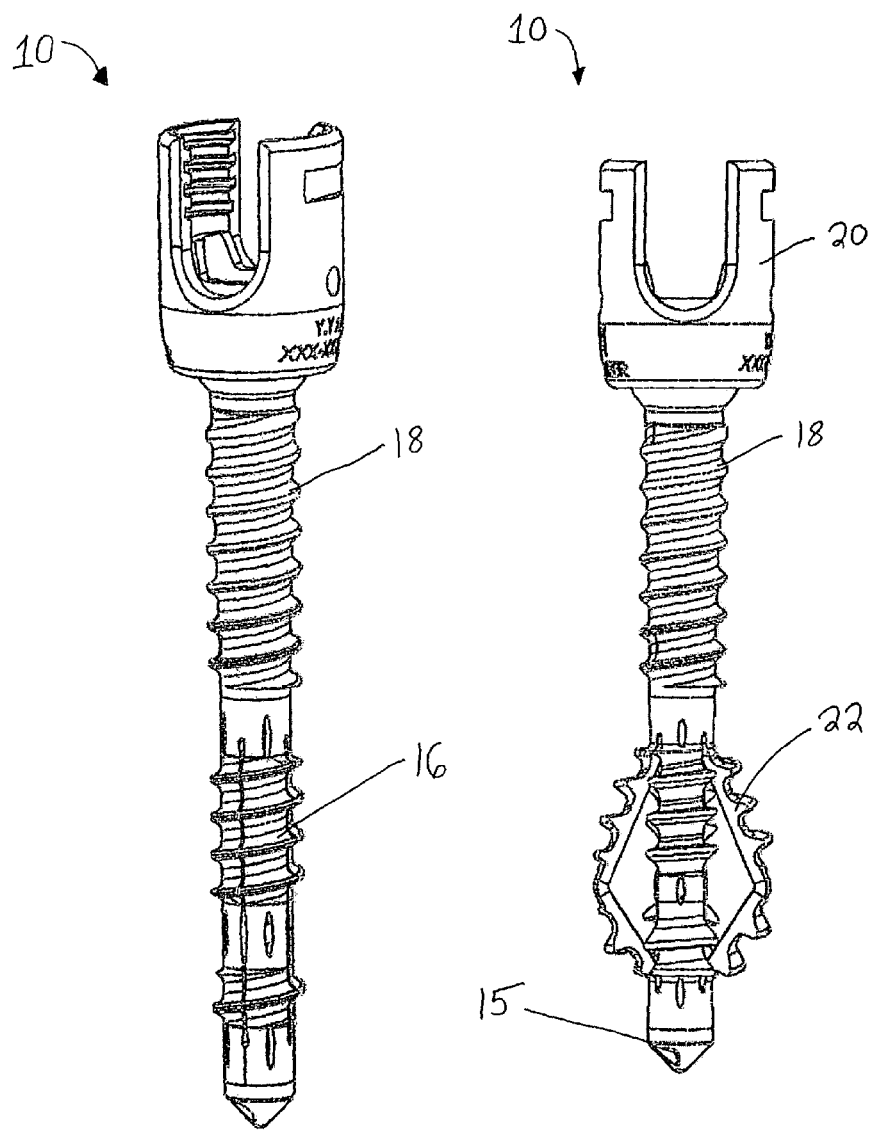
FIGS. 25A-25B illustrate another embodiment of a bone stabilization device having a threaded anchor region according to the present disclosure, before and after deployment.

In exemplary embodiments, the first body region 18 is a screw-like region which includes external threads. The first body region 18 may also include a head 21 or the like (e.g., a spherical, substantially spherical, or circular shaped screw head 21). In alternative embodiments, the second body region 15 and/or the anchor region 16 may include external threads. For example and as shown in FIGS. 25A-25B, the anchor region 16 (and/or the second body region 15) may include external threads. As shown in FIG. 6, the first body region 18 may include a first body end region 29, which may be configured to be at least partially disposed within the anchor region 16 when the anchor region 16 is in the collapsed state, as discussed below.

The first body region 18, the second body region 15 and/or the anchor region 16 may have a solid wall or may have a lattice or other pattern of holes or the like formed therein, e.g., for facilitating fluid flow therethrough, for minimizing weight, for providing a desired flexibility, and/or for allowing expansion of anchoring elements. Alternatively, first body region 18, second body region 15 and/or anchor region 16 may include a plurality of spine elements interconnected by a mesh or other interconnecting structure (e.g., a substantially porous interconnection structure), similar to the embodiments shown and described in U.S. Pat. Nos.

6,261,289 and 6,554,833, the entire contents of both being hereby incorporated by reference in their entireties.

In exemplary embodiments and as shown in FIGS. 1-5, the anchor region 16 takes the form of an expanding tube or the like, although the present disclosure is not limited thereto. In one embodiment and as shown in FIGS. 1-5 and 7, the second body region 15 includes an inner region 11, the inner region 11 being substantially disposed and/or housed within the anchor region 16 when the anchor region 16 is in the collapsed state (as discussed below). Inner region 11 may also be removable and may be used as an actuator. Also as shown, the second body region 15 may also include a second body end region 13. In an exemplary embodiment, the second body end region 13 is not substantially disposed and/or housed within the anchor region 16. As shown in FIG. 7, the inner region 11 of the second body region 15 may include a raised segment (e.g., a protrusion) or portion 35 or the like, the raised segment or protrusion 35 being configured and dimensioned to allow the hinge regions 32 of the arms 22 (discussed below) to be substantially adjacent to the raised segment or protrusion 35 of the inner region 11 when the anchor region 16 is in the collapsed state.

In one embodiment, the anchor region 16 includes a first anchor element end region 17 coupled, secured or connected (e.g., welded, threaded, adhered, hinged, jointed, etc.) to the first body region 18, and a second anchor element end region 19 coupled or connected to the second body region 15. In an alternative embodiment, the first anchor element end region 17 is adjacent to (e.g., with no physical binding to) the first body region 18, and the second anchor element end region 19 is adjacent to (e.g., with no physical binding to) the second body region 15.

In one embodiment and as shown in FIG. 1, the first anchor element end region 17 may be welded (e.g., laser welded) to the first body region 18 at or near the interface 31 of the first anchor element end region 17 and the first body region 18. The first anchor element end region 17 may also be coupled, secured or connected to the first body region 18 at the interface of the first anchor element end region 17 and the first body end region 29 (FIG. 6) disposed and/or housed within the anchor region 16. Additionally and as shown in FIG. 1, the second anchor element end region 19 may be welded (e.g., laser welded) to the second body region 15 at or near the interface 33 of the second anchor element end region 19 and the second body region 15. The second anchor element end region 19 may also be coupled, secured or connected to the second body region 15 at a portion of the interface of the second anchor element end region 19 and the inner region 11 (FIG. 7) substantially disposed and/or housed within the anchor region 16.

First anchor element end region 17 and/or second anchor element end region 19 may each define a substantially continuous anchor element end region 17, 19 (e.g., a region having substantially no slits, cuts, scores, or thinned regions, etc.), or each anchor element end region 17, 19 may include slits, cuts, scores, or thinned regions or the like. Alternatively, the first anchor element end region 17 may be integrally formed from the first body region 15, and/or the second anchor element end region 19 may be integrally formed from the second body region 15. For example, the first body region 18, first anchor element end region 17, the anchor region 16, the second anchor element end region 19, and/or the second body region 15 may be formed or fabricated from a single section of tubing or the like, with the appropriate material removed (e.g., integrally formed), as will be appreciated by those skilled in the art.

Figures 2A, 2B, 2C, 2D:
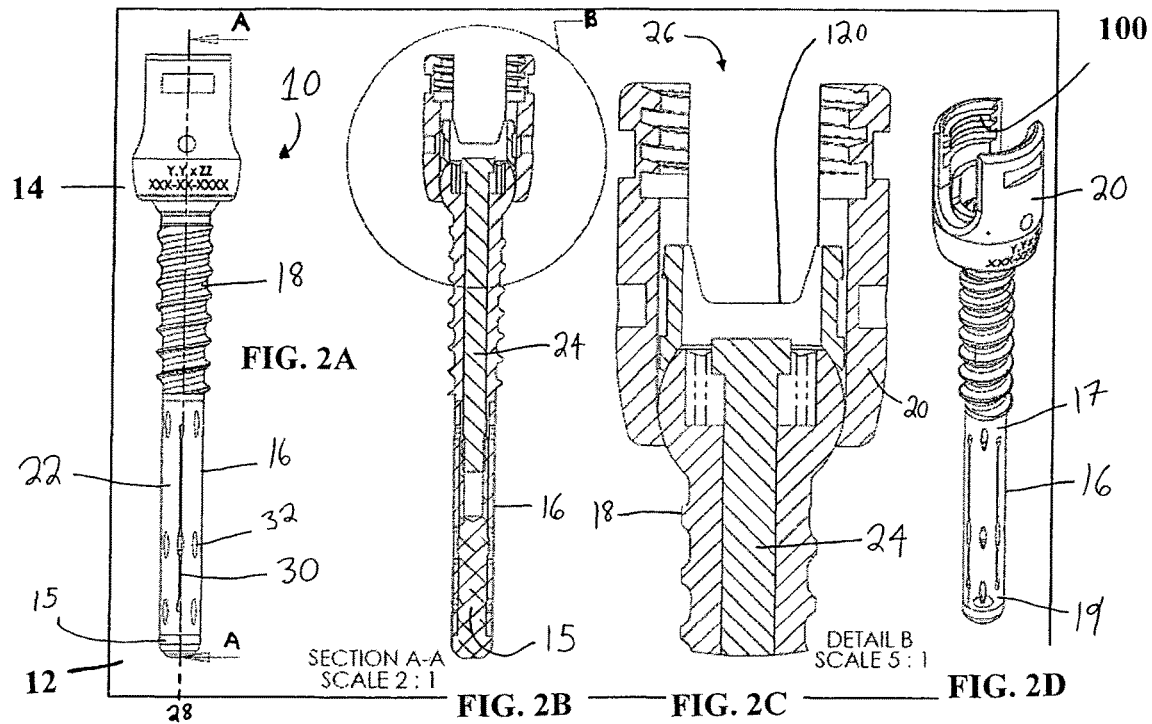
FIGS. 2A-2D illustrate an embodiment of a bone stabilization device or assembly (e.g., spinal implant and stabilization device) according to the present disclosure, before deployment.
Figures 3A, 3B, 3C, 3D:
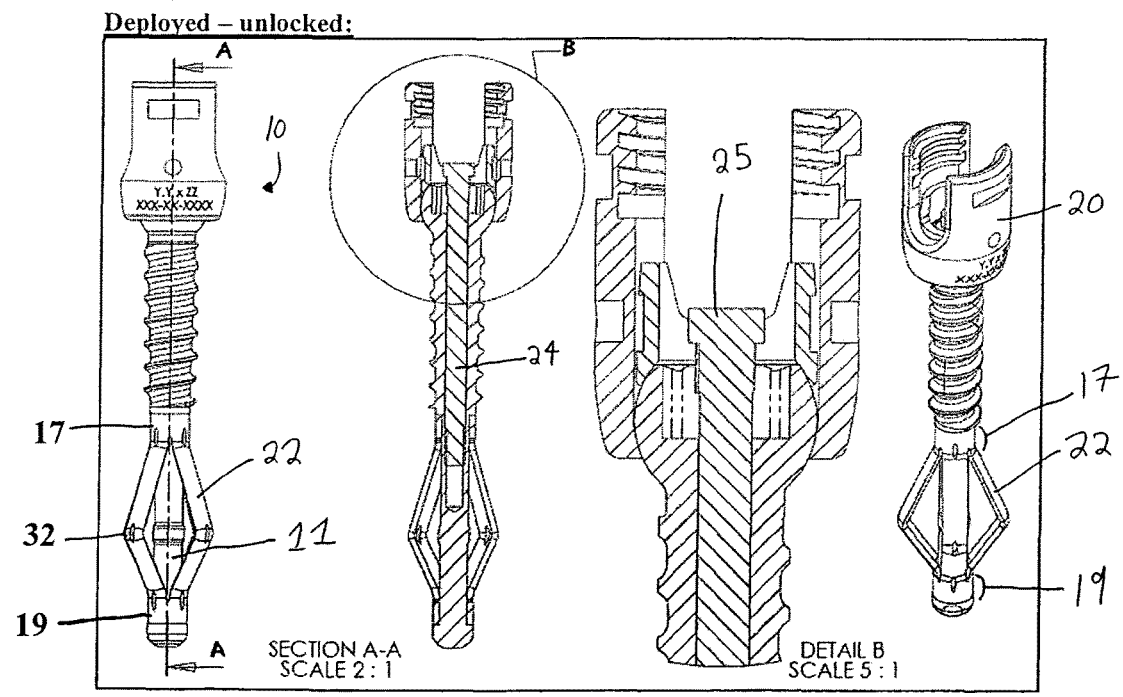
FIGS. 3A-3D illustrate an embodiment of a bone stabilization device or assembly according to the present disclosure, after deployment and before locking.
Figure 6A:
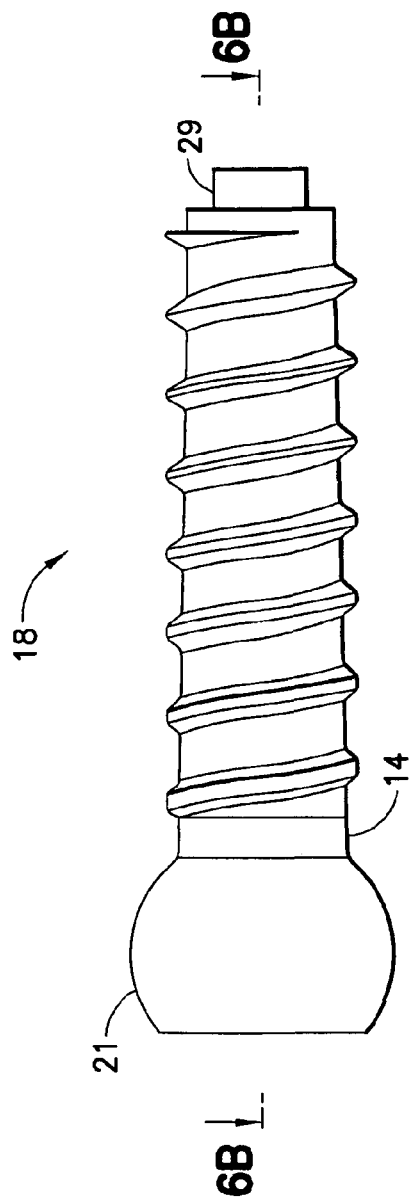
FIGS. 6A-6D illustrate an embodiment of a first body region of a bone stabilization device or assembly according to the present disclosure.
Figure 6B:
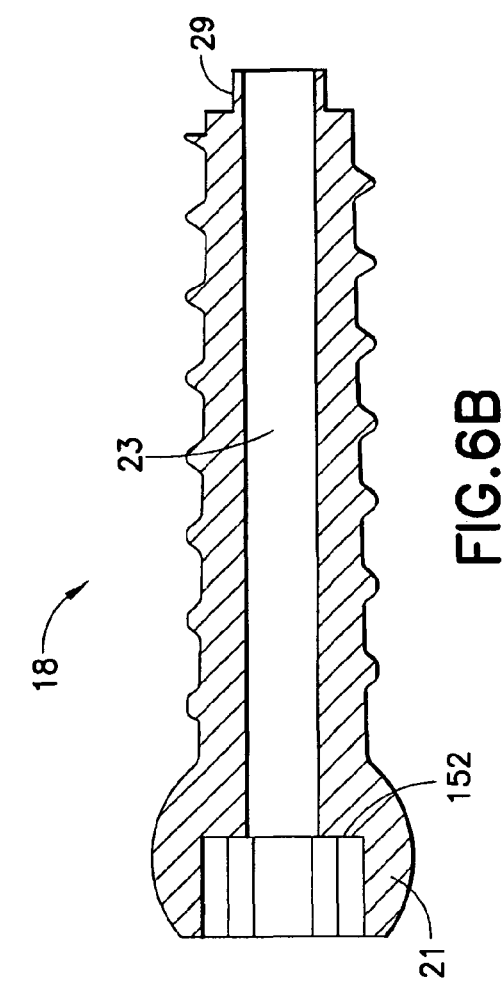
Figure 6C:
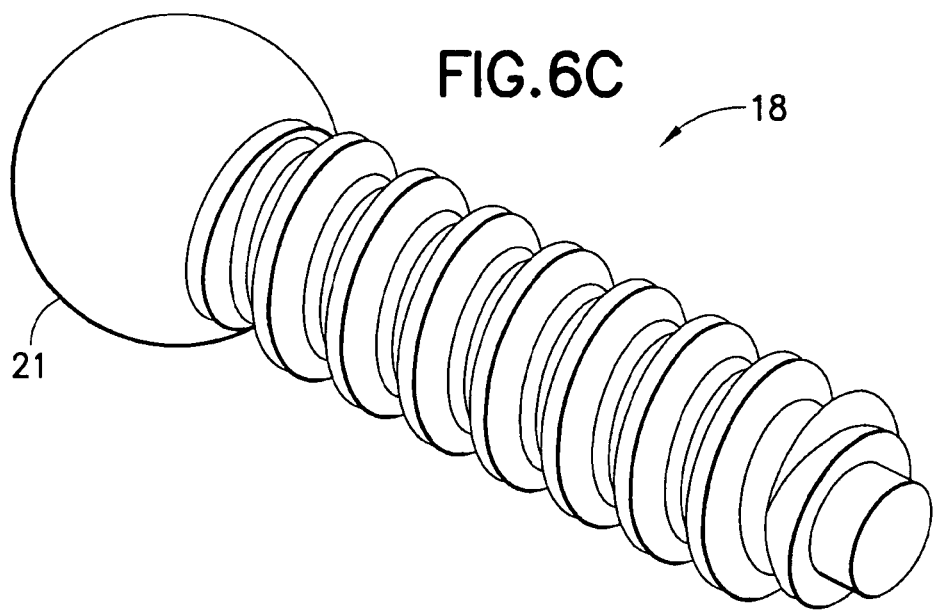
Figure 6D:
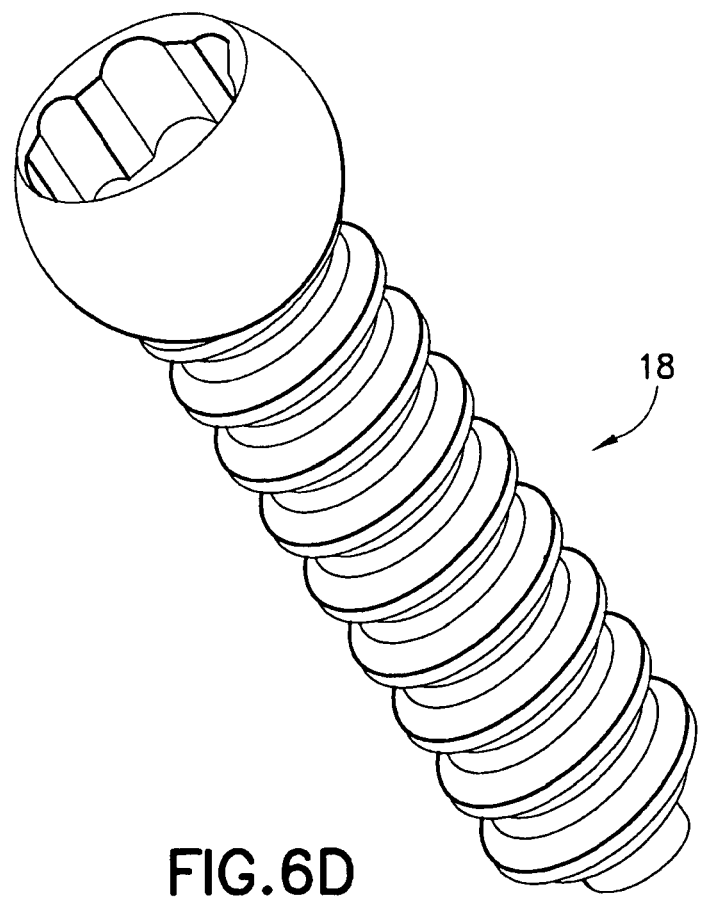
Figure 9:
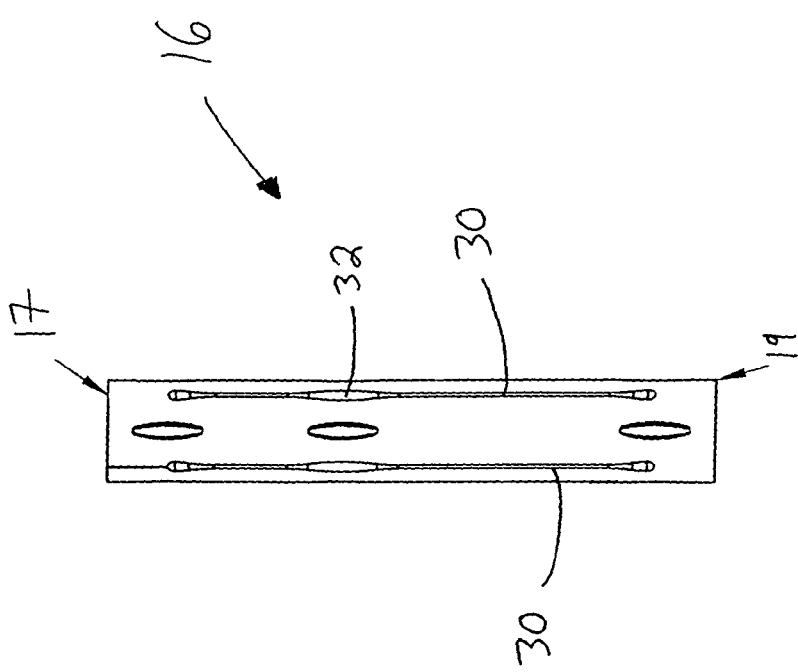
FIG. 9 illustrates a partial view of an embodiment of an anchor region of a bone stabilization device or sub-assembly according to the present disclosure.

Typically, the anchor region 16 includes a plurality of anchoring elements or arms 22 (e.g., four anchoring elements or arms) extending from both anchor element end regions 17, 19. In exemplary embodiments, the anchoring elements or arms 22 are expandable or moveable between a generally axial collapsed state (shown in FIGS. 1 and 2) and a substantially transverse expanded state (FIGS. 3-5). In general, arms 22 are deployable in a direction that is away from the axis 28 of the assembly 10 (e.g., the arms 22 buckle outwardly relative to the longitudinal axis 28 of the device 10 to define the expanded state), and they function to secure and/or stabilize the assembly 10 relative to and/or into bone and/or bone tissue (e.g., spinal bone, cancellous bone, cortical bone, etc.). Additionally, each end region 17, 19 may be sufficiently flexible to bend as needed to accommodate movement between the collapsed and expanded states.

In exemplary embodiments, anchoring elements or arms 22 take the form of substantially flat arms or bands or the like (e.g., in the collapsed state), although the present disclosure is not limited thereto. Rather, anchoring elements or arms 22 may take the form of round wires, filaments, or any other suitable structures (e.g., expanding and/or collapsing members) capable of assuming the collapsed and expanded states. Anchoring elements or arms 22 may take a variety of forms, shapes and/or sizes. It is noted that as used in this specification, the term "anchoring element" or "arm" refers to any structure that performs an anchoring function and/or expanding/collapsing function, and may have different forms, shapes, and configurations in different embodiments. Thus, the term "anchoring element" or "arm" should not be limited to structure having an elongated shape, and may refer to a structure or that has many other shapes.

Anchor region 16 may be substantially linear and/or substantially aligned with the longitudinal axis 28 of the device 10 when the plurality of arms 22 are in the collapsed state, although the present disclosure is not limited thereto. In one embodiment, the anchor region 16 in the collapsed state has a substantially uniform diameter (e.g., outer diameter). The outer diameter of the second body region 15 (e.g., the outer diameter of the second body end region 13) and/or the outer diameter of the first body region 18 may be substantially the same as the outer diameter of the anchor region 16 in the collapsed state. For example, the second body region 15 (and/or the first body region 18) may have a substantially uniform outer diameter, and the diameter of the second body region 15 (and/or the first body region 18) may be substantially the same as the diameter of the anchor region 16 in the collapsed state. In another embodiment and as depicted in FIGS. 25A-25B, the external surface of the anchor region 16 may include threads or thread-like features or the like (instead of being a substantially smooth surface). For example, the external surface of the anchor region 16 may include threads or thread-like features, the threads of region 16 being a substantial continuation of the threads of region 18 when the anchor region 16 is in the collapsed state, so that regions 16 and 18 of device 10 behave as a screw having external threads or the like in the collapsed state (e.g., FIGS. 25A-25B).

In exemplary embodiments and as shown in FIGS. 1-2, the anchoring elements or arms 22 may be formed by fabricating a plurality of slots, slits or cuts 30 or the like in the anchoring region 16. Each slot or slit 30 may or may not extend substantially to the end of the anchor element end regions 17, 19 (e.g., each slot 30 may or may not extend substantially to the proximal end of the first anchor element end region 17, or to the distal end of the second anchor element end region 19). As depicted in FIGS. 1-5, the anchor region 16 may further include hinge regions 32. In one embodiment, each anchoring element or arm 22 includes at least one hinge region 32. For example, the hinge regions 32 may be scored, thinned, slotted, buckled, hinged and/or weak regions 32 of each anchoring element or arm 22 which are configured and dimensioned to provide a hinge or buckle or bend in a predetermined manner (e.g., to buckle or bend outwardly relative to the longitudinal axis 28 of the device 10 to define the expanded state) when the anchoring elements or arms 22 are being deployed. For example and as shown in FIG. 3, the second body region 15 may be displaced linearly, i.e., towards the first body region 18, thereby causing the hinge regions 32 to buckle or bend and move substantially transversely outward until they achieve the expanded state. In exemplary embodiments, when the arms 22 are being deployed during use, each arm 22 will buckle or bend at the hinge regions 32. Thus, the hinge regions 32 allow the arms 22 to be bent or buckled in a predictable manner. In other embodiments, the assembly 10 does not include the hinge regions 32.

In alternative embodiments, the anchoring elements or arms 22 may be fabricated or constructed using various other techniques. For example the arms 22 may be individually fabricated or constructed, and then the arms 22 may be secured and/or coupled to the assembly 10 (e.g., the first anchor element end region 17 of each arm 22 may be secured and/or coupled to the first body region 18, and/or the second anchor element end region 19 of each arm 22 may be secured and/or coupled to the second body region 15).

In exemplary embodiments and as shown in FIG. 6, the first body region 18 includes a first channel, lumen or cavity 23 (e.g., central lumen) formed or fabricated in first body region 18. In one embodiment, the first channel 23 is a tubular channel or lumen, with a circular cross-section, although the present disclosure is not limited thereto. Rather, the first channel 23 may take a variety of forms and/or cross-sections. As shown in FIG. 6, the first channel 23 may extend substantially through the interior of the first body region 18.

In general and as shown in FIGS. 1-6 and 8, the first channel 23 is configured and dimensioned to at least partially receive, house and/or have disposed within an actuator 24. In an exemplary embodiment, the actuator 24 may take the form of an elongate actuator member 24. For example, the actuator 24 may be a deployment rod (e.g., a solid, semi-solid or hollow rod), a tubular or tubular-like member, or a control wire or the like, although the present disclosure is not limited thereto. Alternatively, other variations may be provided for the actuator 24, such as mechanical, hydraulic, or pneumatic actuators, as appreciated by those skilled in the art. In an exemplary embodiment, actuator 24 is removable from the device 10. For example, actuator 24 may take the form of a removable deployment rod or control wire or the like (or any other suitable form) that may be inserted into device 10 to deploy arms 22, but then removable actuator 24 is then removed from device 10 after actuation/deployment of arms 22. In such embodiments, after actuator 24 has been utilized to deploy arms 22 and subsequently removed from device 10, the device 10 may then be locked in the deployed position by inserting a separate locking member (e.g., an elongate member, either threaded or non-threaded, similar to elongate member 24) into first lumen 23 and/or second lumen 27 of device 10. For example, the separate locking member (e.g., similar to elongate member 24) inserted into device 10 after deployment of arms 22 may be configured and dimensioned to prevent the second body region 15 from moving distally after arms 22 have been deployed, thereby locking the deployed arms in their deployed positions. In other words, elongate member 24 or the like may be utilized as a locking member after a separate and removable actuator (e.g., deployment rod or control wire or the like) has been utilized to deploy arms 22.

In an exemplary embodiment and as shown in FIG. 8, the actuator 24 has a proximal end 140 which may include an engagement head 25, and a distal end 142 which may include external and/or internal threads. The proximal end 140 of the actuator 24 may also include external and/or internal threads. The engagement head 25 may be generally "T" shaped or the like, although the present disclosure is not limited thereto. The engagement head 25 may be utilized and/or engaged with a deployment and/or undeployment device to deploy/undeploy the anchoring elements or arms 22 of the device 10, as described below.

In an exemplary embodiment and as shown in FIG. 8, the actuator 24 and/or engagement head 25 may also include at least one protrusion 146 or the like having a bottom surface 147.

In general, the cross-sectional dimension of the at least one protrusion 146 is larger than the cross-sectional dimension of the first channel 23. As shown in FIG. 1, such configuration generally prevents the actuator 24 from advancing past the desired amount or distance distally within the first channel 23 and/or within the second channel 27 of the device 10. For example and as depicted in FIGS. 1, 6 and 8, the bottom surface 147 of the at least one protrusion 146 will abut against a proximal face 152 of the first body region 18 (e.g., an inner proximal face 152 of the head 21), thereby preventing the actuator 24 from advancing past the desired amount or distance distally within the device 10. In general, such configuration also allows the engagement head 25 of the actuator 24 to be spaced a desired distance from the proximal surface 152 of the first body region 18, so that a deployment/undeployment device may be engaged with and/or coupled/connected to the engagement head 25, to thereby allow the deployment/undeployment device to deploy/undeploy the anchoring elements or arms 22 (e.g., to allow a deployment/undeployment device to be positioned between the engagement head and the proximal surface 152 to thereby allow the deployment/undeployment device to pull the engagement head 25 proximally (about 1 mm to about 8 mm, and preferably about 2 mm) to deploy the anchoring elements or arms 22).

In exemplary embodiments and as depicted in FIG. 7, the second body region 15 (e.g., the inner region 11 of the second body region 15) includes a second channel, lumen or cavity 27 formed or fabricated therein. In one embodiment, the second channel 27 is a tubular channel or lumen, with a circular cross-section, although the present disclosure is not limited thereto. Rather, the second channel 27 may take a variety of forms and/or cross-sections. As shown in FIG. 7, the second channel 27 extends partially through the interior of the second body region 15 (e.g., partially through the interior of the inner region 11 of the second body region 15). In an alternative embodiment, the second channel 27 may extend substantially through the interior of the second body region 15. In general and as shown in FIGS. 1-5 and 7-8, the second channel 27 is configured and dimensioned to at least partially receive, house and/or have disposed within at least a portion of the actuator 24. In exemplary embodiments and as depicted in FIG. 1, at least a portion of the anchor region 16 is also configured and dimensioned to at least partially receive, house and/or have disposed within at least a portion of the actuator 24 (e.g., within a channel, lumen or cavity formed or fabricated within the anchor region 16).

As shown in FIGS. 1-5 and 7, actuator 24 may be detachably/releasably secured and/or coupled to second body region 15 (e.g., to inner region 11 of second body region 15). For example, actuator 24 may extend into second channel 27 of inner region 11 of second body region 15 and be detachably/releasably secured and/or coupled thereto by various means. In one embodiment, at least a portion of the distal end 142 of actuator 24 includes a threaded region (e.g., external threads or the like), and at least a portion of the proximal end 143 of the inner region 11 includes a correspondingly threaded region (e.g., internal threads or the like of second channel 27), and actuator 24 and inner region 11 may be threadably coupled and/or in communication with one another. Such configurations may also allow the length of actuator 24 to be adjusted by rotating/turning actuator 24 and/or second body end region 15.

Figure 26:
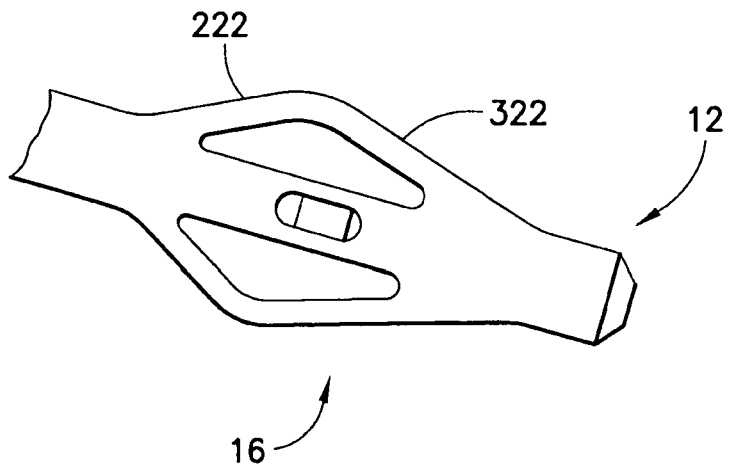
FIGS. 26-27 illustrate alternative embodiments of the arms of a deployed anchor region of a bone stabilization device or assembly according to the present disclosure.
Figure 27:
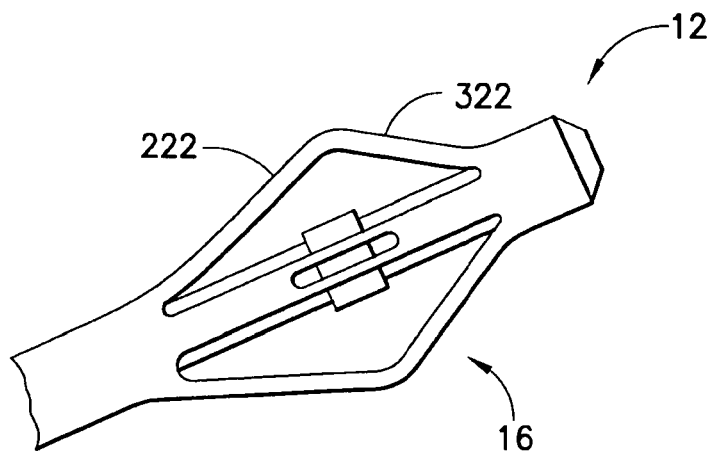

In exemplary embodiments and as shown in FIGS. 1-5, deployment of the anchoring elements or arms 22 of the anchor region 16 may involve proximal movement (e.g., about 1 mm to about 8 mm, and preferably about 2 mm) of the actuator 24 relative to the first body region 18, which causes outward deflection of the arms 22 in a predetermined manner (e.g., the arms 22 buckle or bend at the hinge regions 32 outwardly relative to the longitudinal axis 28 of the device 10 to define the expanded state). At this stage, the arms 22 are deployed, but unlocked, as shown in FIG. 3. FIGS. 23A-23F illustrate various alternative embodiments of the arms 22 of a deployed anchor region 16 of a bone stabilization device or assembly 10 according to the present disclosure. In addition, FIGS. 26-27 depict embodiments where the arms 22 of anchor region 16 are deployed in an asymmetrical form (instead of a being deployed in a substantially rhomboid form). For example and as shown in FIG. 26, the proximal arms 222 of the anchor region 16 may be shorter in length than the distal arms 322. Alternatively and as shown in FIG. 27, the proximal arms 222 of the anchor region 16 may be longer in length than the distal arms 322.

In alternative embodiments and as shown in FIGS. 24A-24D, the bone stabilization device or assembly 10 may include more than one anchor region 16. For example, the arms 22 of anchor regions 16 may be similar to the anchor region 16 of FIG. 4, where the arms or longitudinal elements 22 are transversally expanded bucking outward relative to the longitudinal axis 28. Alternatively, at least one of the anchor regions 16 may be similar to the anchor region 16 of FIG. 20, where the arms 22 are deployed expanding radially outward, or the anchor regions 16 can be of other kind, for example, similar to an accordion-like type or the like (e.g., or similar to the arms 22 of regions 16 as depicted in FIGS. 23A-23F). Any combinations of the different types of arms 22 at the different anchor regions sites 16 may be utilized with the bone stabilization device or assembly 10.

Figure 24A:
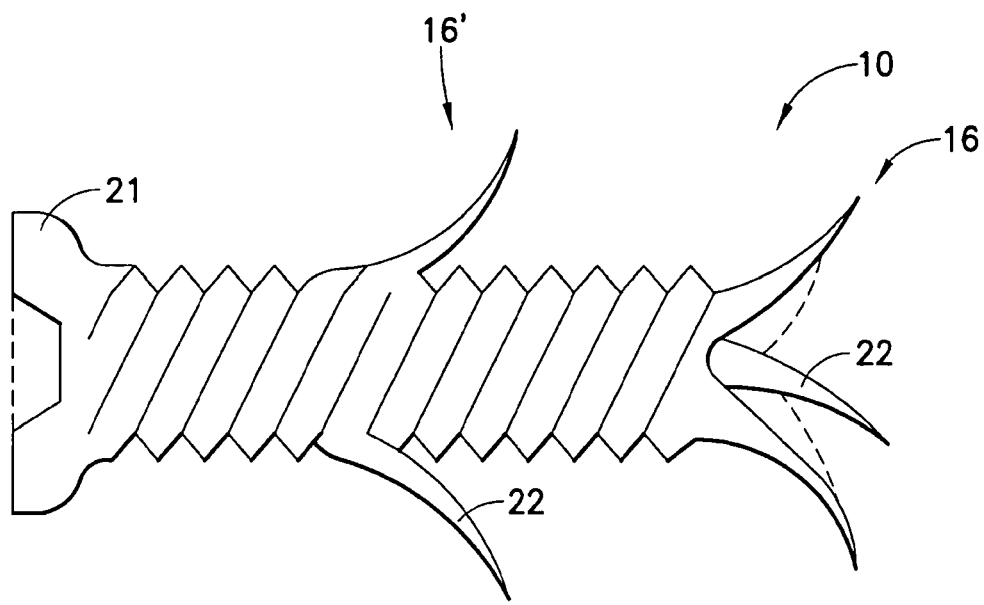
FIGS. 24A-24D illustrate various alternative embodiments of bone stabilization devices or assemblies.
Figure 24B:
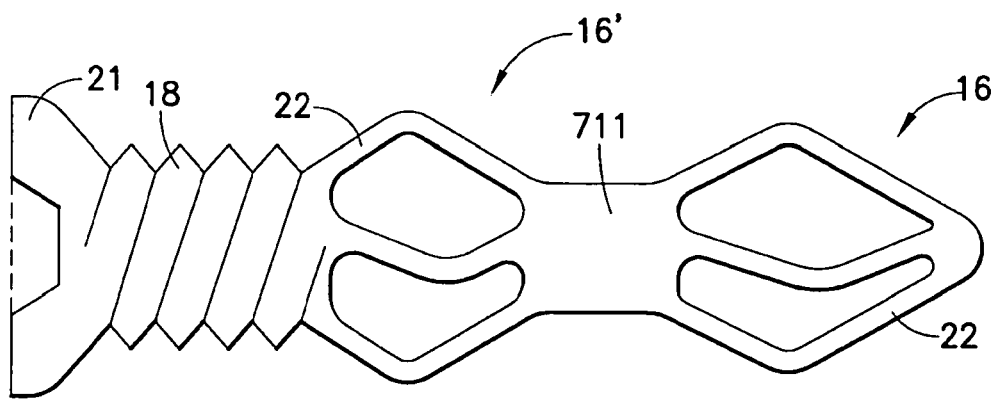
Figure 24C:
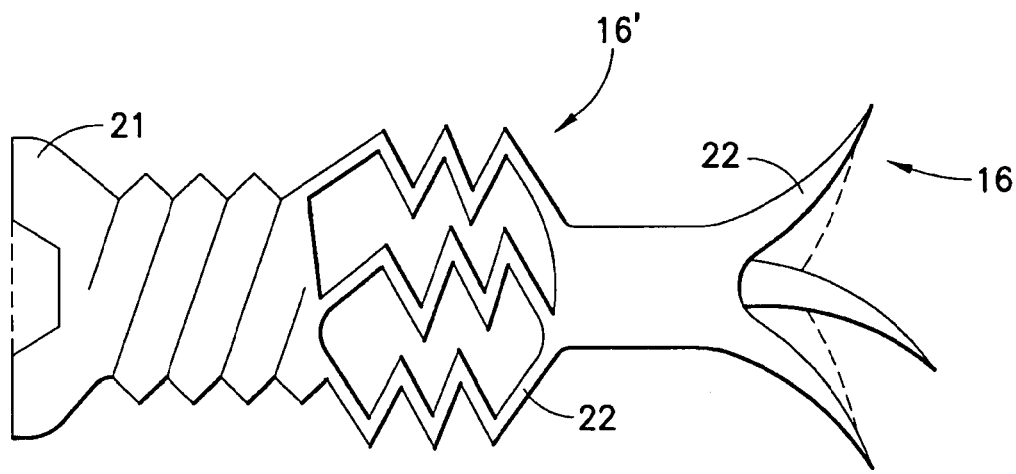
Figure 24D:
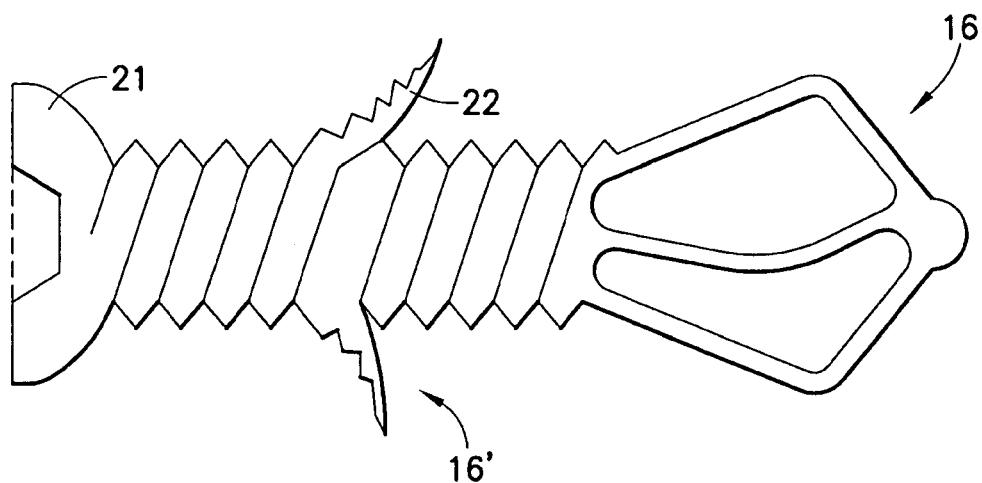

For example, one site of a first anchor region 16 may be located near the distal tip of device 10, as shown in FIGS. 4 and 20, and a second anchor region 16 may be located near the proximal tip/end of the same device 10, or at any region/location between the head 21 of the device 10 and its distal portion 12. In one embodiment, the threaded region 18 is located between the head 21 and the second (proximal) anchor region 16' (FIG. 24B). The device 10 may have a substantially smooth section 711 without threads or the like, between the first and the second anchor regions 16, 16', allowing adjustment of the length of the device 10. In an exemplary embodiment, for the adjustment in length of the device 10, the second (proximal) anchor region 16' between the threaded section 18 and the first (distal) anchor region 16 may be of the type of anchor region 16 as shown in FIG. 4, or the second (proximal) anchor region 16' may be any accordion-like type or region 16 or the like.

For example, adjustment of the length of device 10 by the expansion of the second (proximal) anchor region 16' may be helpful when device 10 is used in a long bone transversally to its long axis, when the distal expansion is outside the bone (or in the distal section of a fractured bone segment) and the second (proximal) anchor region 16' is expanded inside the bone, near the area of the head 21 of device 10, producing compression between the head 21 of the device 10 and the first (distal) anchor region 16. Also, adjustment of the length of device 10 is useful when the device 10 is used for the attachment of plates or other devices to bone, thereby allowing the use of one size in length of device 10 suiting different bone diameters and/or shapes. In other embodiments, the threads of device 10 may be located in any section of device 10, including, but not limited to, on the surface of the first and/or second anchor regions 16.

In an exemplary embodiment, deployment of the anchoring elements or arms 22 of the anchor region 16 involves proximal movement of the actuator 24, thereby causing the second body region 15 to be displaced linearly, i.e., towards the first body region 18, which thereby causes the arms 22 to buckle or bend (e.g., at the hinge regions 32) and move substantially transversely outward until they achieve the expanded state. For example, the actuator 24 may be pulled or moved proximally to deploy the arms 22. In exemplary embodiments, the actuator 24 may be moved proximally manually (e.g., pulled or moved by hand and/or by utilizing a deployment device engaged with the actuator 24). Alternatively, the actuator 24 may be moved proximally utilizing various other techniques, such as, for example, rotational, mechanical, hydraulic, and/or pneumatic movement and/or actuators.

In exemplary embodiments, the proximal movement of actuator 24 which causes second body region 15 to be displaced linearly, i.e., towards first body region 18, creates a compression force on anchor region 16 that bends/buckles/deploys arms 22. In one embodiment, arms 22 may be configured to bend elastically. In such cases, in the absence of the pulling/moving force that is generally asserted at the proximal end 14, arms 22 will elastically bend back towards their un-deployed positions. Alternatively, arms 22 may be configured to bend or buckle inelastically (e.g., as in a plastic deformation). In such cases, arms 22 may remain deployed when the pulling/moving force asserted at the proximal end 14 is removed. In any of the embodiments described herein, anchoring elements or arms 22 may be undeployed after being deployed (e.g., via elastic or plastic deformation), and assembly 10 may be removed from the bone and/or bone tissue when desired (e.g., once arms 22 are undeployed after being deployed).

Figure 35A:
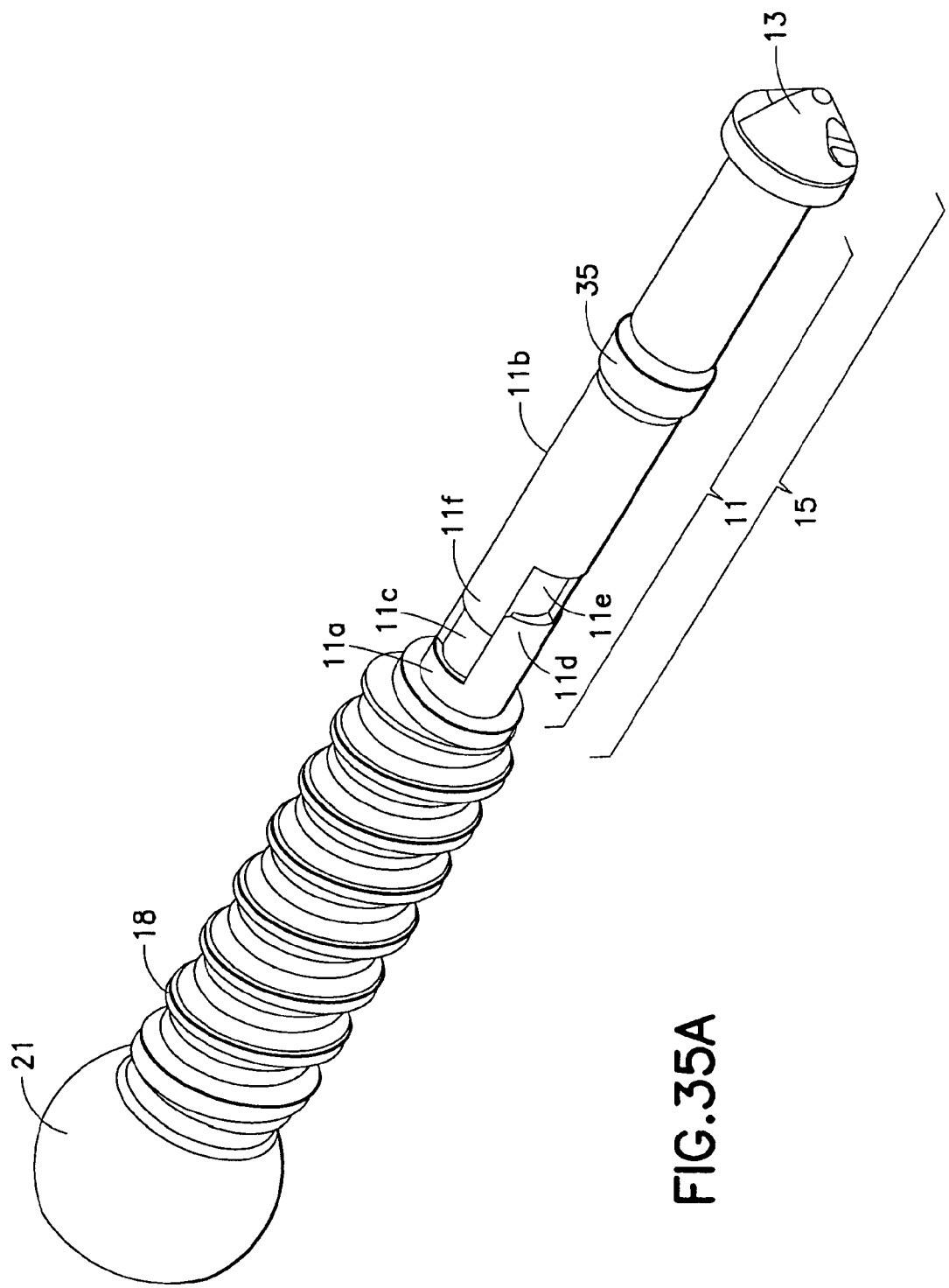
FIG. 35A is a side perspective view of another embodiment of a bone stabilization device or assembly in a non-deployed state and with anchor region removed.
Figure 35B:
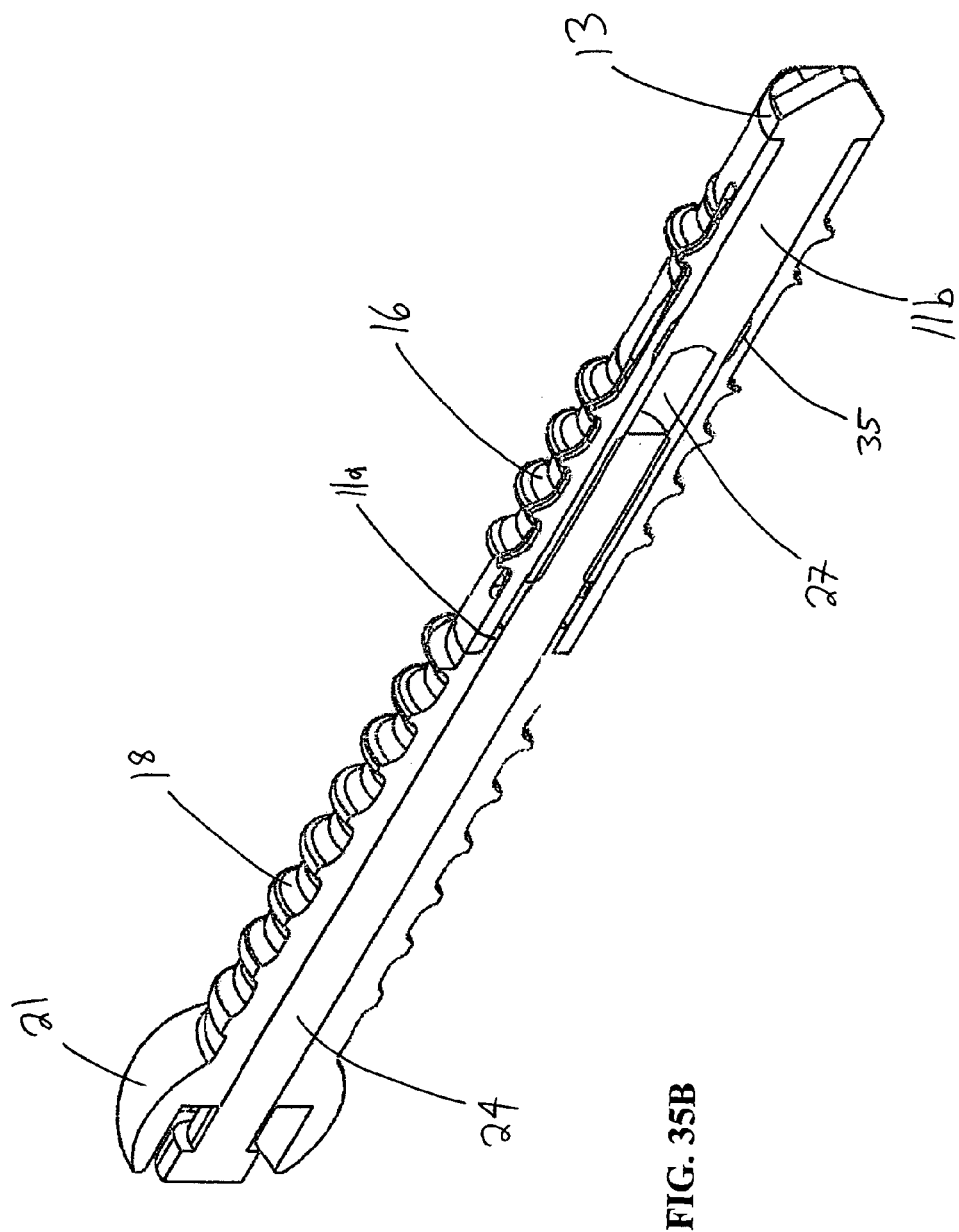
FIG. 35B is a cross-sectional side perspective view of the device of FIG. 35A, with anchor region positioned on the device.
Figure 35C:
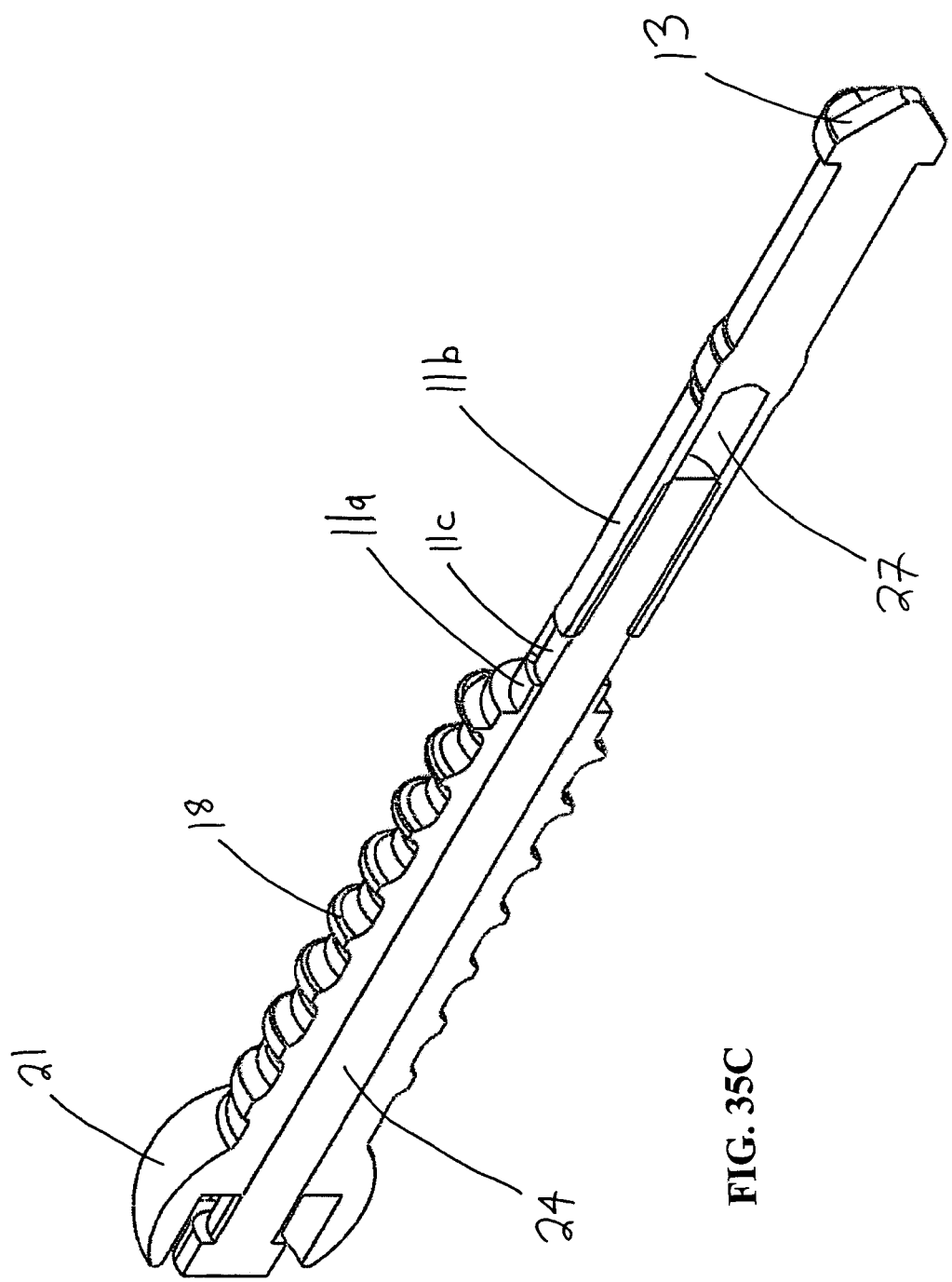
FIG. 35C is a cross-sectional side perspective view of the device of FIG. 35A, with anchor region removed.
Figure 36A:
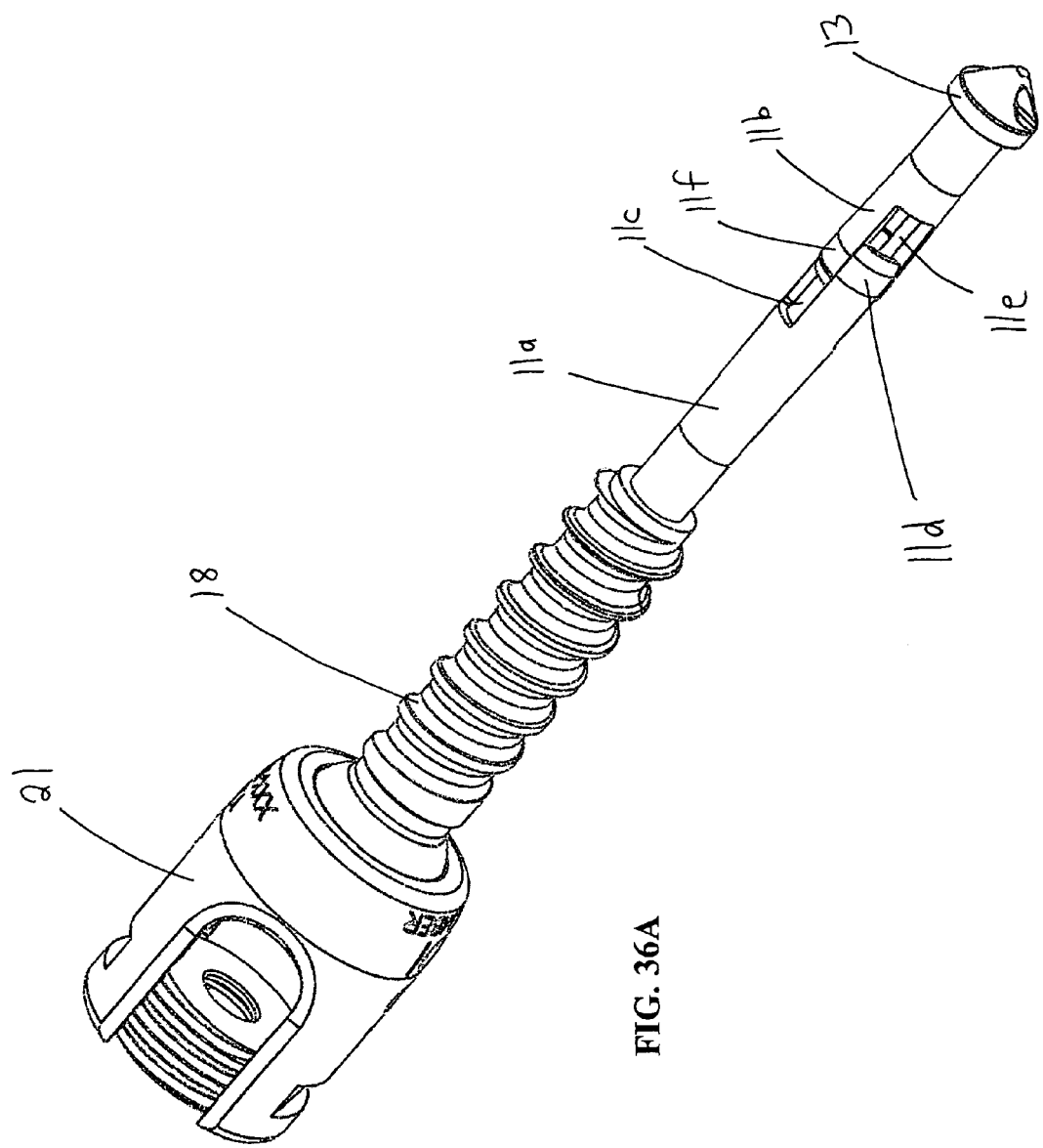
FIG. 36A is a side perspective view of another embodiment of a bone stabilization device or assembly in a non-deployed state and with anchor region removed.
Figure 36B:
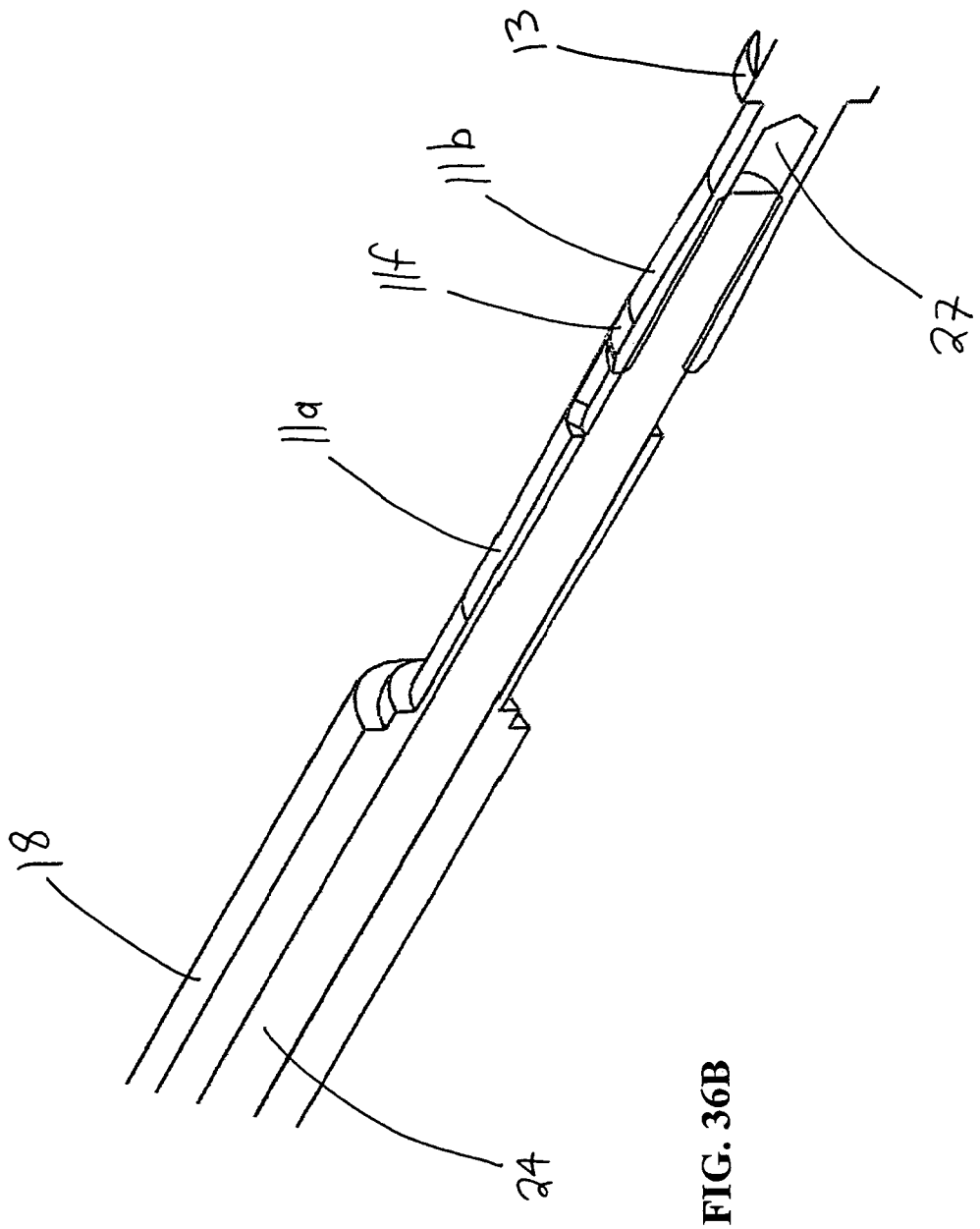
FIG. 36B is a cross-sectional side perspective view of the device of FIG. 36A, with anchor region removed.

In alternative embodiments and as shown in FIGS. 35-38, inner region 11 of second body region 15 of device 10 includes a first inner region 11a and a second inner region 11b. In general, first inner region 11a is engaged with or coupled/attached to second inner region 11b. In one embodiment, first inner region 11a is fittingly engaged with second inner region 11b. For example and as shown in FIGS. 35-36, first inner region 11a includes at least one recess region 11c and at least one protrusion 11d, and second inner region 11b includes at least one recess region 11e and at least one protrusion 11f, with protrusion 11d fittingly engaged with at least a portion of recess region 11e and with protrusion 11f fittingly engaged with at least a portion of recess region 11c. In exemplary embodiments, there are two protrusions 11d of first inner region 11a, with each protrusion 11d being fittingly engaged with at least a portion of one of two recess regions 11c of second inner region 11b, and there are two protrusions 11f of second inner region 11b, with each protrusion 11f being fittingly engaged with at least a portion of one of two recess regions 11c of first inner region 11a.

Figure 37A:
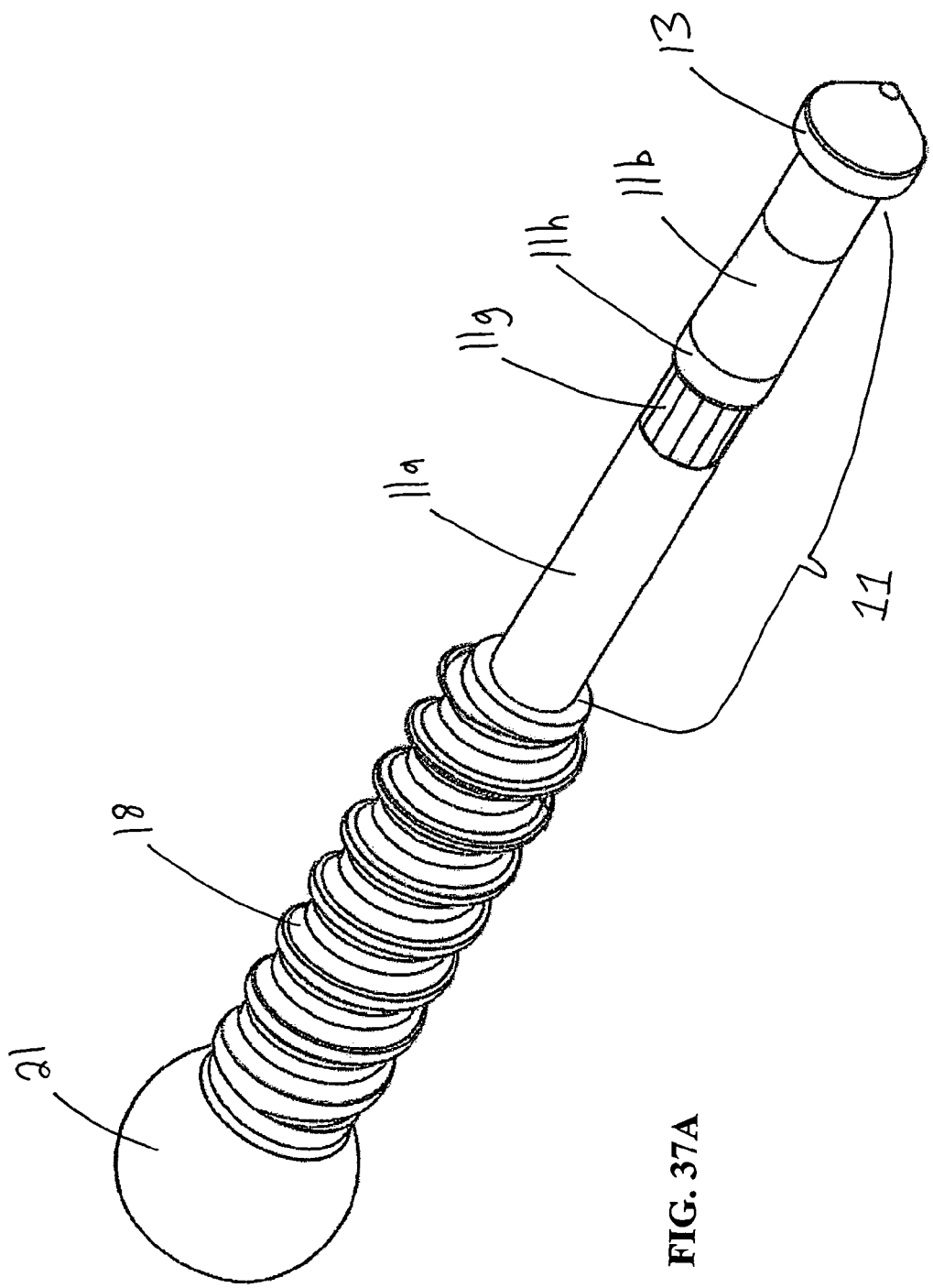
FIG. 37A is a side perspective view of another embodiment of a bone stabilization device or assembly in a non-deployed state and with anchor region removed.
Figure 37B:
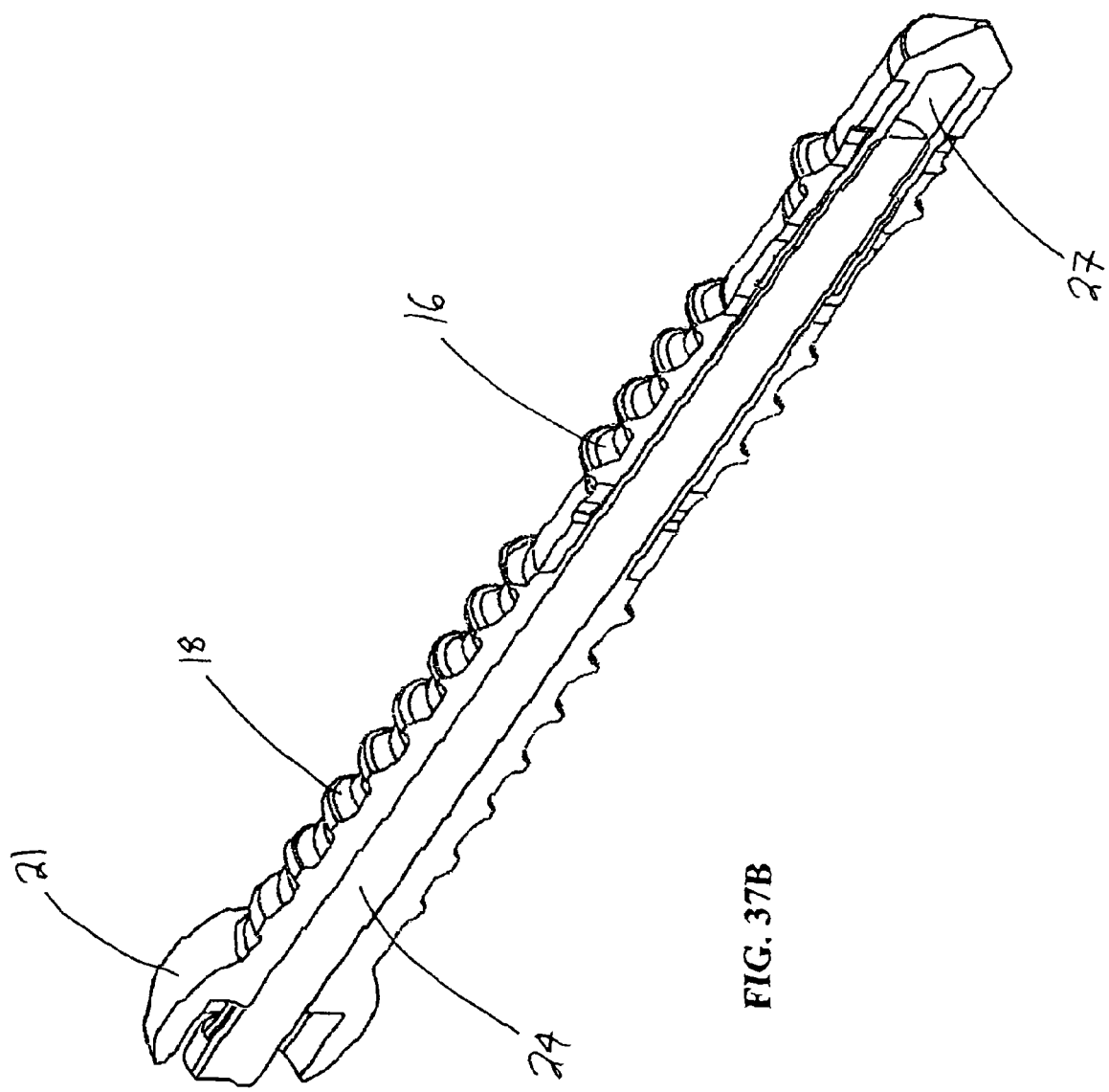
FIG. 37B is a cross-sectional side perspective view of the device of FIG. 37A, with anchor region positioned on the device.
Figure 37C:
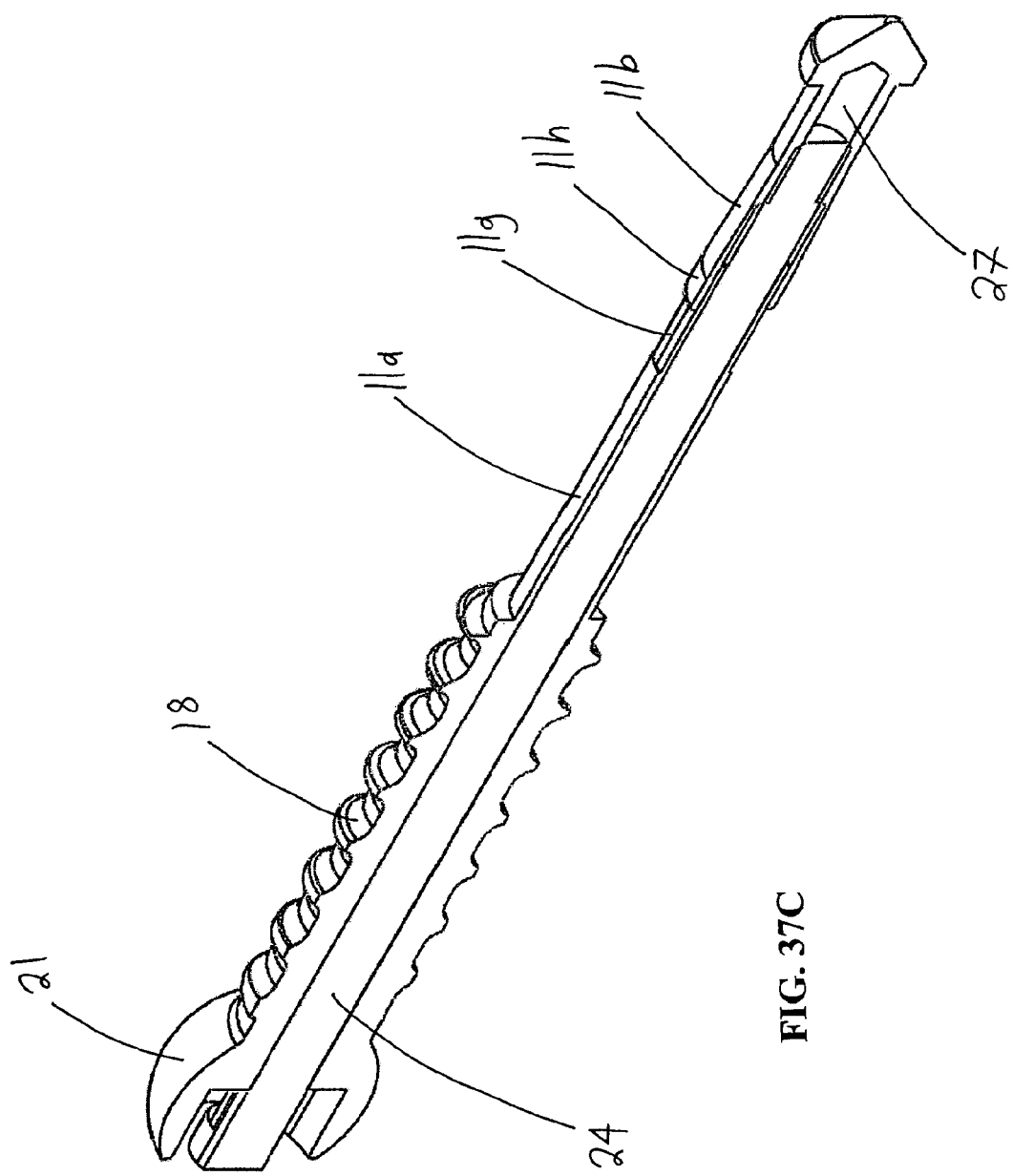
FIG. 37C is a cross-sectional side perspective view of the device of FIG. 37A, with anchor region removed.
Figure 38A:
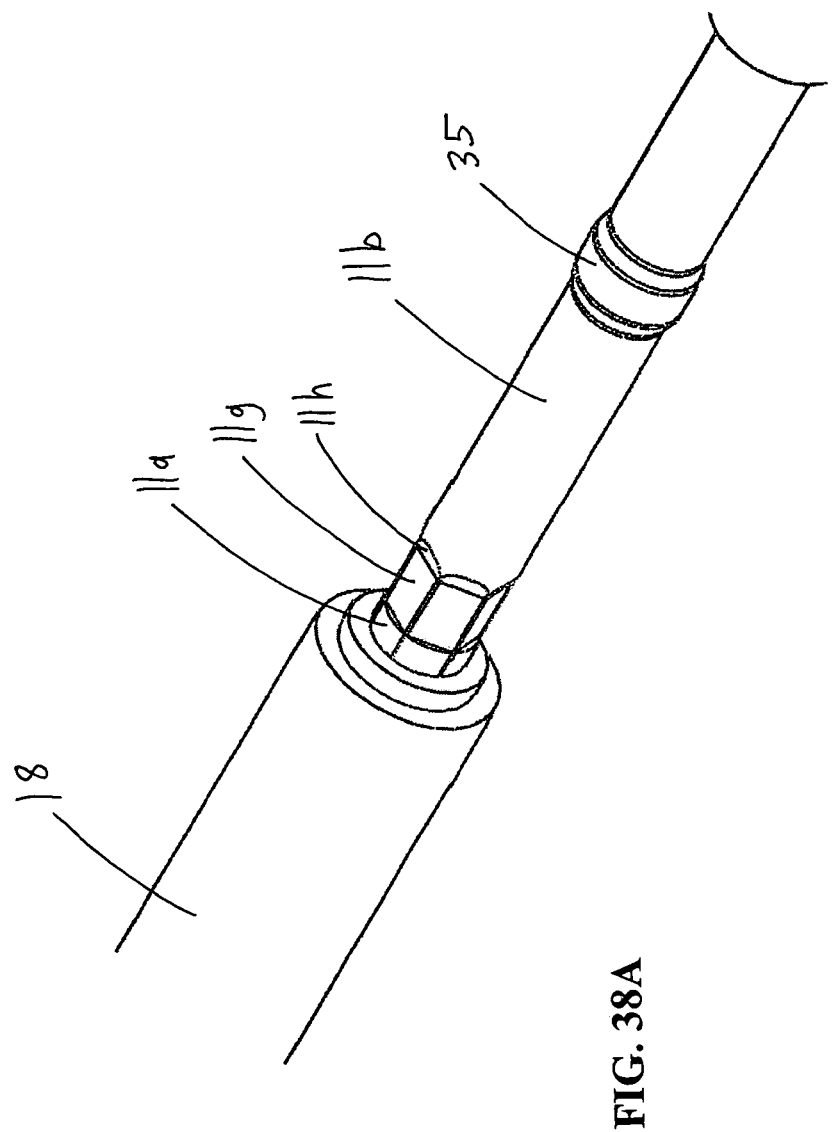
FIG. 38A is a side perspective view of another embodiment of a bone stabilization device or assembly in a non-deployed state and with anchor region removed.
Figure 38B:
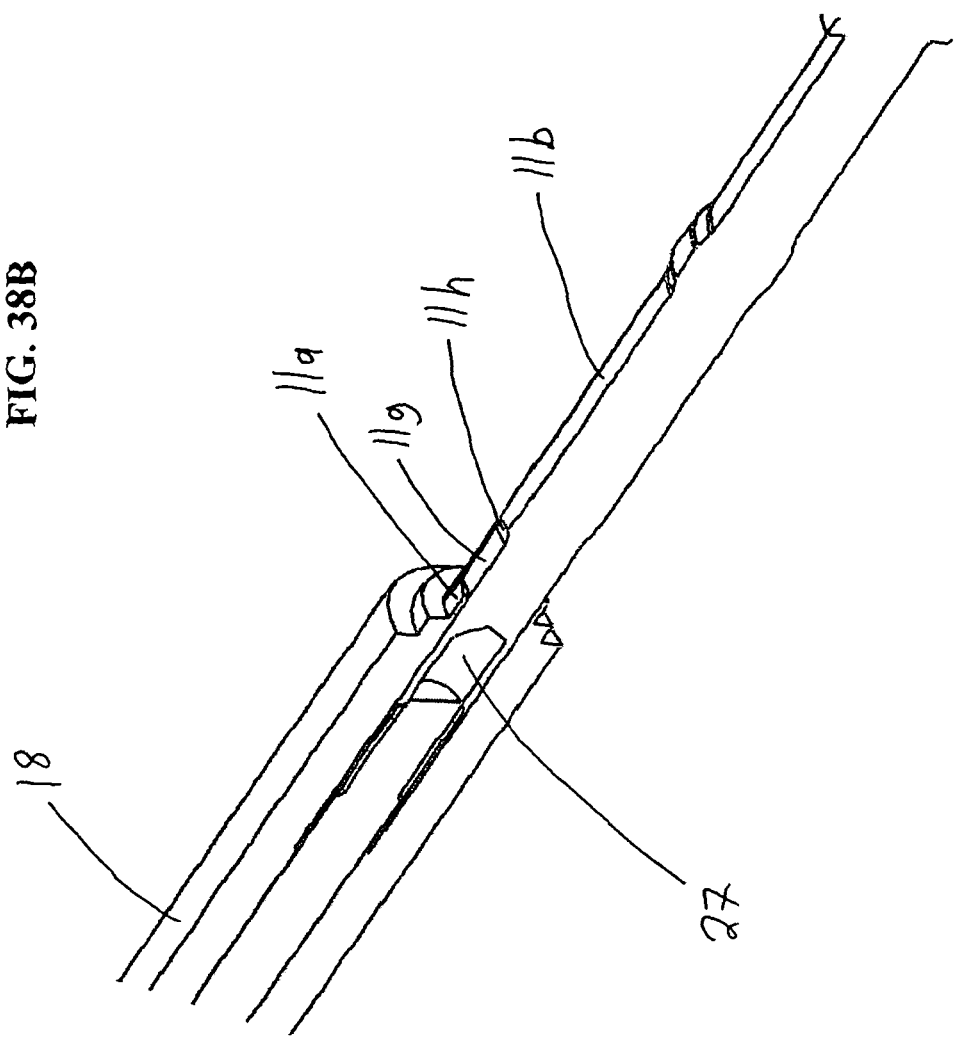
FIG. 38B is a cross-sectional side perspective view of the device of FIG. 38A, with anchor region removed.

In another embodiment and as shown in FIGS. 37-38, first inner region 11a includes a first fitted region 11g, second inner region 11b includes a second fitted region 11h, with at least a portion of first fitted region 11g being fittingly engaged with second fitted region 11h.

In general, when first inner region 11a is engaged with or coupled/attached to second inner region 11b, regions 11a and/or 11b are configured and dimensioned to be displaced or moved proximally or distally (e.g., linearly) with respect to one another (e.g., region 11b is allowed to be moved or displaced linearly (proximally or distally) with respect to region 11a, or vice versa). Typically, when regions 11a and 11b are engaged or coupled together, regions 11a and 11b are prevented from substantially rotating axially (e.g., they are prevented from rotating axially together or with respect to one another). In exemplary embodiments, first inner region 11a is connected, mated, coupled and/or attached to first body region 18. In one embodiment, at least a portion of first inner region 11a is integrally formed from first body region 18.

As such, since engaged or coupled regions 11a and 11b are typically configured and dimensioned to be prevented from rotating axially, this thereby substantially prevents arms 22 of anchor region 16 (substantially positioned over inner region 11, as discussed above) from twisting and/or bending when device 10 is being inserted or removed. For example, if the device 10 and/or tip 13 encounters hard bone or bone tissue when a user begins to insert and/or screw device 10 into bone or bone tissue, the anti-twisting and/or anti-bending features of regions 11a and 11b (e.g., via the non-rotational features of engaged regions 11a and 11b) substantially prevents the arms 22 of anchor region 16 from being twisted or bent during insertion and/or removal of device 10 (even into/out of hard bone/bone tissue), thereby providing a significant commercial advantage as a result.

In general and as shown in FIG. 35, second channel 27 of second body region 15 is configured and dimensioned to at least partially, receive, house, and/or have disposed within at least a portion of actuator 24. In exemplary embodiments, actuator 24 is detachably/releasably secured and/or coupled to second inner region 11b (and/or to first inner region 11a). Thus, deployment of arms 22 of anchor region 16 typically involves proximal movement of actuator 24, thereby causing second inner region 11b to be displaced proximally and/or linearly, i.e., towards first inner region 11a and/or first body region 18, which thereby causes arms 22 to buckle/bend and move substantially transversely outward until they achieve the expanded state.

Arms 22 may be undeployed after being deployed (e.g., by distal movement of actuator 24 causing second inner region 11b to be displaced or moved linearly away from first inner region 11a) and assembly 10 may be removed from the bone and/or bone tissue when desired.

In exemplary embodiments and as shown in FIGS. 35-38, the fitted engagement of regions 11a and 11b allows for the linear displacement of region 11b for the deployment/undeployment of arms 22, while also preventing the arms 22 from being twisted or bent during insertion/removal of device 10, as discussed above.

In exemplary embodiments and as illustrated in FIGS. 2-5 and 10, a receiver member 20 may be coupled, connected and/or secured (e.g., detachably coupled) to device 10. In one embodiment, receiver member 20 is a cylindrical-like receiver member for receiving head 21 of first body region 18. In general, head 21 has a generally circular or spherical shape, which may allow head 21 to sit within receiver member 20, and rotate in any direction relative to receiver member 20. Receiver member 20 may have inner threads 100 at or near the proximal end 102 of the receiver member 20. The distal end 104 of receiver member 20 may be tapered slightly inward, which may prevent head 21 from moving out of the lumen 26 of the receiver member 21, while allowing head 21 to rotate relative to the receiver member 20.

Figure 29A:
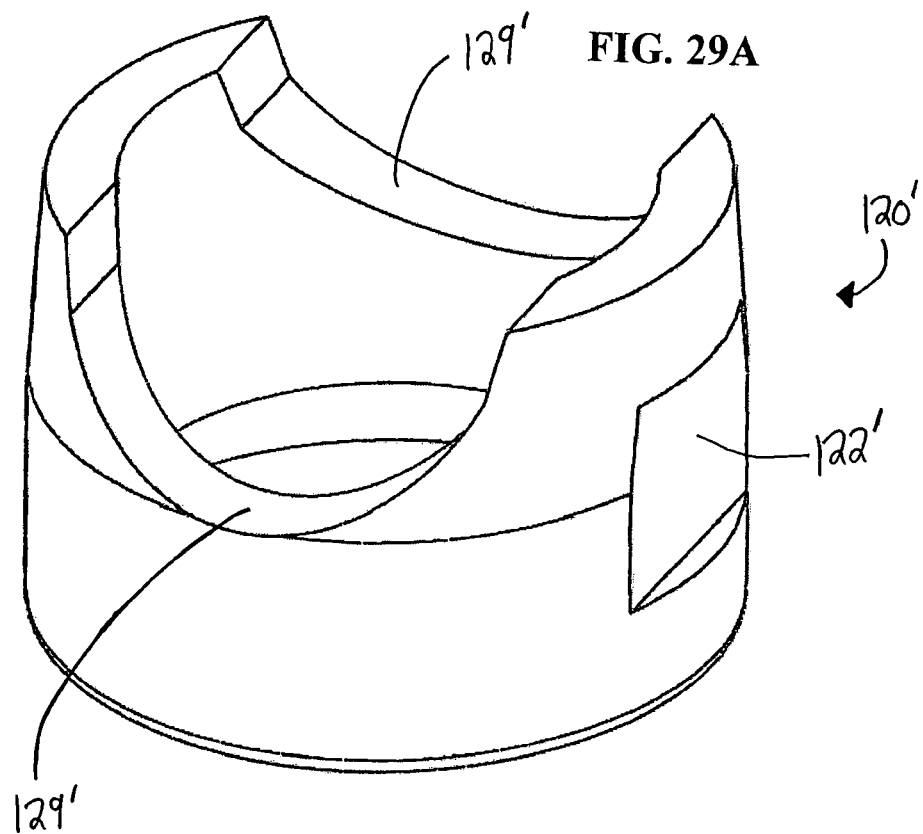
FIGS. 29A-29B depict another embodiment of a secure ring of a bone stabilization device or assembly according to the present disclosure.
Figure 29B:
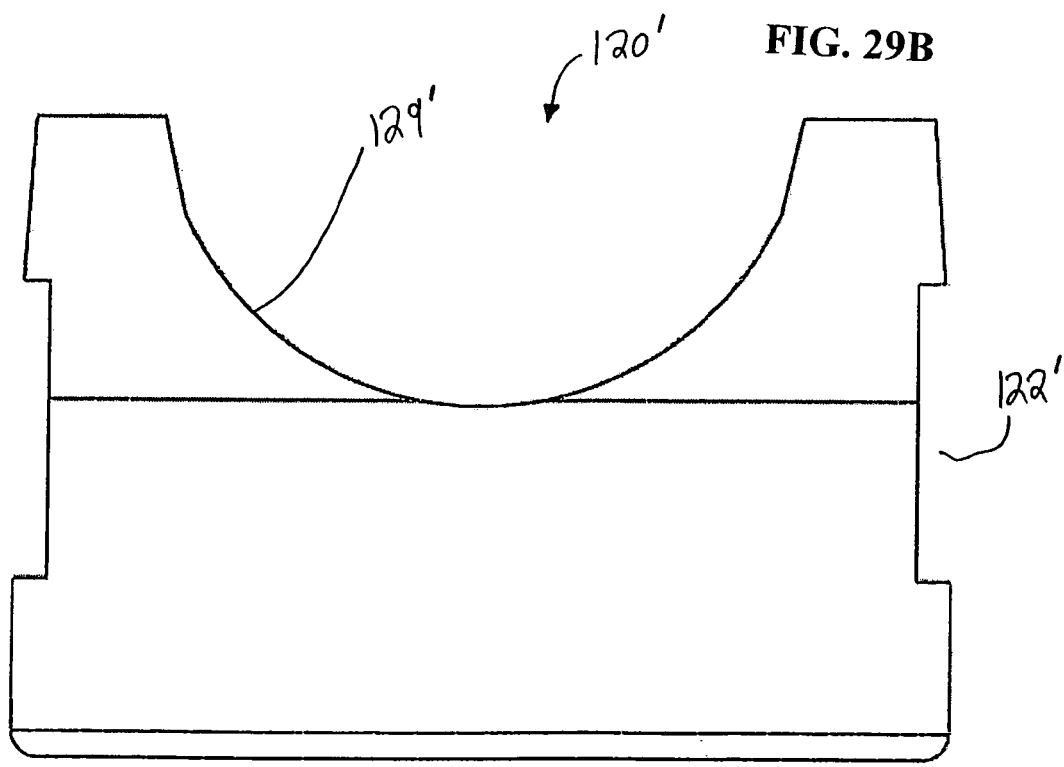

With reference to FIGS. 2-5 and 11, assembly 10 may also include a securing member (e.g., a secure ring) 120. In an exemplary embodiment, secure ring 120 has recesses 122 on opposing sides. The secure ring 120 may be configured and dimensioned to be disposed within the lumen 26 of the receiver member 20. In one embodiment and as shown in FIGS. 11C-11D, secure ring 120 includes substantially flat surfaces 129. Alternatively, secure ring 120' includes substantially rounded or arc-shaped surfaces 129' (FIGS. 29A-29B).

In exemplary embodiments, after deployment of the arms 22 (FIG. 3), the actuator 24 may then be moved distally relative to the second body region 15 (FIG. 4). For example, after deployment of the arms 22 (FIG. 3), the actuator 24 may then be moved distally relative to the second body region 15 by distally screwing/rotating the actuator 24, with the threaded distal end of the actuator 24 advancing relative to the inner threaded region of the second body region 15 (FIG. 4). The secure ring 120 may then be positioned/disposed within the lumen 26 of the receiver member 20 above the first body region 18 (e.g., above the head 21) and above the proximal end of the actuator 24 (e.g., above the engagement head 25). In one embodiment, the secure ring 120 may be positioned/disposed/secured within the lumen 26 of the receiver member 20 above the first body region before the actuator 24 is moved proximally to deploy the arms 22.

After the secure ring 120 is desirably positioned within the receiver member 20, at least one wall portion 124 (e.g., recess 124) of the receiver member 20 is punched, deformed, and/or bent or the like to secure the secure ring 120 in place. For example, a tool or device may be inserted into opposite recesses 124 of the receiver member 20 to bend/punch the respective inner walls of the receiver member 20 inward to secure the secure ring 120 in place. In one embodiment, the deformed/bent wall portions 124 of the receiver member 20 mate/engage with corresponding recesses 122 of the secure ring 120, thereby generally preventing the secure ring 120 from being removed from the receiver member 20.

Figure 12A:
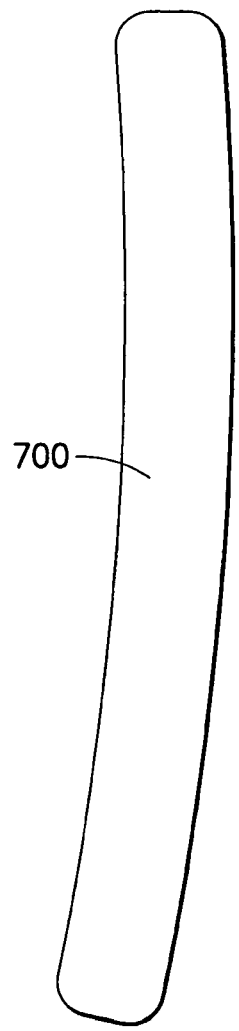
FIGS. 12A-12B illustrate exemplary embodiments of stabilization rods of a bone stabilization device or assembly according to the present disclosure.
Figure 12B:
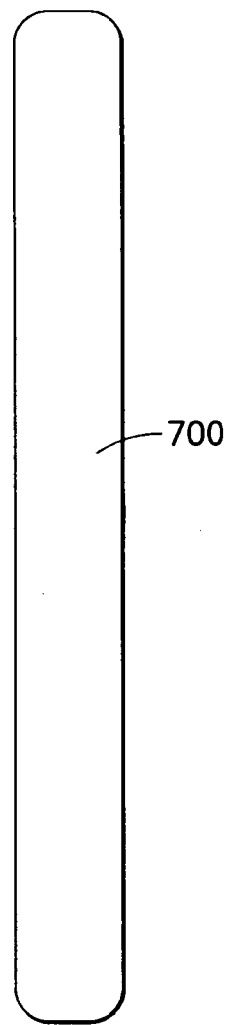
Figure 19:
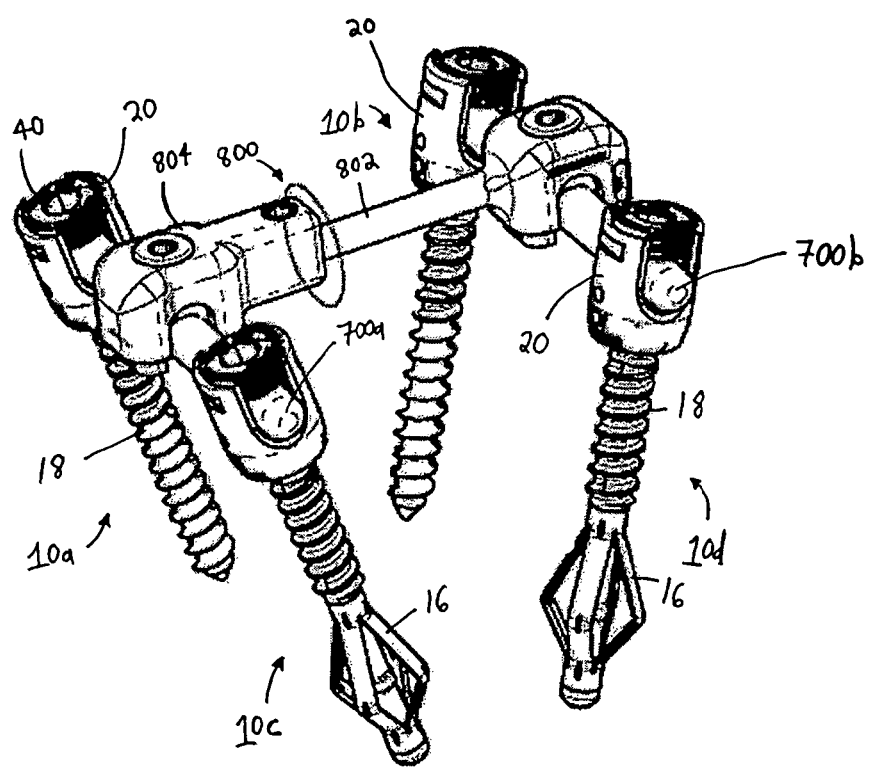
FIG. 19 illustrates an embodiment of using a plurality of bone stabilization devices or assemblies in conjunction with a connecting rod and a cross-connector device or assembly.

In an exemplary embodiment and as depicted in FIGS. 5 and 12, after the arms 22 of the anchor region 16 have been deployed, a rod 700 (e.g., stabilizing or fusion rod) may be positioned in the lumen 26 of the receiver member 20. In general, the rod 700 may be substantially transversely positioned upon the secure ring 120. For example, a rod 700 may be positioned in the lumen 26 of the receiver member 20 to thereby couple the deployed assembly 10 with another deployed assembly 10 (FIG. 19). As shown in FIGS. 5 and 11, the rod 700 may be supported by the secure ring 120, and may extend through grooves 128 of the secure ring 120. As shown in FIG. 12, the rod 700 may be straight or bent (e.g., pre-bent).

Figures 13A, 13B, 13C:
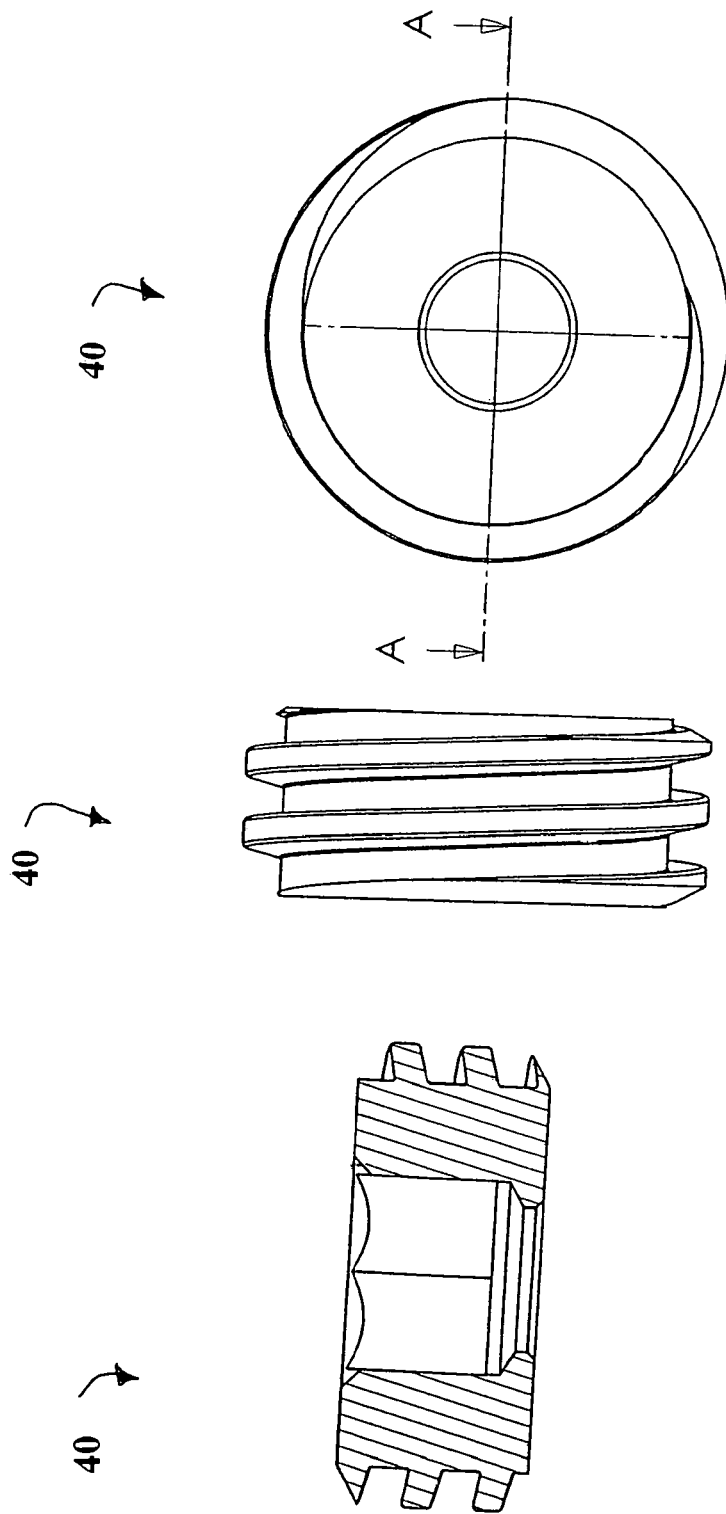
FIGS. 13A-13C illustrate an embodiment of a set screw of a bone stabilization device or assembly according to the present disclosure.

With reference to FIGS. 5 and 13, the assembly 10 may also include a set screw 40. As depicted in FIG. 5, the set screw 40 may be screwed into the receiver member 20 to press the rod 700 towards the secure ring 120. This allows the rod 700 to be secured between the secure ring 120 and the set screw 40, thereby stabilizing the rod 700 relative to the receiver member 20. For example, the set screw 40 may be introduced/tightened at or near the proximal end of the receiver member 20 (e.g., via internal and/or external threads located on the receiver member 20, and corresponding threads located on the set screw 40) to secure the rod 700 against the secure ring 120, thereby securing the assembly 10 in place.

Figure 14:
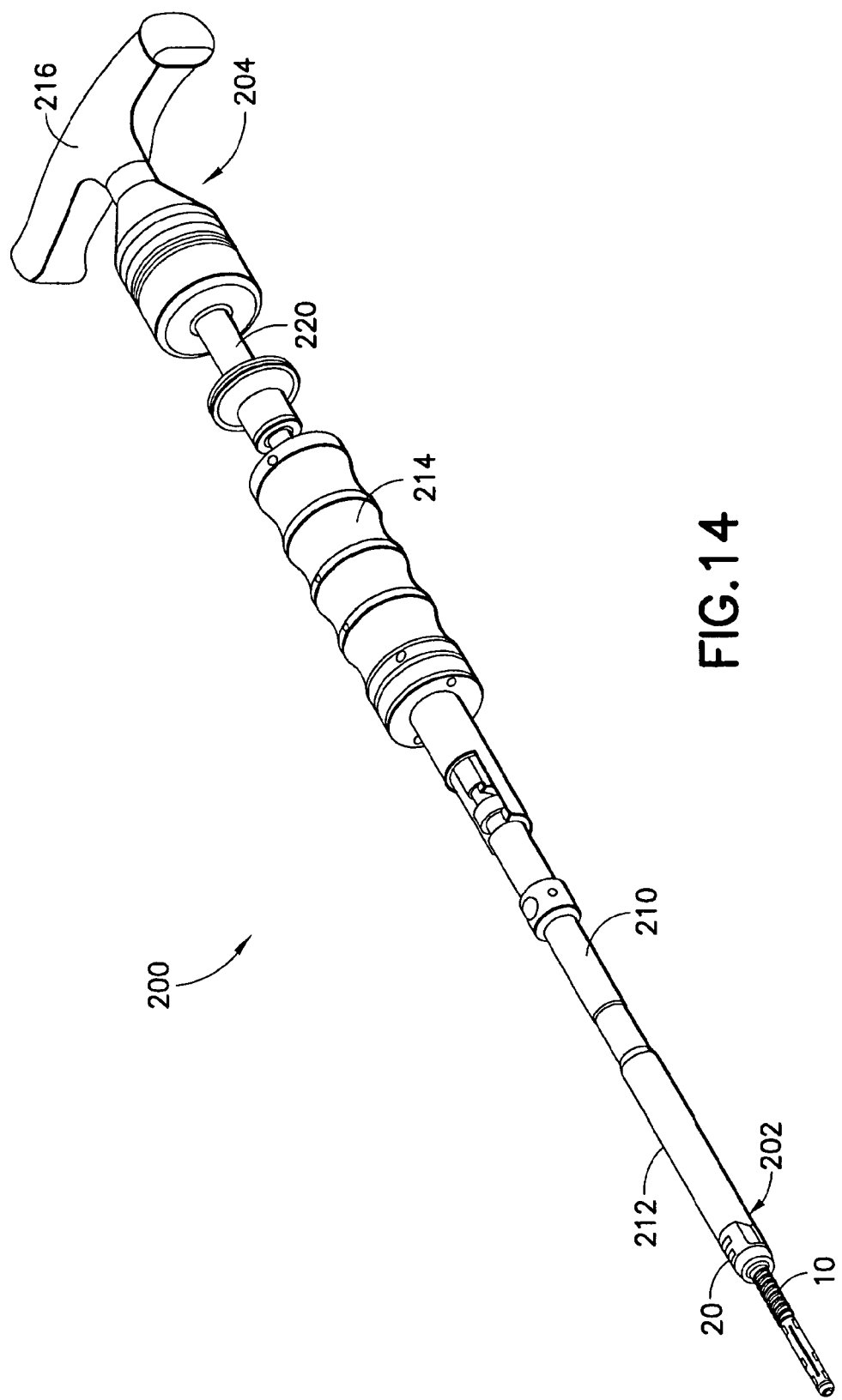
FIG. 14 illustrates an embodiment of a deployment and/or undeployment device according to the present disclosure.

In an exemplary embodiment and as shown in FIG. 14, a deployment and/or undeployment device 200 (e.g., a deployment tool) may be utilized in conjunction with the device 10. For example, deployment device 200 may be utilized to deploy and/or undeploy the anchoring elements or arms 22 of the device 10.

In one embodiment and as illustrated in FIG. 14, the deployment device 200 includes a distal end 202, a proximal end 204, a shaft 210 (e.g., tube), a sleeve 212 (e.g., a counter-rotation or counter-torque sleeve), a first handle 214 (e.g., a grip handle), a second handle 216 (e.g., a torque handle), and a deployment member 220 (e.g., a pull rod or the like). As shown in FIG. 14, the first handle 214 may be connected or coupled to the shaft 210, and the second handle 216 may be connected to the deployment member 220. In one embodiment, the second handle 216 may be releasably attached to the device 200.

Figure 21A:
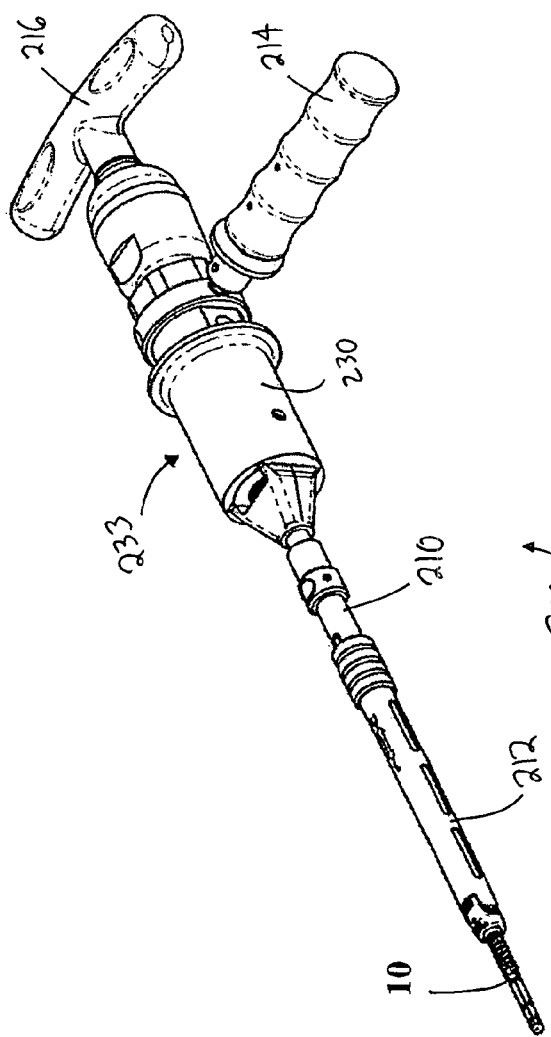
FIGS. 21A-21B illustrate another embodiment of a deployment and/or undeployment device according to the present disclosure.
Figure 21B:
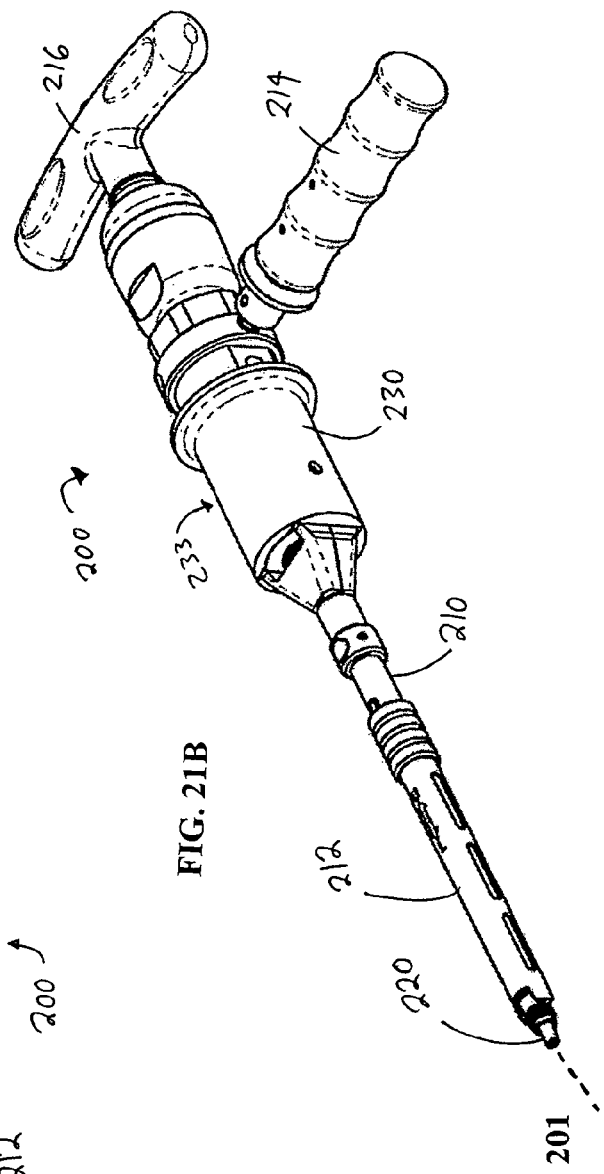

In an alternative embodiment and as shown in FIGS. 21A-21B, the first handle 214 is positioned or attached substantially perpendicular to the longitudinal axis 201 of the device 200. In another embodiment of the present disclosure and as depicted in FIGS. 21A-21B, the first handle 214 and/or the second handle 216 may be releasably attached to the device 200. In this alternative embodiment and as shown in FIGS. 21, 22 and 28, the device 200 also includes a connector member 233 having an outer sleeve 230.

FIGS. 15 and 28 illustrate the distal portion 202 of an exemplary deployment device 200 in further detail. As shown in FIGS. 15A and 28A-28B, the shaft 210 of the deployment device 200 has a threaded section or region 404 (e.g., external threads) positioned at or near the distal end 202. In one embodiment, threaded section 404 is configured to mate, couple or threadably engage with a threaded section 100 (e.g., inner threads; FIG. 2D) of the receiver member 20, thereby releasably attaching the deployment device 200 to the assembly 10. It is to be appreciated that the deployment device 200 may be releasably attached to the assembly 10 utilizing a variety of techniques or means.

In exemplary embodiments, the deployment member 220 is a pull rod or the like. As shown in FIGS. 15A and 28B, the deployment member 220 of the deployment device 200 may have an engaging mechanism 402 which is configured and dimensioned to releasably engage with and/or couple to the engagement head 25 (e.g., a "T" shaped head or the like) of the actuator 24 of the implant 10. In one embodiment, when the shaft 210 of the deployment device 200 is inserted into or engaged with the receiver member 20, the shaft 210 contacts or presses the secure ring 120 and advances or pushes it distally (e.g., downward).

In exemplary embodiments and as shown in FIGS. 14, 15B and 21, the sleeve 212 is a counter-rotation or counter-torque sleeve. The sleeve 212 may be positioned outside the shaft 210, and the sleeve 212 may surround part of the shaft 210. In one embodiment, the sleeve 212 is slidable and/or rotatable relative to the shaft 210 in a distal direction to allow an engaging portion 410 of the sleeve 212 to mate with a slot or opening or the like in the receiver member 20 (FIG. 15B). The sleeve may also be slidable and/or rotatable relative to the shaft 210 in a proximal direction to detach or decouple the engaging portion 410 from the receiver member 20. The sleeve 212 may include a plurality of engaging portions 410, and the receiver member may have a plurality of corresponding slots or openings as well.

In exemplary embodiments, portions of the deployment tool 200, such as, for example, the first handle 214 and/or the second handle 216, which require handling by the operator's hands, should be composed of a material that helps prevent the deployment tool 200 from slipping out of the operator's hands in a bloody or oily environment or the like. Such materials may include, without limitation, frictional materials, for example, materials having uneven surfaces, to facilitate gripping of the deployment device 200.

In some embodiments, the deployment device 200 is designed and/or composed of materials to assist the deployment device 200 to maintain structural integrity and to perform consistently through repeated use, cleaning, and/or sterilization processes, (e.g., gas or steam processes that are standard sterilization processes in the spine surgical instruments field). For example, the deployment device 200 may be composed of or fabricated from stainless steel, titanium, thermoplastic and other like materials suited for repeated use and sterilization of the deployment device 200. Also, in some embodiments, the deployment device 200 is configured so as to be easily and substantially cleaned and/or sterilized. Additionally, the deployment device 200 may be sized and may be of a weight so that a user can easily (e.g., using one hand) utilize the deployment device 200 to perform various functions described herein. Further, in some embodiments, the deployment device 200 may have a configuration that allows a user to easily perform the deployment of the assembly 10 using the force of one hand.

In exemplary embodiments, when utilizing deployment device 200 to deploy assembly 10, the assembly 10 is first inserted or implanted into bone and/or bone tissue (e.g., bone or bone tissue of the vertebra, cancellous bone, cortical bone, into the medullary canal of a bone, etc.). For example, such may be accomplished by drilling a small canal at or in the bone, followed by inserting at least a portion of anchor region 16 of implant assembly 10 into the canal. In exemplary embodiments, the inserting of anchor portion 16 may be accomplished with the aid of a plunger or the like. In other embodiments, the distal end 12 of assembly 10 may have a sharp tip for allowing assembly 10 itself to penetrate bony tissue. In such cases, the drilling step may not be needed. In another embodiment and as shown in FIGS. 25A-25B, region 16 may also have threads or thread-like features that may be introduced to the bone by turning or rotating assembly 10, which will be continued by the turning or rotating of region 18.

After anchor region 16 has been inserted into the bone and/or bone tissue, the assembly 10 may be further advanced into the bone and/or bone tissue by turning or rotating the first body region 18 about axis 28, thereby screwing the first body region 18 into the bone and/or bone tissue. The turning/rotating of the first body region 18 may be accomplished using a separate tool or the like (e.g., a driver or screwdriver). Alternatively, the deployment device 200 may be used to screw or advance the first body region 18 into the bone and/or bone tissue. For example, the deployment device 200 (or a separate tool) may be attached to the receiver member 20 of the assembly 10 by screwing (e.g., in a clockwise direction) the threaded portion 404 of the shaft 210 into the receiver member 20. For such purpose, the sleeve 212 may be advanced so that the engaging portion 410 mates with the side slot on the receiver member 20. The attachment of the shaft 210 to the receiver member 20 may then be accomplished by holding the sleeve 212 with one hand, and turning/rotating the first handle 214 with the other hand. As the first handle 214 is turned, the threaded portion 404 is advanced into the receiver member 20. The threaded portion 404 may then be substantially engaged with or advanced into the receiver member 20. The first handle 214 can then be continuously rotated to turn the shaft 210, which in turn, will rotate the receiver member 20 and the first body region 18 of the assembly 10, thereby screwing or advancing the first body region 18 of the assembly 10 into the bone and/or bone tissue.

Figure 16A:
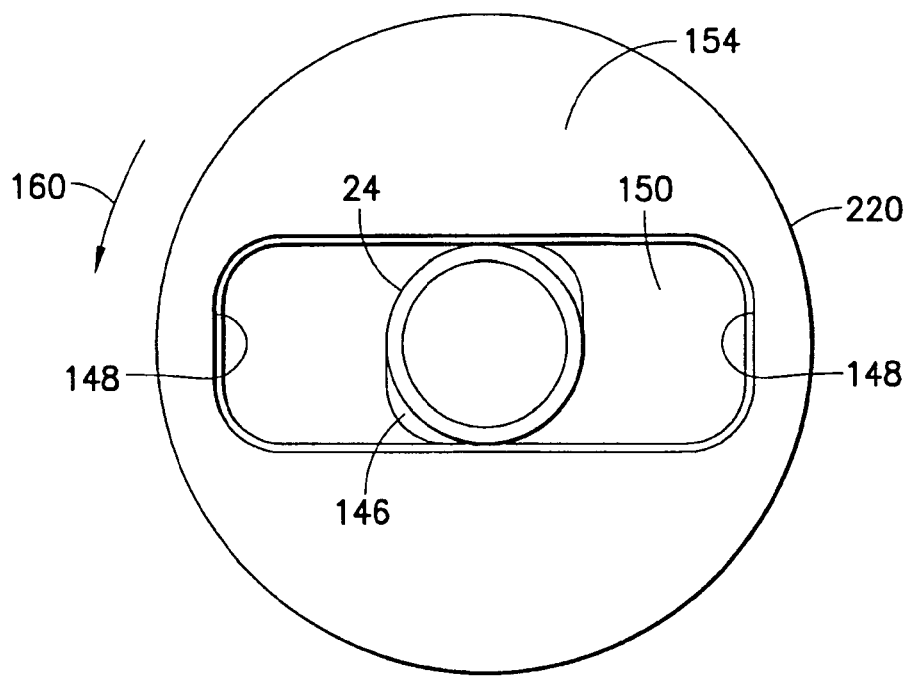
FIGS. 16A and 16B illustrate an embodiment of an engaging mechanism of a shaft of a deployment and/or undeployment device and a head of an actuator of a bone stabilization device or assembly according to the present disclosure.
Figure 16B:
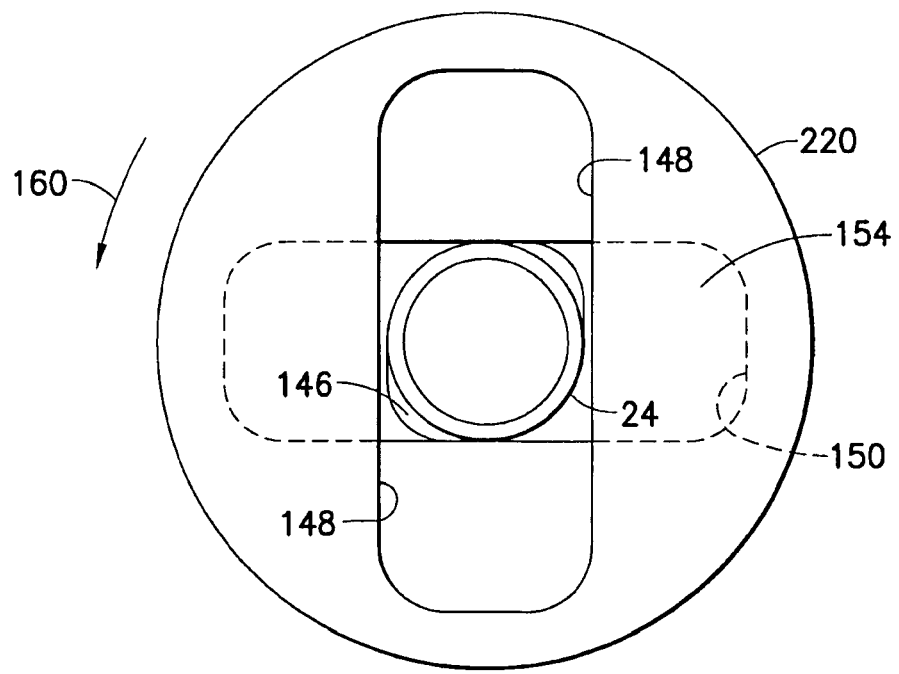

After the assembly 10 (e.g., the first body region 18) has been desirably placed or positioned in the bone and/or bone tissue, the deployment device 200 may then be used to deploy the arms 22 of the assembly 10. For such purpose and as shown in FIG. 15A, deployment member 220 is advanced distally until the engaging mechanism 402 of deployment member 220 is adjacent to engagement head 25 of actuator 24 of assembly 10. In exemplary embodiments, the engaging mechanism 402 at or near the distal end of deployment member 220 has an end plate 154 (FIG. 16A). The end plate 154 has inner edges 148 that define an opening 150. The opening 150 is configured and dimensioned so that head 25 of actuator 24 may fit therethrough when the deployment member 220 is oriented at a certain angle relative to the head 25. In some embodiments, the deployment member 220 may have marker(s) to indicate a proper insertion of the head 25 into the opening 150 of deployment member 220. After end plate 154 has been advanced past the head 25, the deployment member 220 may be turned about its longitudinal axis in the clockwise (i.e., clockwise when viewed from the proximal end towards the distal end) direction 160 shown so that the head 25 is locked or engaged against the inner surface of the end plate 154 (FIG. 16B). In exemplary embodiments, the deployment member 220 may be turned/rotated about 90° (e.g., via a deployment member knob or manually) to lock against the head 25 of the actuator 24. In some embodiments, the deployment device 200 may have marker(s) to indicate the rotation (e.g., quarter turn rotation). For example, a rotational scale marked ring can be locked at any orientation on the deployment device 200 with a matching indicator on the proximal end 204 of the deployment device 200, e.g., on the deployment member knob. In exemplary embodiments and as shown in FIGS. 8 and 16A-B, after the deployment member 220 has been turned about 90°, the edges 148 abut against the protrusion 146 of the actuator 24, which prevents deployment member 220 from being turned further.

Figures 22A, 22B, 22C, 22D, 22E:
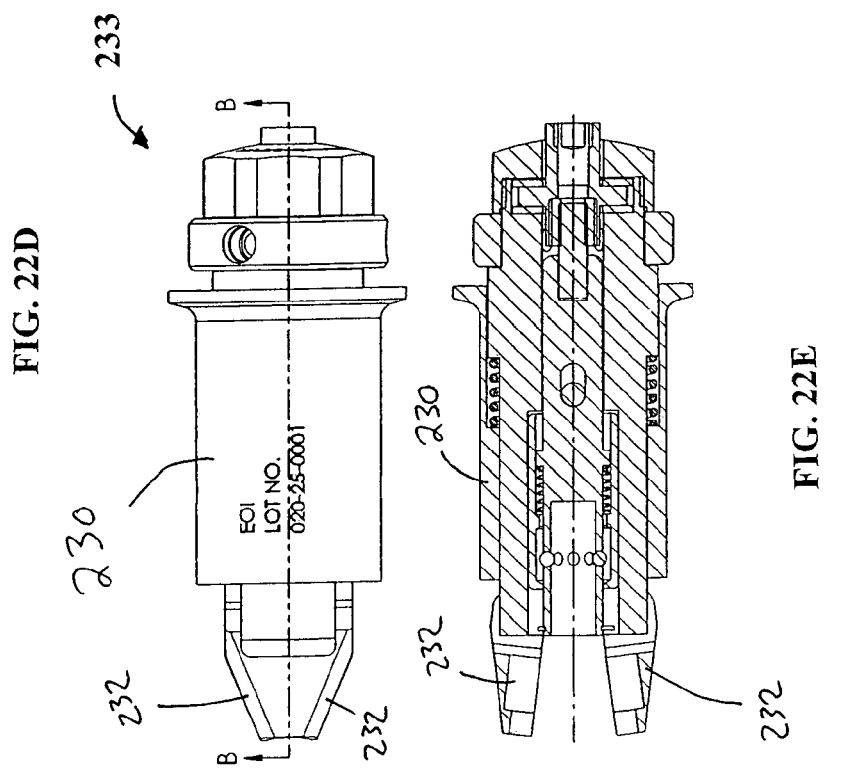
FIGS. 22A-22E illustrate partial views of the deployment and/or undeployment device depicted in FIG. 21.
Figure 23A:
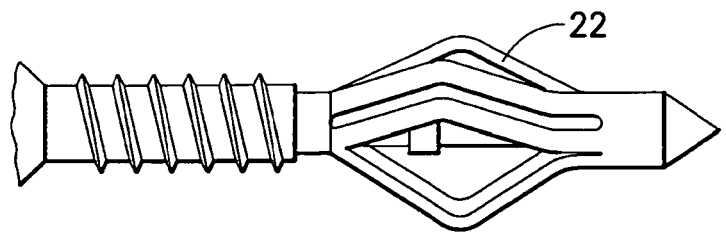
FIGS. 23A-23F illustrate various alternative embodiments of the arms of a deployed anchor region of a bone stabilization device or assembly according to the present disclosure.
Figure 23B:
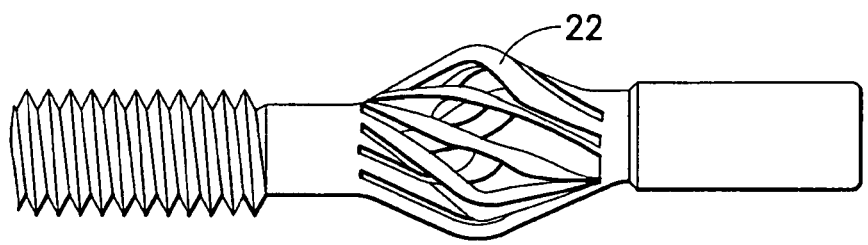
Figure 23C:
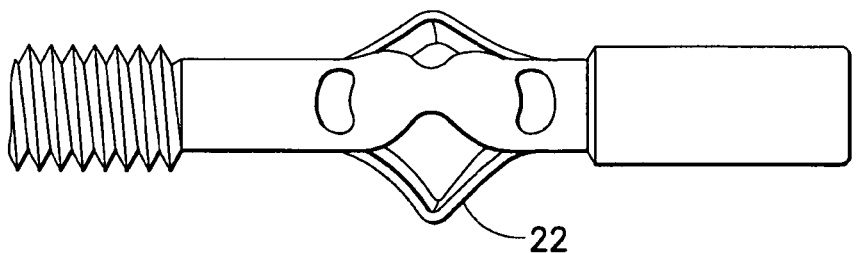
Figure 23D:
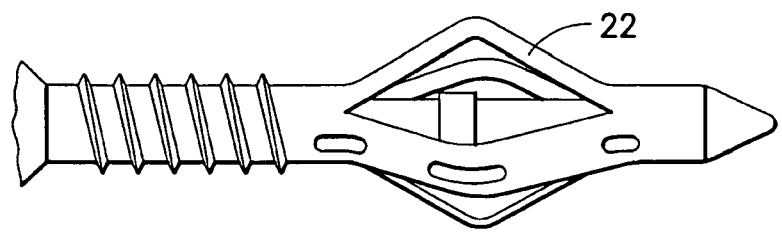
Figure 23E:
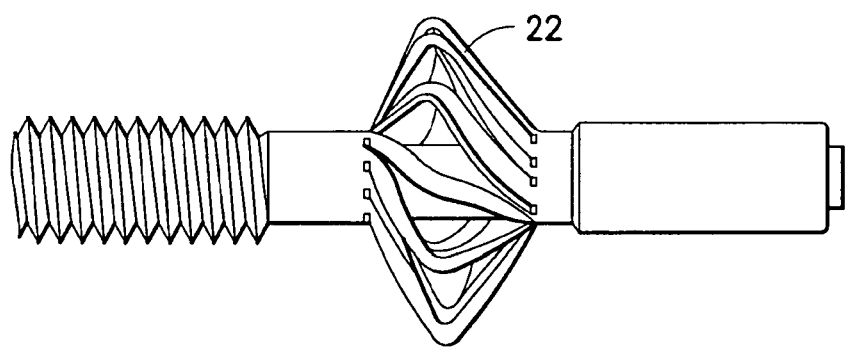
Figure 23F:
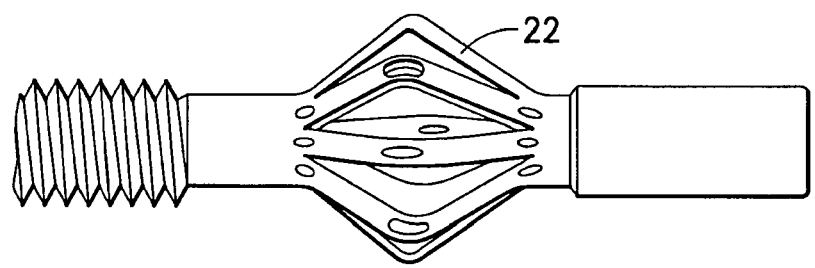

In exemplary embodiments, after engaging mechanism 402 of deployment member 220 has engaged with head 25 of actuator 24 of assembly 10, deployment member 220 may be retracted proximally to pull actuator 24. With reference to FIGS. 21, 22 and 28, connector member 233 may be releasably connected to first and second handles 214, 216, and connector member 233 may be releasably connected to shaft 210 and to deployment member 220. As shown in FIGS. 21, 22 and 28, connector member 233 includes clamps or jaws 232 or the like, and an outer sleeve 230. In one embodiment, the outer sleeve 230 of connector member 233 is configured to be pulled proximally, thereby opening clamps or jaws 232 so that shaft or tube 210 and/or the deployment member 220 may be releasably connected to the connector member 233 (FIG. 22E). For example, once the outer sleeve 230 of the connector member has been pulled proximally to open the clamps 232, the deployment member 220 may be inserted into a recess or cavity 234 of the connector member 233, and the shaft or tube 210 may be positioned between or adjacent to the opened clamps or jaws 232. Distal movement of the outer sleeve 230 then releasably forces or secures the clamps 232 onto and/or around the shaft or tube 210, and also releasably secures the deployment member 220 to the connector member 233 inside the recess 234, e.g., via an internal tube or hollow member 235 or the like pressing/pushing/forcing securing balls or members 236 or the like onto the deployment member 220.

In exemplary embodiments and as shown in FIG. 22, the internal tube or hollow member 235 includes a threaded proximal portion 237 that is threadably engaged with threads of handle member 238 of handle 216. The deployment member 220 may now be retracted proximally to pull the actuator 24. Such may be accomplished by turning the second handle 216, which may be configured to translate a torque motion into a translation motion. Mechanisms for translating torque motion into a translation motion is well known in the art. In general, the connector member 233 allows for the transmission of rotational movement to linear movement. In some cases, the user operating deployment device 200 may use one hand to turn handle 216 on deployment device 200 clockwise, causing the deployment device's 200 deployment member 220 to translate proximally. For example, rotation of handle 216 causes rotation of handle member 238, which thereby causes internal tube 235 to move linearly (e.g., pulled or pushed), which in turn causes deployment member 220 to move linearly (e.g., translate proximally or distally). Actuator 24 engaged with deployment member 220 thus moves linearly as well.

Figure 30:
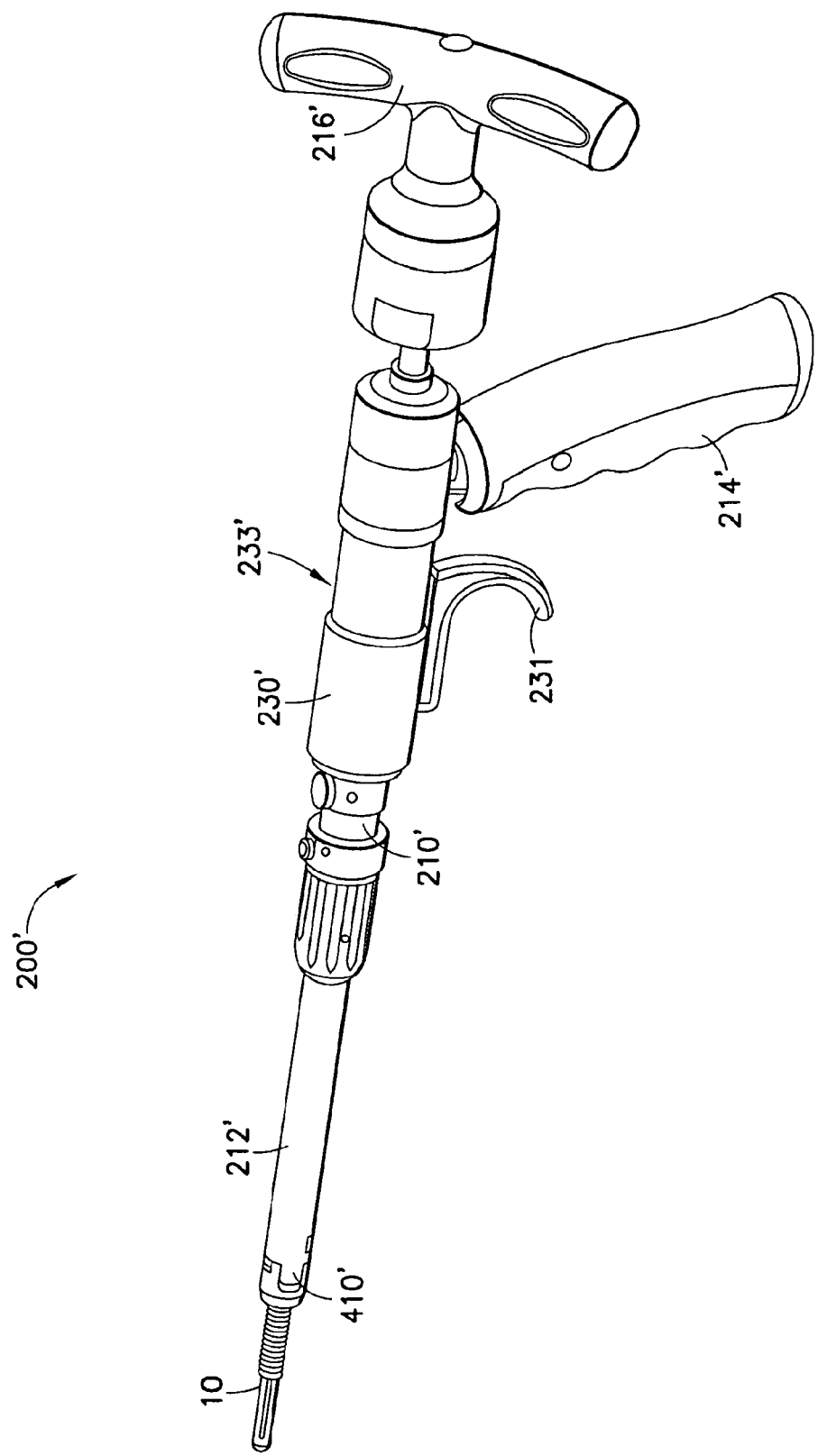
FIG. 30 depicts a side perspective view of another embodiment of a deployment and/or undeployment device according to the present disclosure.
Figure 31:
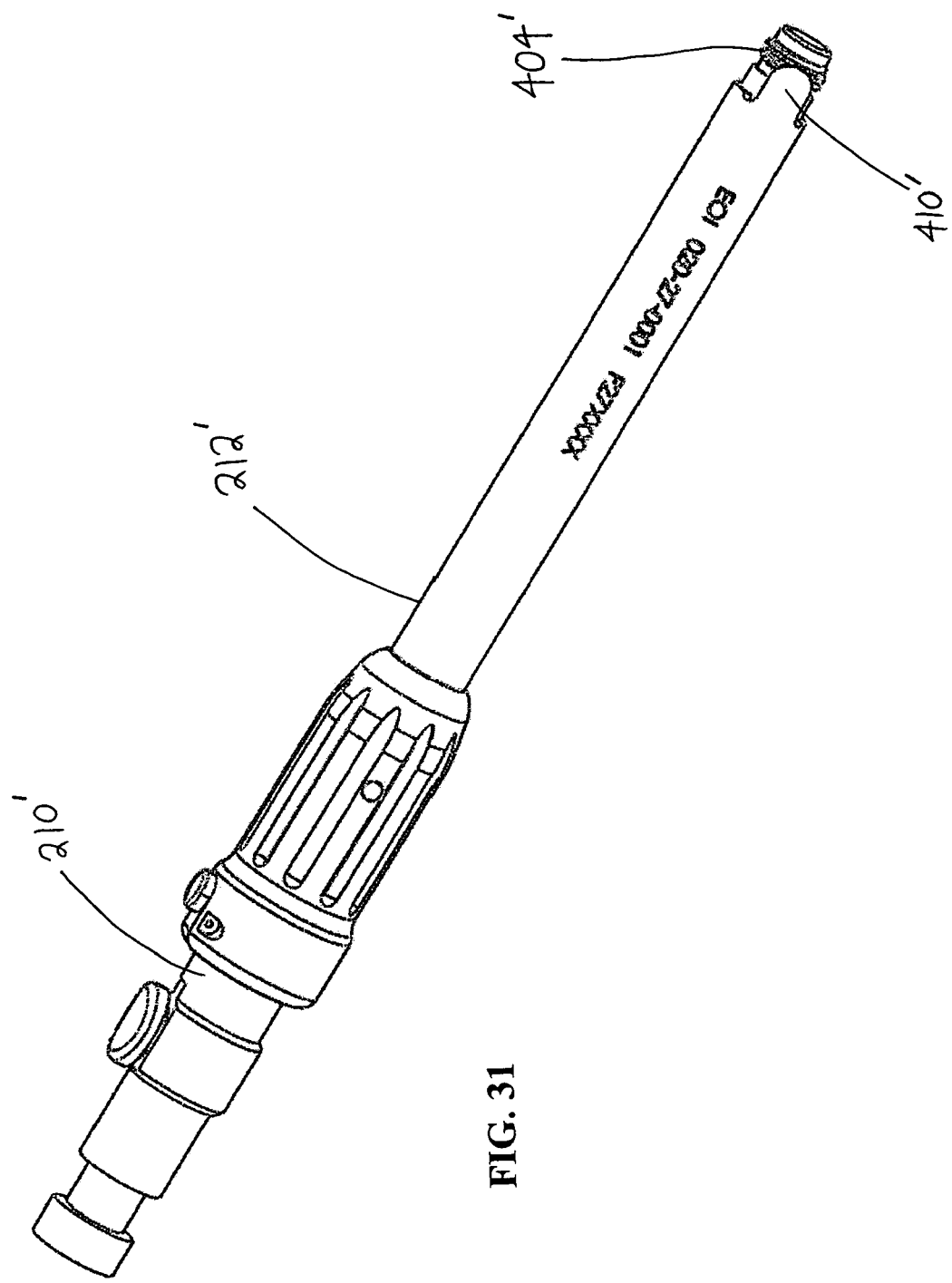
FIG. 31 is a partial side perspective view of the device of FIG. 30.
Figure 32:
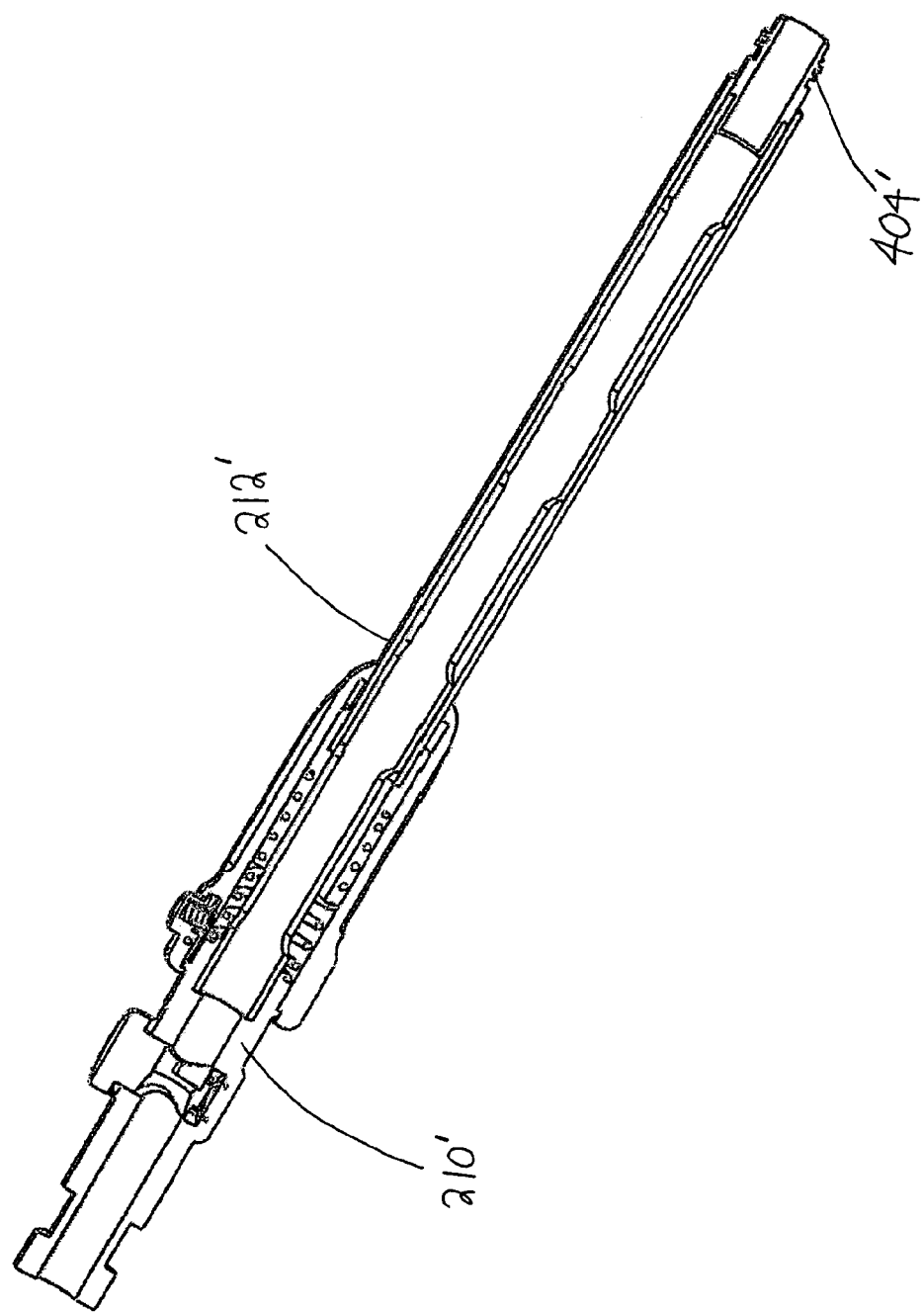
FIG. 32 is a partial cross-sectional side view of the device of FIG. 30.
Figure 33:
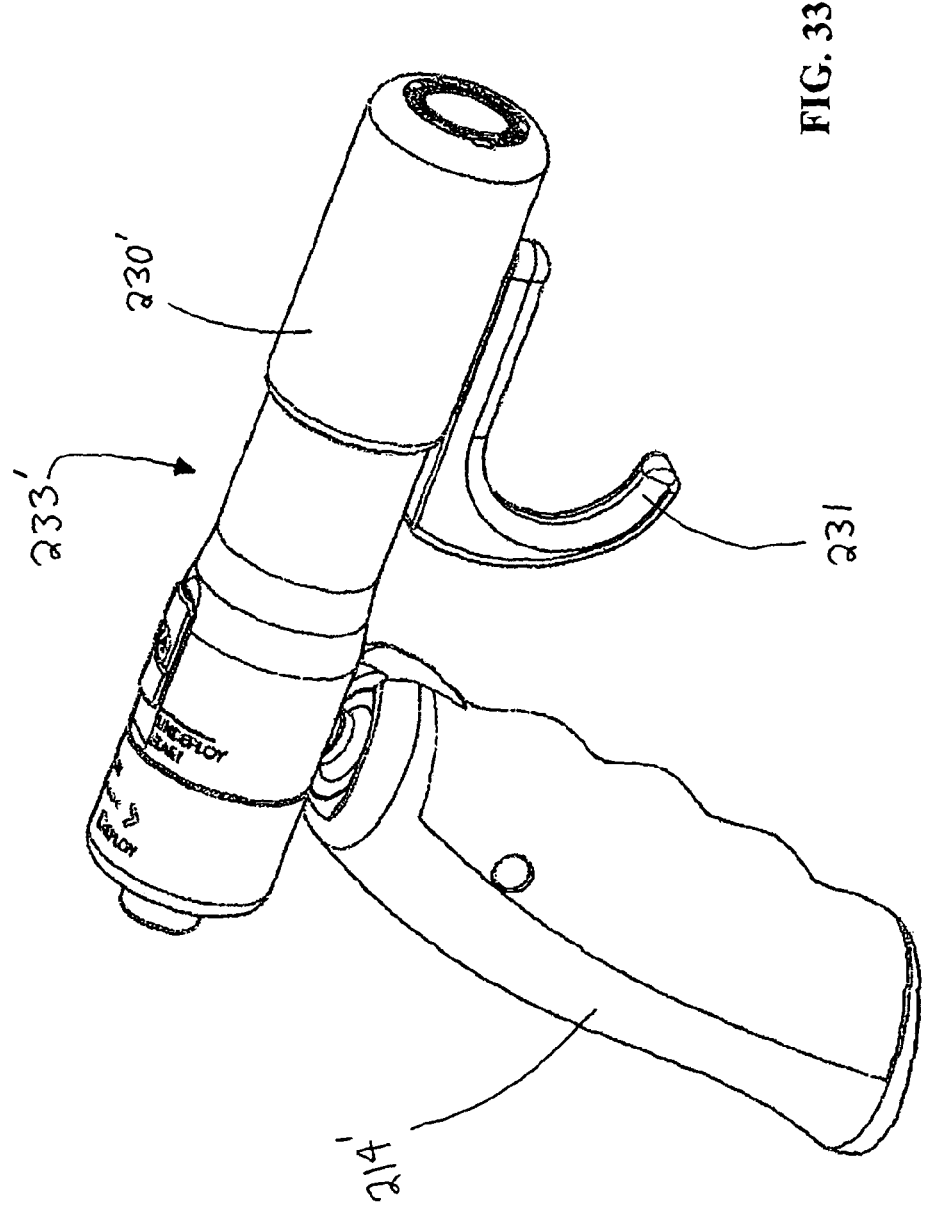
FIG. 33 is a partial side perspective view of the device of FIG. 30.
Figure 34A:
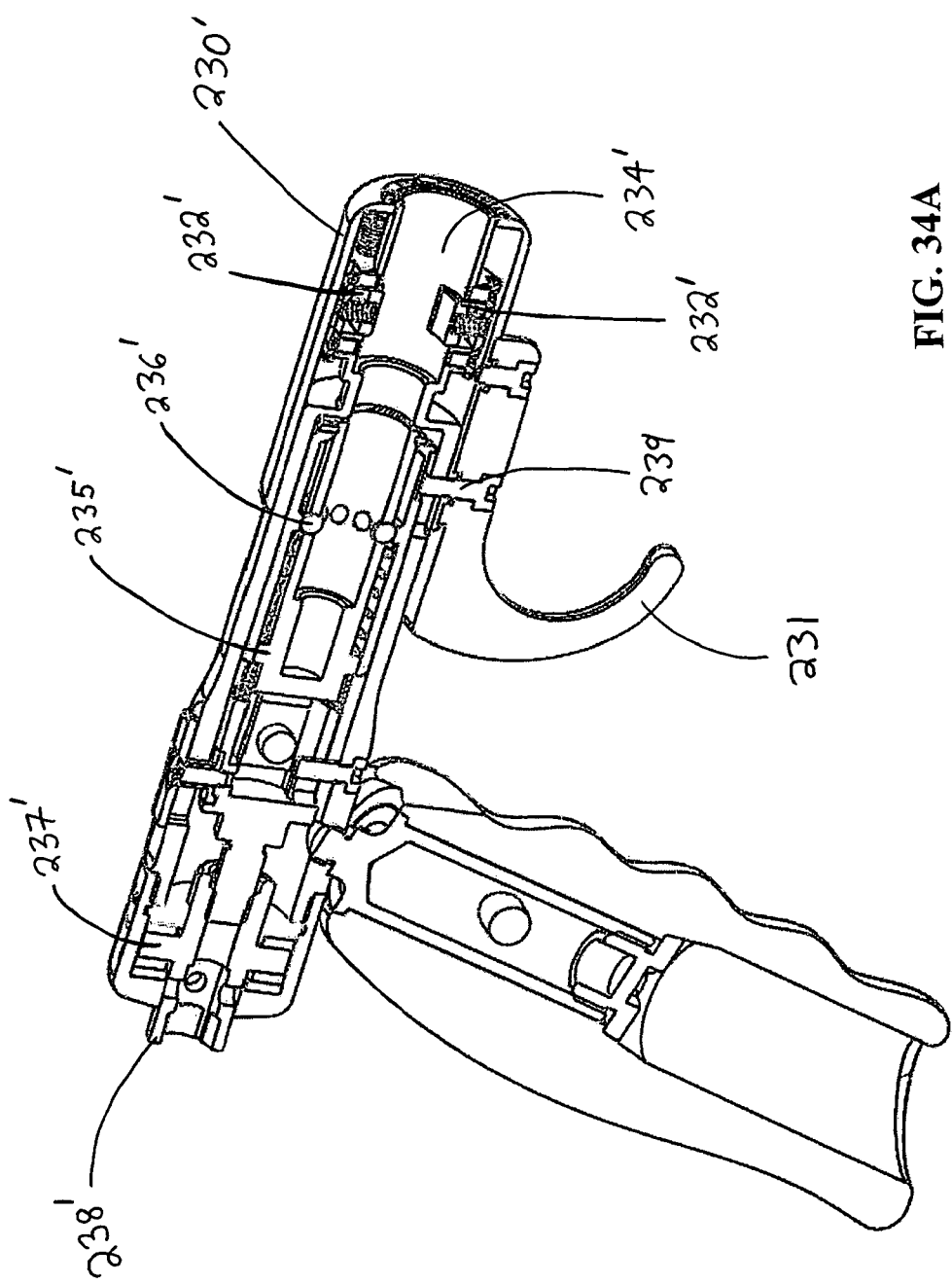
FIGS. 34A-34B are partial cross-sectional side views of the device of FIG. 30, without and with deployment member inserted.
Figure 34B:
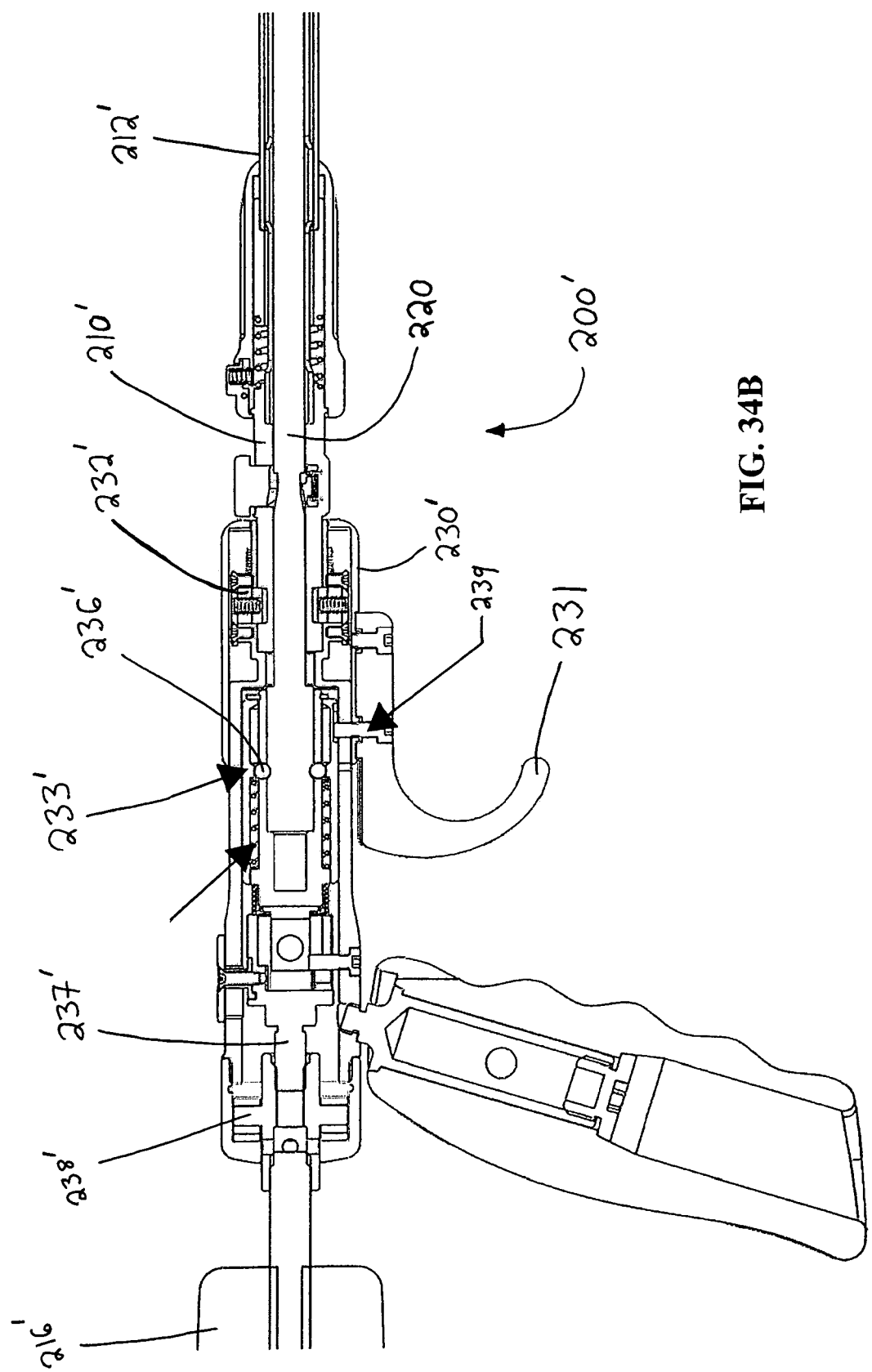

In an alternative embodiment and as shown in FIGS. 30-34, deployment device 200' may be utilized to deploy and/or undeploy anchoring elements 22 of device 10. Similar to device 200, deployment device 200' typically includes a shaft 210' (e.g., tube), a sleeve 212' (e.g., counter-rotation sleeve), a first handle 214', a second handle 216', and a deployment member 220 (as shown in FIGS. 28B and 34B). In this embodiment and as shown in FIGS. 30 and 33-34, device 200' includes a connector member 233' having a trigger member 231. Like device 200, shaft 210' of device 200' has a threaded region 404' configured to mate with receiver member 20. Sleeve 212' also typically includes engaging portion 410' for engaging with receiver member 20. Additionally and as further discussed below, deployment member 220 may be utilized in conjunction with device 200' as discussed with respect with device 200 to deploy/undeploy arms 22 (e.g., engaging mechanism 402 of deployment member 220 engages head 25 of actuator 24 to facilitate deployment/undeployment of arms 22 by utilizing deployment device 200' in conjunction with deployment member 220).

With reference to FIGS. 30-34, connector member 233' may be releasably connected to shaft 210' and to deployment member 220. Connector member 233' includes clamps 232', and trigger member 231 is configured to be moved proximally (i.e., towards handle 216'), thereby opening or widening the clamps 232' and moving proximally the outer sleeve 230' around internal tube 235' by means of proximal screw/pin 239 of trigger member 231, thereby allowing the securing balls 236' to move freely (e.g., in the unlocked position) and so that shaft 210' and deployment member 220 may be releasably connected to connector member 233'. For example, once the trigger member 231 has been moved proximally to open or widen clamps 232' and to unlock securing balls 236', deployment member 220 may be inserted into cavity 234' of connector member 233', and shaft 210' may be positioned between opened/widened clamps 232'. Distal movement of trigger member 231 then secures clamps 232' onto, around and/or against shaft 210', and also releasably secures deployment member 220 to connector member 233' inside recess 234', via internal tube 235' pressing/forcing securing balls 236' or the like onto deployment member 220 (e.g., by moving distally the outer sleeve 230' around internal tube 235' and by means of at least one spring member 241 positioned around internal tube 235' locking the securing balls 236' into internal tube 235 and into deployment member grooves 243 (FIG. 28B)). Spring member 241 is configured to maintain the outer sleeve 230' in its distal position when trigger 231 is in its distal position. As noted, outer sleeve 230' maintains the securing balls 236' in the locked position when trigger 231 is in its distal position. As discussed above, once the trigger member 231 has been moved proximally, screw/pin 239 pulls the outer sleeve 230' proximally against spring 241 and allows balls 236' to release and permits the deployment member to enter tube 235'. When the trigger 231 is released, the spring 241 pushes the outer sleeve 230', thereby constraining the balls 236' in a fully engaged position with deployment member 220. Deployment member 220 along with deployment device 200' may then be utilized to deploy/undeploy arms 22 of device 10 as discussed above in regards to device 200 (e.g., via threaded proximal portion 237' of internal tube 235' being engaged with threads of handle member 238' of handle 216', and with the turning of handle 216' to translate torque motion into translation motion to deploy/undeploy arms 22).

It is to be noted that the linear forces that are being applied by deployment member 220 on actuator 24 requires a counter-force in order to deliver the force to shaft or tube 210, 210' and perform deployment or un-deployment of assembly 10. In order to provide the counter-force, tube 210, 210' is releasably secured to connector member 233, 233' via clamps 232, 232'.

In exemplary embodiments, the user's other hand may hold onto the first handle 214 to apply counter-resistance to the turning motion for added stabilization. This technique is also advantageous in that it minimizes an amount of force (e.g., torque force) transferred to the bone and/or bone tissue, other than the forces created by the outward movement of the arms 22. In general, the device 200 is configured and dimensioned to allow a user to deploy the assembly 10 to the desired level of deployment by utilizing the force of one hand. The pulling of the actuator 24 moves/advances the second body region 15 proximally, thereby creating a compression force on the anchor region 16. As a result, the arms 22 buckle or bend outwardly from the axis 28, forming a deployed configuration (FIG. 3). In exemplary embodiments, the deployment device 200 may be utilized to deploy the arms 22 to any stage of deployment (e.g., slight deployment, half deployment, full deployment, etc.), up to and including full deployment of the arms 22. In one embodiment, the full deployment limit of the assembly 10 is defined or controlled by the device 200 and not by the assembly 10.

Figure 17A:
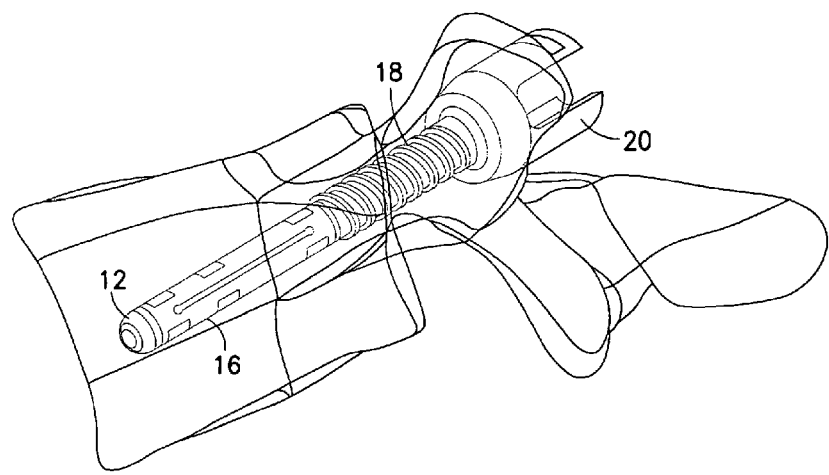
FIGS. 17A and 17B illustrate embodiments of a undeployed and deployed bone stabilization device or assembly according to the present disclosure.
Figure 17B:
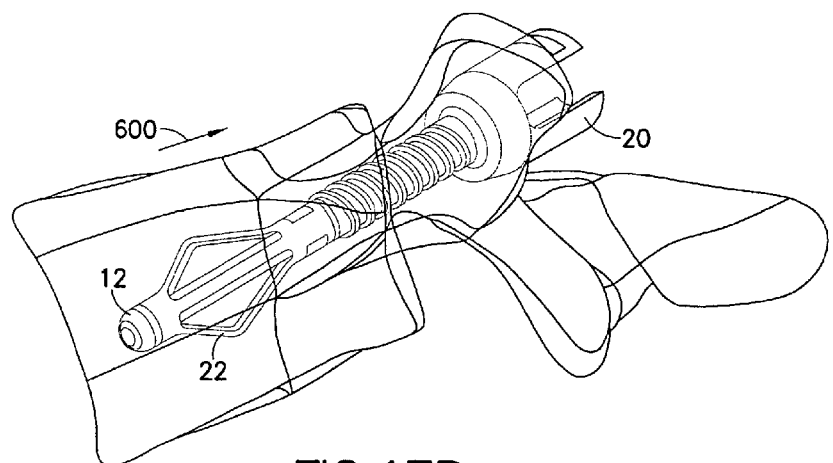

In exemplary embodiments, the radially outward movement of the arms 22 causes the arms 22 to penetrate into bone and/or bone tissue (e.g., cancellous tissue of the vertebra), thereby locking/deploying the assembly 10 relative to the bone (e.g., relative to the vertebra). For example, FIG. 17A is a schematic diagram showing the assembly 10 placed or positioned at a desired position in a vertebra, and FIG. 17B shows the assembly 10 that has been deployed by expanding the arms 22 radially outward. As shown in the figures, the expanded arms 22 function to anchor the assembly 10 relative to the vertebra so that the implant assembly 10 is at least prevented from moving in the direction 600 shown. It should be noted that the arms 22 of the assembly 10 need not be fully deployed (although they can be if desired), and that the amount of movement by the arms 22 may be selected accordingly, depending on the configuration of the vertebra and the specific needs of an operation. For example, in some embodiments, the arms 22 of the assembly 10 may be partially deployed, and still be able to perform the function of anchoring the assembly 10 relative to the bone and/or bone tissue (e.g., vertebra, medullary canal, etc.). In another embodiment, region 18 may be shorter in length, thereby allowing arms 22 to deploy in part near the end of and/or partially into the pedicle canal or the like, to thereby get in contact with the cortical bone of the pedicle for improved fixation.

In exemplary embodiments of the present disclosure, the deployment device 200 may further include a movement limiter (e.g., a stopper, such as that in a form of a protrusion) that is configured to stop the linear motion of the actuator 24 and/or stop the movement of the deployment member 220, when the arms 22 of the assembly 10 reach full expansion/deployment. This movement limiter may be configured to vary to match the deployment (e.g., full deployment) of different sizes (e.g., different diameters) of the assembly 10 (e.g., assemblies having an outer diameter of about 5.5 mm, about 5.8 mm, about 6.5 mm, about 7.5 mm, about 8.5 mm, etc.). In some embodiments, the movement limiter may be adjustable—e.g., by changing a position of the movement limiter. In such cases, the positioning of the movement limiter for various sizes of different assemblies 10 may be marked on the movement limiter and/or on the device 200 for allowing a user to properly adjust the movement limiter to correspond to a particular size of assembly 10 being utilized/deployed.

In exemplary embodiments and as shown in FIGS. 28A-28B, the deployment device 200 may include a linear movement limiter 299 which is configured and dimensioned to limit the linear movement (e.g., proximal linear movement) of the deployment member 220. In general, the proximal portion or region of the shaft 210 of the deployment device 200 may include a linear movement limiter 299. In one embodiment, the linear movement limiter 299 is a button or the like (e.g., a round button) which has a small step or the like inside, with the small step providing the linear movement limit of the deployment member 220. For example, while performing a deployment of the arms 22 of the assembly 10 with the deployment member 220 (or while proximally unscrewing the actuator 24 with the deployment member 220 during an unlocking/un-deployment, as discussed below), the linear movement limiter 299 limits the proximal linear motion of the deployment member 220 up to the limit (e.g., the small step of the button) of the linear movement limiter 299.

In exemplary embodiments, the second handle 216 is a torque limit handle which includes a mechanical force limiting mechanism which is configured to limit the pulling force of the deployment member 220 (e.g., to prevent deployment of the assembly 10 inside the pedicle canal). For example, the mechanical force limiting mechanism may be configured to ensure that the pulling force of the deployment member stays within a predetermined range.

In one embodiment, the force limiting mechanism may be a torque limiting mechanism that forms part of the torque limit handle 216 on the deployment tool 200. For example, a slip mechanism may be provided which allows mechanical slippage when an amount of torque applied to the handle 216 (or an amount of pulling force applied to the deployment member 220) exceeds a certain amount. Torque limiting mechanisms are well known in the art. The force limiting mechanism and/or the settings for the force limiting mechanism may vary for different sizes of the assembly 10 (e.g., assemblies having an outer diameter of about 5.5 mm, about 5.8 mm, about 6.5 mm, about 7.5 mm, about 8.5 mm, etc., and/or for different sizes in length). In some embodiments, the force limiting mechanism may be adjustable. For example, the settings for the force limiting mechanism for various sizes of different assemblies 10 may be marked on the force limiting mechanism and/or on the device 200 for allowing a user to properly adjust the force limiting mechanism to correspond to a particular size of assembly 10 being utilized/deployed. In some embodiments, the force limiting mechanism may be selectively configured to limit the pulling force on deployment member 220, and/or on actuator 24 (e.g., to limit the pulling force of deployment member 220 not to exceed $2600^{+150}$ [N] for an assembly 10 having a diameter of about 5.5 mm, or not to exceed $2800^{+150}$ [N] for an assembly 10 having a diameter of about 6.5 mm, or not to exceed $3000^{+150}$ [N] for an assembly 10 having a diameter of about 7.5 mm. Forces above the set limits will not be transferred to the assemblies 10.

In exemplary embodiments, after deployment of the assembly 10 (e.g., after buckling and/or bending of the arms 22), the deployment device 200 may be used to lock the assembly 10 in a desired position using a locking mechanism or the like. In exemplary embodiments, the assembly 10 may be locked in place at any deployment stage (e.g., slight deployment, half deployment, full deployment, etc.), up to and including the full deployment stage. For example, the locking may be performed by first releasing the force applied by the device 200 on the deployment member 220 (e.g., by releasing back the handles 214, 216). In exemplary embodiments, the connector member 233 is then un-secured from the device 200 by pulling the outer sleeve 230 proximally to disengage the connector member 233 from the device 200 (e.g., thereby opening the clamps 232 from around the tube 210, and thereby unsecuring the deployment member 220 from the securing balls or members 236). The proximal end of the deployment member 220 is now exposed, and may be rotated (e.g., finger-tightened clockwise) to advance the actuator 24 distally (e.g., about 1 mm to about 8 mm) relative to region 15 to secure and/or lock deployment of device 10 (see FIGS. 3 and 4).

For example, since the edge portions 148 (defining the slot 150) of the deployment member 220 are already engaged with the mid portion 146 of the actuator 24, turning the deployment member 220 clockwise (i.e., in the direction shown in FIG. 16B) will advance/screw the actuator 24 distally (approximately 2 mm) relative to the second body region 15, with the threaded distal end of the actuator 24 advancing relative to the inner threaded region of the second body region 15.

In exemplary embodiments, the actuator 24 may be advanced/screwed distally until the bottom surface 147 of the protrusion 146 of the actuator 24 abuts against the face 152 of the first body region 18 (see FIGS. 3-4, 6 and 8). Such configuration prevents the actuator 24 from moving distally relative to the first body region 18, which in turn, prevents the second body region 15 from moving distally, thereby locking the deployed arms 22 in their deployed positions and preventing the deployed arms 22 from returning to their undeployed positions. The deployment member 220 of the deployment tool 200 may include a mechanical torque-limiting mechanism, e.g., a slip mechanism for allowing mechanical slippage, to prevent over-tightening of the assembly locking mechanism. In one embodiment, the torque-limiting mechanism prevents torques larger than $0.7^{+0.2}$ [NM] from being transferred to the head 25 of the actuator 24.

In an alternative embodiment and as previously discussed, elongate member 24 or the like may be utilized as a locking member after a separate and removable actuator (e.g., deployment rod or control wire or the like) has been utilized to deploy arms 22.

After the assembly 10 has been desirably deployed (and locked), the deploying device 200 may be disconnected from implant assembly 10. For example and as shown in FIG. 16, the deployment device 200 may be disconnected from the assembly 10 by turning the deployment member 220 a quarter of a turn counter-clockwise to release the interlock between the deployment member 220 and the head 25 of the actuator 24. This may be accomplished with the aid of the markers discussed herein. The deployment member 220 may then be retracted proximally to fully disconnect the deployment member 220 from the head 25 of the deployment rod 24. Next, the counter rotation sleeve 212 is advanced so that the engaging portion(s) 410 of the counter rotation sleeve 212 is mated into the slot(s) at the receiver member 20 (as in FIG. 15B). The user then turns the grip handle 214 (e.g., counter-clockwise) to unscrew the threaded section 404 of the shaft 210 from the receiver member 20, while using another hand to grip onto the counter rotation sleeve 212. In particular, the counter rotation sleeve 212 may be used to hold the receiver member 20 in place relative to the bone, so that the shaft 210 may be unscrewed relative to the receiver member 20 without causing the receiver member 20 to rotate in the same direction as the turning of the shaft 210. The grip handle 214 is turned until the shaft 210 has been completely disconnected from the receiver member 20 of the assembly 10.

In some embodiments, the same deployment device 200 (or separate deployment tool(s) 200) may be used to implant and deploy additional assemblies 10 into the same bone (e.g., the same vertebra), or into a different bone (e.g., a different vertebrae). For example, a first assembly 10 is implanted into a vertebra on one side of the spine, and a second assembly 10 may be implanted into the same vertebra on the opposite side of the spine. In other embodiments, a first assembly 10 is implanted into a first vertebra, and a second assembly 10 is implanted into a second vertebra, which may be located next to the first vertebra, or spaced away from the first vertebra (e.g., with other vertebrae therebetween). In further embodiments, a first pair of assemblies 10 may be implanted into a first vertebra on opposite sides of the spine, and a second pair of assemblies 10 may be implanted into a second vertebra on opposite sides of the spine. In such cases, the four assemblies 10 may be coupled to each other by connecting rods 700 or the like and at least one cross-connector 800 (FIGS. 5 and 18-19).

In exemplary embodiments and as shown in FIGS. 18A-18B and 19, a cross-connector 800 may be used in conjunction with connecting rods 700. The cross-connector 800 includes a first portion 802, a second portion 804, a first securing mechanism 806, and a second securing mechanism 808. The first portion 802 is slidable relative to the second portion 804 so that a distance between the first and second securing mechanisms 806, 808 may be adjusted. When a desired distance between the first and second securing mechanism 806, 808 has been achieved, a set screw 820 may be used to secure them in place. The securing mechanisms 806, 808, which may be U-shaped clamps or latches, for example, are for engaging portions of the connecting rod(s) 700 during use. In exemplary embodiments, each securing mechanism 806/808 includes two latches 830, 832, that are rotatable around respective hinges 824, 826. A first inner body 822 is slidably disposed within the cavity 840 of the first portion 802, and a second inner body 822 is slidably disposed within the cavity 842 of the second portion 804. The cross-connector 800 also includes two countersink screws 828. Each countersink screw 828 is coupled to the inner body 822 via screw threads. A tool may be provided for insertion into the countersink of the countersink screw 828, and may be used to turn the screw 828. Turning the screw 828 in one direction causes the inner body 822 to move outward from the cavity 840, thereby allowing the latches 830, 832 to swing outward to release the rod 700. Turning the screw 828 in the opposite direction causes the inner body 822 to move into the cavity 840, thereby pushing the latches 830, 832 inward to clamp against the rod 700. In addition, the various embodiments of the cross-connectors shown and described in U.S. patent application Ser. No. 12/032,721 may be utilized in conjunction with the assemblies 10 of the present disclosure, the entire contents of which is hereby incorporated by reference its entirety.

FIG. 19 illustrates an example of a configuration formed using four implant assemblies 10a-d, two connecting rods 700a-b, and a cross-connector 800. The vertebrae and spine are not shown for clarity. In the illustrated example, the assemblies 10a and 10b are implanted and anchored into a first vertebra, the assembly 10c is implanted and anchored into a second vertebra located next to the first vertebra, and the assembly 10d is implanted and anchored into a third vertebra located next to the second vertebra. A first connecting rod 700a is used to couple the implant assemblies 10a, 10c, and a second connecting rod 700b is used to couple the implant assemblies 10b, 10d. In the illustrated embodiments, the implant assemblies 10a, 10c are coupled or secured together by placing the first connecting rod 700a through the lumens 26 in the receiver members 20 of the assemblies 10a, 10c (see also FIG. 5). Similarly, the assemblies 10b, 10d are secured together by placing the second connecting rod 700b through the lumens 26 in the receiver members 20 of the assemblies 10b, 10d. After the connecting rods 700a, 700b are desirably positioned, set screws 40 may be screwed onto the respective receiver members 20 to clamp against the rods 700a, 700b, thereby securing the rods 700a, 700b relative to the assemblies 10. The connecting rods 700a, 700b may extend generally in a direction of the spine (not shown). The cross-connector 800 is used to couple the connecting rods 700a, 700b together. In alternative embodiments, other assemblies (e.g., conventional pedicle screws and/or hooks) may be used alone or in combination with assemblies 10, in one or multiple levels.

In some instances, after the assembly 10 has been implanted or deployed, it may be desired to remove the assembly 10. For example, the condition of the bone (e.g., vertebra) may require the implanted assembly 10 be removed and/or replaced with a different assembly 10 (e.g., an assembly 10 with a different size). In such cases, the above process may be performed in a reverse manner to un-deploy the deployed arms 22. In some embodiments, the un-deployment of the arms 22 may be performed using the same deployment device 200 used to deploy the arms 22, or with a different deployment device 200 with the same or similar configuration as that used to deploy the arms 22. Thus, the term "deployment tool" is not limited to a device for deploying arm(s) of an assembly, and may refer to a device that is capable of un-deploying arms 22 of the assembly 10. In other embodiments, instead of using the same deployment device 200, or a different deployment device 200 with the same or similar configuration as that used to deploy the arms 22, a separate un-deployment device or tool dedicated to un-deploying the arms 22 may be provided. As used in this specification, the term "un-deployment device" may refer to the same deployment device 200 discussed herein, or to a separate device that is different from the deployment device 200, and may have a different configuration as that of the deployment device 200.

If a separate un-deployment device is provided, portions of the un-deployment device which requires handling by the operator's hand(s) should be composed of a material that helps prevent the un-deployment device from slipping out of the operator's hands in a bloody or oily environment or the like. Such materials may include frictional materials, for example, materials having uneven surfaces, to facilitate gripping of the un-deployment device. In some embodiments, the un-deployment device is designed and composed of materials to help the un-deployment tool maintain structural integrity and perform consistently through repeated use, cleaning, and sterilization processes, such as gas or steam processes that are standard sterilization processes in the spine surgical instruments field. For example, the un-deployment device may be composed of stainless steel, titanium, thermoplastic and other like materials suited for repeated use and sterilization of the un-deployment device. Also, in some embodiments, the un-deployment device has a configuration so as to be easily and substantially cleaned and sterilized. In addition, in some embodiments, the un-deployment device is sized and is of a weight so that a user can easily (e.g., using one hand) use the un-deployment device to perform various functions described herein. Further, in some embodiments, the un-deployment device may have a configuration that allows a user to easily perform the un-deployment (e.g., collapsing of the arms 22) of the assembly 10 using the force of one hand.

If an assembly 10 is desired to be removed from the patient, the cross-connector 800 is first removed from any connecting rod(s) 700 (if a cross-connector 800/rod 700 configuration is used). For example, each cross-connector 800 may be removed by unclamping the U-shaped clamps from the rods 700. Next, the set screws 40 and connecting rods 700, if any, are removed from the receiver member 20 of the assembly 10. When using the un-deployment device 200 to un-deploy the arms 22, the threaded section 404 of the shaft 210 of the deployment device 200 is first screwed into the receiver member 20 as discussed above. In some embodiments, the coupling of the shaft 210 to the receiver member 20 causes the secure ring 120 of the assembly 10 to be pressed downwards/distally.

Next, the member 220 of the device 200 is advanced distally so that it can engage with the protrusion 146 of the actuator 24, as discussed above. In exemplary embodiments, the member 220 of the device 200, when used in the un-deployment process, may be utilized as a push rod, and the actuator 24 of the assembly 10 may be utilized as an un-deployment actuator or rod. In one embodiment, the engaging mechanism 402 of the member 220 may be engaged with the protrusion 146 of the actuator 24 by advancing the member 220 so that the head 25 of the actuator 24 fits through the opening 150 of the member 220. The member 220 may have dedicated markers to indicate proper mating between the member 220 and the head 25 (and therefore, the protrusion 146), as similarly discussed herein.

After the end plate 154 of the member 220 has been translated past the head 25, the member 220 may be engaged with the head 25 as discussed above (e.g., the head 25 is locked or engaged against the inner surface of the end plate 154, as shown in FIG. 16B). The now connected member 220 may then be turned counter-clockwise to actuate the un-locking mechanism or process. For example, the exposed proximal end of the deployment member 220 may be rotated (e.g., finger-tightened counter-clockwise) to pull the actuator 24 proximally (e.g., about 1 mm to about 8 mm) relative to region 15 to unsecure and/or unlock deployment of device 10 (see FIGS. 3 and 4).

For example, since edge portions 148 (defining the slot 150) of member 220 are already engaged with protrusion 146 of actuator 24, turning member 220 counter-clockwise (i.e., in the opposite direction shown in FIG. 16B) will advance/unscrew actuator 24 proximally (approximately 2 mm) relative to second body region 15, with the threaded distal end of actuator 24 advancing proximally (e.g., upwards) relative to the inner threaded region of second body region 15. Thus, such proximal movement of actuator 24 unlocks actuator 24, and allows for the proper undeployment clearance for the required movement of actuator 24 to un-deploy the arms 22. This has the effect of moving head 25 of actuator 24 proximally, thereby providing a clearance (i.e., the distance between bottom surface 147 of protrusion 146 and face 152 of the first body region 18) needed for retracting/undeploying deployed arms 22. In some embodiments, un-deployment device 200 may include dedicated markers on member 220 to indicate proper unlocking and clearance gain.

After achieving the clearance needed for the movement required for undeploying (e.g., collapsing or flattening) the arms 22, the member 220 may then be used to un-deploy the arms 22. In exemplary embodiments, the member 220 is rotated and/or retracted proximally to disengage with the protrusion 146 of the actuator 24. The member 220 is continued to be retracted proximally until it is proximal to the head 25 of the actuator 24. The member 220 is then rotated about 90° either clockwise or counter-clockwise. Next, the member 220 is advanced distally such that the end surface of the end plate 154 can engage with the head 25 of the actuator 24. Unlike the deployment process in which the inner surface of the end plate 154 is used to engage with the bottom surface of head 25 (so that member 220 can be used to pull head 25 proximally), in the un-deployment process, the end (outer) surface of end plate 154 is used to engage with the top surface of head 25 to thereby allow member 220 to push head 25 distally.

In exemplary embodiments, the connector member 233 is then releasably secured to the tube 210 and the deployment member 220 as discussed above. A user operating the un-deployment device 200 may use one hand to turn the handle 216 on the un-deployment tool 200 counter-clockwise (e.g., while the other hand applies counter resistance using the grip handle 214), causing the member 220 to distally translate and in turn push against the surface of the head 25 of the actuator 24. Rotation of the handle 216 causes rotation of handle member 238, which thereby causes the internal tube 235 to move linearly (e.g., pulled or pushed), which in turn causes the deployment member 220 to move linearly (e.g., translate proximally or distally). The actuator 24 engaged with the deployment member 220 thus moves linearly as well.

Movement of the actuator 24 distally causes the second body region 15 of the implant assembly 10 to move distally, thereby applying tension to the arms 22. This causes the deployed arms 22 to flatten or collapse, and thus un-deploys the implant assembly 10 in the bone (e.g., the arms 22 assume the collapsed state). While this is occurring, the user's other hand may apply a counter-resistance to the turning motion, e.g., by holding the grip handle 214. Such technique results in minimal force transferred to the vertebrae, other than the forces associated with the flattening or collapsing of the arms 22 in the bone.

In one embodiment, the undeployment device 200 includes a mechanical movement limiter (e.g., a stopper, such as that in a form of a protrusion) that stops the linear motion of the actuator 24 and/or of the member 220, when the assembly 10 is fully un-deployed and in the collapsed state (e.g., reaches full flattening by the arms 22). This movement limiter may be configured to vary to match different sizes of the assembly 10 as discussed above. In some embodiments, the mechanical movement limiter may be adjustable—e.g., by changing a position of a stopper. In such cases, the sizes of different implant assemblies may be marked on the movement limiter for allowing a user to properly adjust the movement limiter to suit a particular size of an implant assembly.

In exemplary embodiment, the un-deployment device 200 may further include a mechanical force limiting mechanism to limit the pushing force exerted onto the actuator 24. In one embodiment, the force limiting mechanism may be a torque limiting mechanism that forms part of the torque handle 216 on the un-deployment device. For example, a slip mechanism may be provided which allows mechanical slippage when an amount of torque applied to the handle 216 (or an amount of pushing force applied to the member 220) exceeds a certain amount. Torque limiting mechanisms are well known in the art. This force limiting mechanism may vary for different sizes of the implant assembly 10 (e.g., 5.5 mm, 6.5 mm, or 7.5 mm), as discussed above. In some embodiments, the force limiting mechanism may be adjustable. In such cases, the sizes of different implant assemblies may be marked on the force limiting mechanism for allowing a user to properly adjust the force limiting mechanism to suit a particular size of an implant assembly 10. In some embodiments, the force limiting mechanism may be selectively configured to limit the pushing force on the member 220, and/or on the actuator 24, (e.g., not to exceed $2600^{+150}$ [N] for an assembly 10 with a size of about 5.5 mm, not to exceed $2800^{+150}$ [N] for an assembly 10 with a size of about 6.5 mm, and not to exceed $3000^{+150}$ [N] for an assembly 10 with a size of about 7.5 mm).

Next, the un-deployment device 200 may be disconnected or disengaged from the assembly 10. For such purpose, the forces applied onto the handles 214, 216 are released, and the member 220 is retracted proximally to disconnect from the head 25. The counter rotation sleeve 212 is then advanced so that the engaging portion(s) 410 of the counter rotation sleeve 212 is mated into the slot(s) at the receiver member 20 (as in FIG. 15B). The user then turns the grip handle 214 (e.g., counter-clockwise) to unscrew the threaded section 404 of the shaft 210 from the receiver member 20, while using another hand to grip onto the counter rotation sleeve 212. In particular, the counter rotation sleeve 212 may be used to hold the receiver 20 in place relative to the bone (e.g., vertebra), so that the shaft 210 may be unscrewed relative to the receiver member 20 without causing the receiver member 20 to rotate in a same direction as the turning of the shaft 210. The grip handle 214 is turned until the shaft 210 has been completely disconnected from the receiver member 20 of the assembly 10.

After arms 22 have been fully retracted to their un-deployed positions, and after un-deployment device 200 has been detached from assembly 10, assembly 10 can then be removed from the bone. For example, assembly 10 may be turned in an opposite direction from that in which it was previously screwed into the bone. If there are additional assemblies 10 that are desired to be removed, the above process may be repeated to remove other assemblies 10.

As illustrated in the above embodiments, the assembly 10 is advantageous in that it can be easily implanted and deployed. The assembly 10 is also advantageous in that it can be easily un-deployed and removed from the implanted position if desired. Also, the deployment (or un-deployment) device 200 is advantageous in that it can be easily connected to, and disconnected from, the assembly 10, and that it allows anchoring and un-anchoring of the assembly 10 relative to the bone to be performed quickly and easily.

Figure 20B:
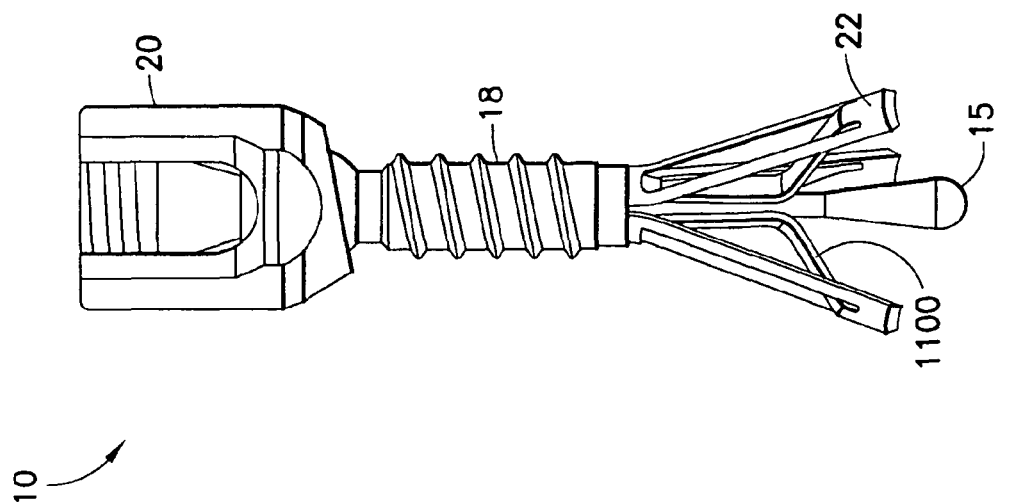
FIGS. 20A-20B illustrate an alternative embodiment of a bone stabilization device or assembly according to the present disclosure.
Figure 20A:
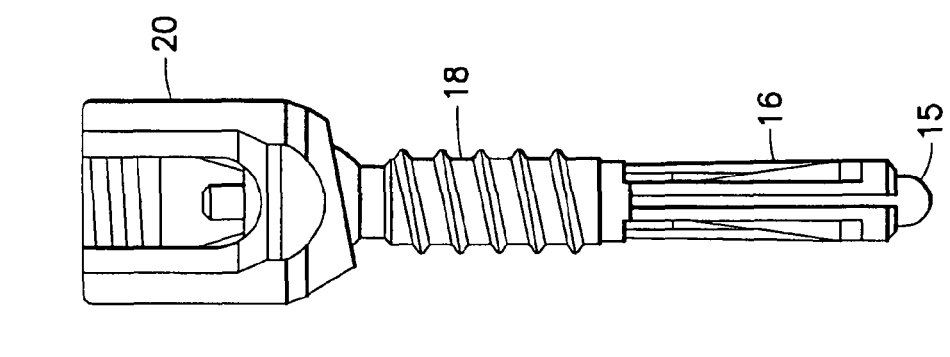

In exemplary embodiments, arms 22 of assembly 10 are deployed by pulling actuator 24 proximally. In other embodiments, assembly 10 may be configured so that arms 22 are deployed by advancing actuator 24 distally. FIG. 20A illustrates an assembly 10 having a plurality of arms 22, wherein each arm has a lever or lever element 1100 coupled or connected thereto. In exemplary embodiments, arms 22 and levers 1100 are formed from a tubing by making cuts onto the tubing. For example, each lever 1100 may be connected or coupled to actuator 24, or to second body region 15. During use, actuator 24 is advanced distally so that second body region 15 is also advanced distally. As second body region 15 is advanced distally, the levers 1100 are bent in the manner shown in FIG. 20B, thereby pushing the arms 22 radially outward to a deployed state. In the event that the implant assembly of FIG. 20B is desired to be removed after it has been implanted, the second body region 15 may be retracted proximally to move the arms 22 radially inward back to their undeployed positions (e.g., the collapsed state).

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. An orthopedic device comprising:
   (a) a body that defines a longitudinal axis, said body including: (i) a first body region defining a first lumen, (ii) a second body region defining a channel extending within the interior of the second body region, wherein the second body region is separately formed from the first body region, and wherein the first and second body regions are abuttingly engaged to each other and (iii) an anchor region positioned at least in part between the first body region and the second body region, wherein said anchor region comprises a first anchor element end region coupled, secured or connected to the first body region, and a second anchor element end region coupled, secured or connected to the second body region; and
   (b) an actuator, at least a first portion of the actuator configured and dimensioned to be at least partially disposed within the first lumen, and at least a second portion of the actuator configured and dimensioned to be: (i) at least partially disposed within the channel of the second body region, and (ii) releasably coupled with respect to the second body region; wherein the anchor region defines a plurality of anchoring elements moveable between a non-deployed state and a plurality of deployed states; and wherein linear movement of the actuator within the body relative to the first body region causes the second body region to be displaced linearly towards the first body region, thereby causing each of the anchoring elements to deploy outwardly relative to the longitudinal axis of the body to define one of the plurality of deployed states, and further comprising: a receiver member defining a third lumen and having a threaded region near the proximal end of the receiver member, the receiver member being configured and dimensioned to house the proximal end of the first body region; a securing member, the securing member configured and dimensioned to be disposed within the third lumen of the receiver member and to be positioned above proximal end of the first body region; a rod positioned above the securing member; and a screw, the screw configured and dimensioned to threadably engage with the threaded region of the receiver member to press the rod towards the securing member, thereby: (i) securing the rod between the securing member and the screw, and (ii) stabilizing the rod relative to the receiver member, wherein each anchoring element of the plurality of anchoring elements further includes at least one hinge region configured and dimensioned to provide a hinge when each anchoring element moves outwardly to define each deployed state of the plurality of deployed states, wherein each hinge region buckles or bends in a predetermined manner when each anchoring element moves outwardly to define each deployed state of the plurality of deployed states, and wherein the second body region includes: (i) an inner region, the inner region at least partially disposed within the anchor region when the anchor region is in the non-deployed state, and (ii) a second body end region, and wherein the inner region includes a protrusion, the protrusion configured and dimensioned to allow said at least one hinge region to be substantially adjacent to the protrusion when the anchor region is in the non-deployed state, and wherein said at least one hinge region comprises a scored or thinned region, and wherein for each of said anchoring elements, portions of the anchoring element on both sides of said hinge region extending between said hinge region and said first and second anchor element end regions are not curved and remain not curved after said hinge region buckles or bends.

2. The device of claim 1, wherein each of the plurality of anchoring elements is bounded by a first anchor element end region and a second anchor element end region, wherein the first anchor element end region is adjacent to the first body region, and the second anchor element end region is adjacent to the second body region.

3. The device of claim 2, wherein the first anchor element end region is coupled or secured to the first body region, and the second anchor element end region is coupled or secured to the second body region.

4. The device of claim 2, wherein the first anchor element end region is integrally formed from the first body region, and the second anchor element end region is integrally formed from the second body region.

5. The device of claim 1, wherein the anchor region defines a second lumen when the anchor region is in the non-deployed state.

6. The device of claim 5, wherein at least a portion of the second body region is disposed within the second lumen of the anchor region when the anchor region is in the non-deployed state.

7. The device of claim 5, wherein at least a portion of the first body region is disposed within the second lumen of the anchor region when the anchor region is in the non-deployed state.

8. The device of claim 1, wherein the first body region, the second body region, and the anchor region in the non-deployed state are hollow regions.

9. The device of claim 1, wherein the first body region or the second body region includes external threads.

10. The device of claim 1, wherein the anchor region includes external threads.

11. The device of claim 1, wherein the second body end region is not substantially disposed within the anchor region when the anchor region is in the non-deployed state.

12. The device of claim 1, wherein the inner region is substantially disposed within the anchor region when the anchor region is in the non-deployed state.

13. The device of claim 1, wherein the inner region is removable.

14. The device of claim 1, wherein the anchor region is substantially linear when the anchor region is in the non-deployed state.

15. The device of claim 1, wherein the anchor region is substantially aligned with the longitudinal axis of the body when the anchor region is in the non-deployed state.

16. The device of claim 1, wherein the anchor region in the non-deployed state has a substantially uniform outer diameter.

17. The device of claim 1, wherein the body is a hollow body, and wherein the first body region, the anchor region, and the second body region are integrally formed from the hollow body.

18. An orthopedic device comprising:
(a) a body that defines a longitudinal axis, said body including: (i) a first body region defining a first lumen, (ii) a second body region defining a channel extending within the interior of the second body region, wherein the second body region is separately formed from the first body region, and wherein the first and second body regions are abuttingly engaged to each other and (iii) an anchor region positioned at least in part between the first body region and the second body region, wherein said anchor region comprises a first anchor element end region coupled, secured or connected to the first body region, and a second anchor element end region coupled, secured or connected to the second body region; and
(b) an actuator, at least a first portion of the actuator configured and dimensioned to be at least partially disposed within the first lumen, and at least a second portion of the actuator configured and dimensioned to be: (i) at least partially disposed within the channel of the second body region, and (ii) releasably coupled with respect to the second body region; wherein the anchor region defines a plurality of anchoring elements moveable between a non-deployed state and a plurality of deployed states; and wherein linear movement of the actuator within the body relative to the first body region causes the second body region to be displaced linearly towards the first body region, thereby causing each of the anchoring elements to deploy outwardly relative to the longitudinal axis of the body to define one of the plurality of deployed states, and
further comprising: a receiver member defining a third lumen and having a threaded region near the proximal end of the receiver member, the receiver member being configured and dimensioned to house the proximal end of the first body region; a securing member, the securing member configured and dimensioned to be disposed within the third lumen of the receiver member and to be positioned above proximal end of the first body region; a rod positioned above the securing member; and a screw, the screw configured and dimensioned to threadably engage with the threaded region of the receiver member to press the rod towards the securing member, thereby: (i) securing the rod between the securing member and the screw, and (ii) stabilizing the rod relative to the receiver member,
wherein each anchoring element of the plurality of anchoring elements further includes at least one hinge region configured and dimensioned to provide a hinge when each anchoring element moves outwardly to define each deployed state of the plurality of deployed states, wherein each hinge region buckles or bends in a predetermined manner when each anchoring element moves outwardly to define each deployed state of the plurality of deployed states, and wherein for each of said anchoring elements, portions of the anchoring element on both sides of said hinge region extending between said hinge region and said first and second anchor element end regions are not curved and remain not curved after said hinge region buckles or bends; and
wherein the second body region includes: (i) an inner region, the inner region at least partially disposed within the anchor region when the anchor region is in the non-deployed state, and (ii) a second body end region, and wherein the inner region includes a protrusion, the protrusion configured and dimensioned to allow said at least one hinge region to be substantially adjacent to the protrusion when the anchor region is in the non-deployed state, and wherein said inner region comprises a smooth shaft and said protrusion comprises a smooth annular band with a diameter greater than that of said smooth shaft.

\* \* \* \* \*